(12) United States Patent
Chen et al.

(10) Patent No.: US 7,915,011 B2
(45) Date of Patent: *Mar. 29, 2011

(54) HOST CELL MODIFICATIONS THAT IMPROVE PEPTIDE PRODUCTION AND DOWNSTREAM PROCESSING

(75) Inventors: Qi Chen, Wallingford, PA (US); Qiong Cheng, Wilmington, DE (US); Kevin Michael Croker, Hockessin, DE (US); Thomas Eduard Friedmann, Hockessin, DE (US); Kristin Ruebling-Jass, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/575,550

(22) Filed: Oct. 8, 2009

(65) Prior Publication Data

US 2010/0227361 A1    Sep. 9, 2010

Related U.S. Application Data

(63) Continuation-in-part of application No. 12/398,358, filed on Mar. 5, 2009, now Pat. No. 7,662,587.

(51) Int. Cl.
  C12P 21/00 (2006.01)
  C12N 1/21 (2006.01)

(52) U.S. Cl. .................. 435/69.1; 435/252.33

(58) Field of Classification Search .......... None
  See application file for complete search history.

(56) References Cited

U.S. PATENT DOCUMENTS

| | | |
|---|---|---|
| 6,620,419 B1 | 9/2003 | Lintner |
| 7,129,326 B2 | 10/2006 | Janssen et al. |
| 7,220,405 B2 | 5/2007 | Huang et al. |
| 7,285,264 B2 | 10/2007 | O'Brien et al. |
| 7,309,482 B2 | 12/2007 | Buseman-Williams et al. |
| 7,341,604 B2 | 3/2008 | Rothe et al. |
| 7,427,656 B2 | 9/2008 | DeCarolis et al. |
| 7,662,587 B1 * | 2/2010 | Cheng et al. ............ 435/69.1 |
| 7,662,913 B2 | 2/2010 | DeCarolis et al. |
| 7,678,883 B2 | 3/2010 | Cheng et al. |
| 2002/0098524 A1 | 7/2002 | Murray et al. |
| 2003/0152976 A1 | 8/2003 | Janssen et al. |
| 2003/0185870 A1 | 10/2003 | Grinstaff et al. |
| 2005/0112692 A1 | 5/2005 | Murray et al. |
| 2005/0226839 A1 | 10/2005 | Huang et al. |
| 2006/0073111 A1 | 4/2006 | O'Brien et al. |
| 2006/0171885 A1 | 8/2006 | Janssen et al. |
| 2006/0199206 A1 | 9/2006 | Wang et al. |
| 2007/0065387 A1 | 3/2007 | Beck et al. |
| 2007/0067924 A1 | 3/2007 | Beck et al. |
| 2007/0110686 A1 | 5/2007 | Lowe et al. |
| 2007/0196305 A1 | 8/2007 | Wang et al. |
| 2007/0249805 A1 | 10/2007 | Ittel et al. |
| 2008/0096246 A1 | 4/2008 | DeCarolis et al. |
| 2008/0107614 A1 | 5/2008 | Fahnestock et al. |
| 2008/0175798 A1 | 7/2008 | Beck et al. |
| 2008/0280810 A1 | 11/2008 | O'Brien et al. |
| 2009/0029902 A1 | 1/2009 | Cunningham et al. |

FOREIGN PATENT DOCUMENTS

| | | |
|---|---|---|
| WO | WO 2004/048399 A2 | 6/2004 |
| WO | WO 2008/054746 A1 | 5/2008 |
| WO | WO 2008/073368 A1 | 6/2008 |

OTHER PUBLICATIONS

DeLay Genetic interaction between the *Escherichia coli* AcpT phosphopantetheinyl transferase and the YejM inner membrane protein Genetics 178:1327-1337.*
Chen, Christina et al., High-Level Accumulation of a Recombinant Antibody Fragment in the Periplasm of *Escherichia coli* Requires a Triple-Mutant (degP prc spr) Host Strain, Biotechnology and Bioengineering, Mar. 5, 2004, pp. 463-474 vol. 85, No. 5, Wiley Periodicals, Inc.
Baba, Tomoya et al., Construction of *Escherichia coli* K-12 in-frame, single-gene knockout mutants: the Keio collection, Molecular Systems Biology, 2006, pp. 1-11, Article No. 2006.0008, EMBO and Nature Publishing Group.
Rapp, Mikaela et al., Experimentally based topology models for *E. coli* inner membrane proteins, Protein Science, 2004, pp. 937-945, vol. 13, Cold Spring Harbor Laboratory Press.
Daley, Daniel O. et al., Global Toplogy Analysis of the *Escherichia coli* Inner Membrane Proteome, Science, May 27, 2005, pp. 1321-1323, vol. 308.
De Lay, Nicholas et al., Genetic Interaction Between the *Escherichia coli* AcpT Phosphopantetheinyl Transferase and the YejM Inner Membrane Protein, Mar. 2008, pp. 1327-1337, vol. 178, Genetics Society of America.

* cited by examiner

*Primary Examiner* — Manjunath N Rao
*Assistant Examiner* — Kagnew H Gebreyesus

(57) ABSTRACT

Disrupting the expression of endogenous *Escherichia* host cell genes gcvA and spr provides mutant host cells having increased heterologous peptide production. The addition of a genetic modification to the coding region of gene yejM further enhances peptide production and facilitates easier downstream processing. Recombinant *Escherichia* host cells are provided as well as methods of using such host cells for heterologous peptide production.

22 Claims, 2 Drawing Sheets

SEQUENCE LISTING

```
<160> NUMBER OF SEQ ID NOS: 492

<210> SEQ ID NO 1
<211> LENGTH: 6
<212> TYPE: PRT
<213> ORGANISM: artificial sequence
<220> FEATURE:
<223> OTHER INFORMATION: Synthetic construct - tetracysteine tag

<400> SEQUENCE: 1

Cys Cys Pro Gly Cys Cys
1               5

<210> SEQ ID NO 2
<211> LENGTH: 6034
<212> TYPE: DNA
<213> ORGANISM: artificial sequence
<220> FEATURE:
<223> OTHER INFORMATION: plasmid

<400> SEQUENCE: 2
aagaaaccaa ttgtccatat tgcatcagac attgccgtca ctgcgtcttt tactggctct      60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcttacctg acgcttttta tcgcaactct ctactgtttc tccatacccg ttttttgggc    300
taacaggagg aattacatat gcagcagcgt ttccagtggc agttcgaaca gcagccgcgt    360
ggtcagcagc gtttccagtg gcagttcgaa cagcagccgc gtggtcagca gcgtttccag    420
tggcagttcg aacagcagcc ggaaggtcag cagcgtttcc agtggcagtt cgaacagcag    480
ggatcttgct gtccgggctg ttgcggatcc gaccctggca ttccgtggtg gaacattcgt    540
gctcctctga atgcaggtgc gggcatccct tggtggaata ttcgtgctcc gctgaacgcc    600
ggtggttccg gtccgggtag cggtggtaat acttctcagc tgtccacggg tggcggtaac    660
actagccagc tgagcacggg cggccctaaa aagccgggcg acccgggtat tccgtggtgg    720
aatatccgtg ccccgctgaa cgcaggtgcc ggcatcccgt ggtggaacat tcgtgcacct    780
ctgaatgctg gtggttccgg tccaggctct ggcggcaaca cttcccagct gtccaccggc    840
ggtggcaaca ccagccagct gtctactggt ggtccgaaga aaccgggtga ctaataaggc    900
gcgccgaccc agctttcttg tacaaagtgg ttgattcgag gctgctaaca aagcccgaaa    960
ggaagctgag ttggctgctg ccaccgctga gcaataacta gcataacccc ttggggcctc   1020
taaacgggtc ttgagggtt ttttgctgaa aggaggaact atatccggat atccacagga   1080
cgggtgtggt cgccatgatc gcgtagtcga tagtggctcc aagtagcgaa gcgagcagga   1140
ctgggcggcg gccaaagcgg tcggacagtg ctccgagaac gggtgcgcat agaaattgca   1200
tcaacgcata tagcgctagc agcacgccat agtgactggc gatgctgtcg gaatggacga   1260
tatcccgcaa gaggcccggc agtaccggca taaccaagcc tatgcctaca gcatccaggg   1320
tgacggtgcc gaggatgacg atgagcgcat tgttagattt catacacggt gcctgactgc   1380
gttagcaatt taactgtgat aaactaccgc attaaagctt gcagtggcgg ttttcatggc   1440
```

```
ttgttatgac tgtttttttg gggtacagtc tatgcctcgg gcatccaagc agcaagcgcg   1500
ttacgccgtg ggtcgatgtt tgatgttatg gagcagcaac gatgttacgc agcagggcag   1560
tcgccctaaa acaaagttaa acatcatgag ggaagcggtg atcgccgaag tatcgactca   1620
actatcagag gtagttggcg tcatcgagcg ccatctcgaa ccgacgttgc tggccgtaca   1680
tttgtacggc tccgcagtgg atggcggcct gaagccacac agtgatattg atttgctggt   1740
tacggtgacc gtaaggcttg atgaaacaac gcggcgagct ttgatcaacg accttttgga   1800
aacttcggct tcccctggag agagcagat tctccgcgct gtagaagtca ccattgttgt   1860
gcacgacgac atcattccgt ggcgttatcc agctaagcgc gaactgcaat ttggagaatg   1920
gcagcgcaat gacattcttg caggtatctt cgagccagcc acgatcgaca ttgatctggc   1980
tatcttgctg acaaaagcaa gagaacatag cgttgccttg gtaggtccag cggcggagga   2040
actctttgat ccggttcctg aacaggatct atttgaggcg ctaaatgaaa ccttaacgct   2100
atggaactcg ccgcccgact gggctggcga tgagcgaaat gtagtgctta cgttgtcccg   2160
catttggtac agcgcagtaa ccggcaaaat cgcgccgaag gatgtcgctg ccgactgggc   2220
aatggagcgc ctgccggccc agtatcagcc cgtcatactt gaagctagac aggcttatct   2280
tggacaagaa gaagatcgct tggcctcgcg cgcagatcag ttggaagaat ttgtccacta   2340
cgtgaaaggc gagatcacca aggtagtcgg caaataatgt ctaacaattc gttcaagctt   2400
ggctgttttg gcggatgaga aagattttc agcctgatac agattaaatc agaacgcaga   2460
agcggtctga taaacagaa tttgcctggc ggcagtagcg cggtggtccc acctgacccc   2520
atgccgaact cagaagtgaa acgccgtagc gccgatggta gtgtggggtc tccccatgcg   2580
agagtaggga actgccaggc atcaaataaa acgaaaggct cagtcgaaag actgggcctt   2640
tcgttttatc tgttgtttgt cggtgaacgc tctcctgagt aggacaaatc cgccgggagc   2700
ggatttgaac gttgcgaagc aacgcccgg agggtggcgg gcaggacgcc cgccataaac   2760
tgccaggcat caaattaagc agaaggccat cctgacggat ggcctttttg cgtttctaca   2820
aactcttttg tttattttc taaatacatt caaatatgta tccgctcatg agacaataac   2880
cctgataaat gcttcaataa tattgaaaaa ggaagagtat gagtattcaa catttccgtg   2940
tcgcccttat tccctttttt gcggcatttt gccttcctgt ttttgctcac ccagaaacgc   3000
tggtgaaagt aaaagatgct gaagatcagt tgggtgcacg agtgggttac atcgaactgg   3060
atctcaacag cggtaagatc cttgagagtt ttcgccccga agaacgtttt ccaatgatga   3120
gcacttttaa agttctgcta tgtggcgcgg tattatcccg tgttgacgcc gggcaagagc   3180
aactcggtcg ccgcatacac tattctcaga atgacttggt tgagtactca ccagtcacag   3240
aaaagcatct tacggatggc atgacagtaa gagaattatg cagtgctgcc ataaccatga   3300
gtgataacac tgcggccaac ttacttctga caacgatcgg aggaccgaag gagctaaccg   3360
cttttttgca acatggggg gatcatgtaa ctcgccttga tcgttgggaa ccggagctga   3420
atgaagccat accaaacgac gagcgtgaca ccacgatgcc tgtagcaatg gcaacaacgt   3480
tgcgcaaact attaactggc gaactactta ctctagcttc ccggcaacaa ttaatagact   3540
ggatggaggc ggataaagtt gcaggaccac ttctgcgctc ggcccttccg gctggctggt   3600
ttattgctga taaatctgga gccggtgagc gtgggtctcg cggtatcatt gcagcactgg   3660
ggccagatgg taagccctcc cgtatcgtag ttatctacac gacggggagt caggcaacta   3720
tggatgaacg aaatagacag atcgctgaga taggtgcctc actgattaag cattggtaac   3780
tgtcagacca agtttactca tatatacttt agattgattt aaaacttcat ttttaattta   3840
```

```
aaaggatcta ggtgaagatc cttttttgata atctcatgac caaaatccct taacgtgagt    3900
tttcgttcca ctgagcgtca gaccccgtag aaaagatcaa aggatcttct tgagatcctt    3960
ttttttctgcg cgtaatctgc tgcttgcaaa caaaaaaacc accgctacca gcggtggttt   4020
gtttgccgga tcaagagcta ccaactcttt ttccgaaggt aactggcttc agcagagcgc    4080
agataccaaa tactgtcctt ctagtgtagc cgtagttagg ccaccacttc aagaactctg    4140
tagcaccgcc tacatacctc gctctgctaa tcctgttacc agtggctgct gccagtggcg    4200
ataagtcgtg tcttaccggg ttggactcaa gacgatagtt accggataag gcgcagcggt    4260
cgggctgaac gggggggttcg tgcacacagc ccagcttgga gcgaacgacc tacaccgaac   4320
tgagatacct acagcgtgag ctatgagaaa gcgccacgct tcccgaaggg agaaaggcgg    4380
acaggtatcc ggtaagcggc agggtcggaa caggagagcg cacgagggag cttccagggg    4440
gaaacgcctg gtatctttat agtcctgtcg ggtttcgcca cctctgactt gagcgtcgat    4500
ttttgtgatg ctcgtcaggg gggcggagcc tatggaaaaa cgccagcaac gcggcctttt    4560
tacggttcct ggccttttgc tggccttttg ctcacatgtt ctttcctgcg ttatcccctg    4620
attctgtgga taaccgtatt accgcctttg agtgagctga taccgctcgc cgcagccgaa    4680
cgaccgagcg cagcgagtca gtgagcgagg aagcggaaga gcgcctgatg cggtatttc     4740
tccttacgca tctgtgcggt atttcacacc gcatatatgg tgcactctca gtacaatctg    4800
ctctgatgcc gcatagttaa gccagtatac actccgctat cgctacgtga ctgggtcatg    4860
gctgcgcccc gacacccgcc aacacccgct gacgcgccct gacgggcttg tctgctcccg    4920
gcatccgctt acagacaagc tgtgaccgtc tccgggagct gcatgtgtca gaggttttca    4980
ccgtcatcac cgaaacgcgc gaggcagcag atcaattcgc gcgcgaaggc gaagcggcat    5040
gcataatgtg cctgtcaaat ggacgaagca gggattctgc aaaccctatg ctactccgtc    5100
aagccgtcaa ttgtctgatt cgttaccaat tatgacaact tgacggctac atcattcact    5160
ttttcttcac aaccggcacg gaactcgctc gggctggccc cggtgcattt tttaaatacc    5220
cgcgagaaat agagttgatc gtcaaaacca acattgcgac cgacggtggc gataggcatc    5280
cgggtggtgc tcaaaagcag cttcgcctgg ctgatacgtt ggtcctcgcg ccagcttaag    5340
acgctaatcc ctaactgctg gcggaaaaga tgtgacagac gcgacggcga caagcaaaca    5400
tgctgtgcga cgctggcgat atcaaaattg ctgtctgcca ggtgatcgct gatgtactga    5460
caagcctcgc gtacccgatt atccatcggt ggatggagcg actcgttaat cgcttccatg    5520
cgccgcagta acaattgctc aagcagattt atcgccagca gctccgaata gcgcccttcc    5580
ccttgcccgg cgttaatgat ttgcccaaac aggtcgctga atgcggctg gtgcgcttca    5640
tccgggcgaa agaaccccgt attggcaaat attgacggcc agttaagcca ttcatgccag    5700
taggcgcgcg gacgaaagta aacccactgg tgataccatt cgcgagcctc cggatgacga    5760
ccgtagtgat gaatctctcc tggcgggaac agcaaaatat cacccggtcg gcaaacaaat    5820
tctcgtccct gattttttcac cacccccctga ccgcgaatgg tgagattgag aatataacct   5880
ttcattccca gcggtcggtc gataaaaaaa tcgagataac cgttggcctc aatcggcgtt    5940
aaacccgcca ccagatgggc attaaacgag tatcccggca gcagggatc attttgcgct     6000
tcagccatac ttttcatact cccgccattc agag                                6034
```

<210> SEQ ID NO 3
<211> LENGTH: 53
<212> TYPE: PRT
<213> ORGANISM: artificial sequence

```
<220> FEATURE:
<223> OTHER INFORMATION: inclusion body tag IBT139

<400> SEQUENCE: 3

Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Gln Pro Glu Gly Gln Gln Arg Phe Gln Trp
        35                  40                  45

Gln Phe Glu Gln Gln
    50

<210> SEQ ID NO 4
<211> LENGTH: 129
<212> TYPE: PRT
<213> ORGANISM: artificial sequence
<220> FEATURE:
<223> OTHER INFORMATION: Synthetic construct. Multi-block hair-binding
      peptide

<400> SEQUENCE: 4

Gly Ser Asp Pro Gly Ile Pro Trp Trp Asn Ile Arg Ala Pro Leu Asn
1               5                   10                  15

Ala Gly Ala Gly Ile Pro Trp Trp Asn Ile Arg Ala Pro Leu Asn Ala
            20                  25                  30

Gly Gly Ser Gly Pro Gly Ser Gly Gly Asn Thr Ser Gln Leu Ser Thr
        35                  40                  45

Gly Gly Gly Asn Thr Ser Gln Leu Ser Thr Gly Gly Pro Lys Lys Pro
    50                  55                  60

Gly Asp Pro Gly Ile Pro Trp Trp Asn Ile Arg Ala Pro Leu Asn Ala
65                  70                  75                  80

Gly Ala Gly Ile Pro Trp Trp Asn Ile Arg Ala Pro Leu Asn Ala Gly
                85                  90                  95

Gly Ser Gly Pro Gly Ser Gly Gly Asn Thr Ser Gln Leu Ser Thr Gly
            100                 105                 110

Gly Gly Asn Thr Ser Gln Leu Ser Thr Gly Gly Pro Lys Lys Pro Gly
        115                 120                 125

Asp

<210> SEQ ID NO 5
<211> LENGTH: 579
<212> TYPE: DNA
<213> ORGANISM: artificial sequence
<220> FEATURE:
<223> OTHER INFORMATION: Synthetic construct - chimeric gene encoding
      fusion peptide IBT139.CCPGCC-HC776124

<400> SEQUENCE: 5
atgcagcagc gtttccagtg gcagttcgaa cagcagccgc gtggtcagca gcgtttccag       60
tggcagttcg aacagcagcc gcgtggtcag cagcgtttcc agtggcagtt cgaacagcag      120
ccggaaggtc agcagcgttt ccagtggcag ttcgaacagc agggatcttg ctgtccgggc      180
tgttgcggat ccgaccctgg cattccgtgg tggaacattc gtgctcctct gaatgcaggt      240
gcgggcatcc cttggtggaa tattcgtgct ccgctgaacg ccgtggttc cggtccgggt      300 agcggtggta atacttctca gctgtccacg ggtggcggta acactagcca gctgagcacg      360
ggcggcccta aaaagccggg cgaccgggt attccgtggt ggaatatccg tgccccgctg      420
aacgcaggtg ccggcatccc gtggtggaac attcgtgcac ctctgaatgc tggtggttcc      480
```

```
ggtccaggct ctggcggcaa cacttcccag ctgtccaccg gcggtggcaa caccagccag    540
ctgtctactg gtggtccgaa gaaaccgggt gactaataa                           579
```

<210> SEQ ID NO 6
<211> LENGTH: 190
<212> TYPE: PRT
<213> ORGANISM: artificial sequence
<220> FEATURE:
<223> OTHER INFORMATION: Synthetic construct - fusion peptide
      IBT139.CCPGCC-HC776124

<400> SEQUENCE: 6

```
Gln Gln Arg Phe Gln Trp Gln Phe Glu Gln Gln Pro Arg Gly Gln Gln
1               5                   10                  15

Arg Phe Gln Trp Gln Phe Glu Gln Gln Pro Arg Gly Gln Gln Arg Phe
            20                  25                  30

Gln Trp Gln Phe Glu Gln Gln Pro Glu Gly Gln Gln Arg Phe Gln Trp
        35                  40                  45

Gln Phe Glu Gln Gln Gly Ser Cys Cys Pro Gly Cys Cys Gly Ser Asp
    50                  55                  60

Pro Gly Ile Pro Trp Trp Asn Ile Arg Ala Pro Leu Asn Ala Gly Ala
65                  70                  75                  80

Gly Ile Pro Trp Trp Asn Ile Arg Ala Pro Leu Asn Ala Gly Gly Ser
                85                  90                  95

Gly Pro Gly Ser Gly Gly Asn Thr Ser Gln Leu Ser Thr Gly Gly Gly
            100                 105                 110

Asn Thr Ser Gln Leu Ser Thr Gly Gly Pro Lys Lys Pro Gly Asp Pro
        115                 120                 125

Gly Ile Pro Trp Trp Asn Ile Arg Ala Pro Leu Asn Ala Gly Ala Gly
    130                 135                 140

Ile Pro Trp Trp Asn Ile Arg Ala Pro Leu Asn Ala Gly Gly Ser Gly
145                 150                 155                 160

Pro Gly Ser Gly Gly Asn Thr Ser Gln Leu Ser Thr Gly Gly Gly Asn
                165                 170                 175

Thr Ser Gln Leu Ser Thr Gly Gly Pro Lys Lys Pro Gly Asp
            180                 185                 190
```

<210> SEQ ID NO 7
<211> LENGTH: 6034
<212> TYPE: DNA
<213> ORGANISM: artificial sequence
<220> FEATURE:
<223> OTHER INFORMATION: plasmid

<400> SEQUENCE: 7

```
aagaaaccaa ttgtccatat tgcatcagac attgccgtca ctgcgtcttt tactggctct    60
tctcgctaac caaaccggta accccgctta ttaaaagcat tctgtaacaa agcgggacca   120
aagccatgac aaaaacgcgt aacaaaagtg tctataatca cggcagaaaa gtccacattg   180
attatttgca cggcgtcaca ctttgctatg ccatagcatt tttatccata agattagcgg   240
atcttacctg acgctttta tcgcaactct ctactgtttc tccataccg ttttttgggc    300 taacaggagg aattacatat ggctagctgc ggtcaacaac gttttcaatg caattcgaa   360 caacagccgc gttgcggcca gcaacgcttc caatggcagt ttgaacagca accgcgttgc   420
ggtcagcaac gtttccagtg caatttgaa caacagccag agtgcggcca gcagcgcttt   480
cagtggcagt tcgagcagca gccgtgcgga tcttgctgtc cgggctgttg cggatccgat   540
```

```
ccatctgctc aatctcaact gcctgataaa cattctggtc tgcatgaacg cgctcctcaa      600
cgttacggtc cggaggaggc ggcgaagaaa gaagaggcgg ctaaaaagcc ggctcacatt      660
aataagacca acccgcatca gggcaaccat cactccgaaa agacccagcg tcagggctcc      720
ggtggcggcg gtagcggcag cggtggcggt ggttctgact cccatcacaa ccatcacaag      780
caggactccc gccctcagca ccgtaagacg ccaaacggcg gtggtgactc tcaccataac      840
caccacaaac aggactctcg cccgcagcac cgcaaaaccc ctaacggtaa ataataaggc      900
gcgccgaccc agcttccttg tacaaagtgg ttgattcgag gctgctaaca aagcccgaaa      960
ggaagctgag ttggctgctg ccaccgctga gcaataacta gcataacccc ttggggcctc     1020
taaacgggtc ttgaggggtt ttttgctgaa aggaggaact atatccggat atccacagga     1080
cgggtgtggt cgccatgatc gcgtagtcga tagtggctcc aagtagcgaa gcgagcagga     1140
ctgggcggcg gccaaagcgg tcggacagtg ctccgagaac gggtgcgcat agaaattgca     1200
tcaacgcata tagcgctagc agcacgccat agtgactggc gatgctgtcg gaatggacga     1260
tatcccgcaa gaggcccggc agtaccggca taaccaagcc tatgcctaca gcatccaggg     1320
tgacggtgcc gaggatgacg atgagcgcat tgttagattt catacacggt gcctgactgc     1380
gttagcaatt taactgtgat aaactaccgc attaaagctt gcagtggcgg ttttcatggc     1440
ttgttatgac tgttttttg gggtacagtc tatgcctcgg gcatccaagc agcaagcgcg     1500
ttacgccgtg ggtcgatgtt tgatgttatg gagcagcaac gatgttacgc agcagggcag     1560
tcgccctaaa acaaagttaa acatcatgag ggaagcggtg atcgccgaag tatcgactca     1620
actatcagag gtagttggcg tcatcgagcg ccatctcgaa ccgacgttgc tggccgtaca     1680
tttgtacggc tccgcagtgg atggcggcct gaagccacac agtgatattg atttgctggt     1740
tacggtgacc gtaaggcttg atgaaacaac gcggcgagct ttgatcaacg acctttggga     1800
aacttcggct tccctggag agagcagat tctccgcgct gtagaagtca ccattgttgt     1860
gcacgacgac atcattccgt ggcgttatcc agctaagcgc gaactgcaat ttggagaatg     1920
gcagcgcaat gacattcttg caggtatctt cgagccagcc acgatcgaca ttgatctggc     1980
tatcttgctg acaaaagcaa gagaacatag cgttgccttg gtaggtccag cggcggagga     2040
actctttgat ccggttcctg aacaggatct atttgaggcg ctaaatgaaa ccttaacgct     2100
atggaactcg ccgcccgact gggctggcga tgagcgaaat gtagtgctta cgttgtcccg     2160
catttggtac agcgcagtaa ccggcaaaat cgcgccgaag gatgtcgctg ccgactgggc     2220
aatggagcgc ctgccggccc agtatcagcc cgtcatactt gaagctagac aggcttatct     2280
tggacaagaa gaagatcgct tggcctcgcg cgcagatcag ttggaagaat tgtccactaa    2340
cgtgaaaggc gagatcacca aggtagtcgg caaataatgt ctaacaattc gttcaagctt     2400
ggctgttttg gcggatgaga gaagattttc agcctgatac agattaaatc agaacgcaga     2460
agcggtctga taaaacagaa tttgcctggc ggcagtagcg cggtggtccc acctgacccc     2520
atgccgaact cagaagtgaa acgccgtagc gccgatggta gtgtggggtc tccccatgcg     2580
agagtaggga actgccaggc atcaaataaa acgaaaggct cagtcgaaag actgggcctt     2640
tcgttttatc tgttgtttgt cggtgaacgc tctcctgagt aggacaaatc cgccgggagc     2700
ggatttgaac gttgcgaagc aacgccgg agggtgcgg gcaggacgcc cgccataaac     2760
tgccaggcat caaattaagc agaaggccat cctgacggat ggcctttttg cgtttctaca     2820
aactcttttg tttattttc taaatacatt caaatatgta tccgctcatg agacaataac     2880
cctgataaat gcttcaataa tattgaaaaa ggaagagtat gagtattcaa catttccgtg     2940
```

```
tcgcccttat tccctttttt gcggcatttt gccttcctgt ttttgctcac ccagaaacgc    3000
tggtgaaagt aaaagatgct gaagatcagt tgggtgcacg agtgggttac atcgaactgg    3060
atctcaacag cggtaagatc cttgagagtt ttcgccccga agaacgtttt ccaatgatga    3120
gcacttttaa agttctgcta tgtggcgcgg tattatcccg tgttgacgcc gggcaagagc    3180
aactcggtcg ccgcatacac tattctcaga atgacttggt tgagtactca ccagtcacag    3240
aaaagcatct tacggatggc atgacagtaa gagaattatg cagtgctgcc ataaccatga    3300
gtgataacac tgcggccaac ttacttctga caacgatcgg aggaccgaag gagctaaccg    3360
cttttttgca caacatgggg gatcatgtaa ctcgccttga tcgttgggaa ccggagctga    3420
atgaagccat accaaacgac gagcgtgaca ccacgatgcc tgtagcaatg gcaacaacgt    3480
tgcgcaaact attaactggc gaactactta ctctagcttc ccggcaacaa ttaatagact    3540
ggatggaggc ggataaagtt gcaggaccac ttctgcgctc ggcccttccg gctggctggt    3600
ttattgctga taaatctgga gccggtgagc gtgggtctcg cggtatcatt gcagcactgg    3660
ggccagatgg taagccctcc cgtatcgtag ttatctacac gacggggagt caggcaacta    3720
tggatgaacg aaatagacag atcgctgaga taggtgcctc actgattaag cattggtaac    3780
tgtcagacca gtttactcat tatatacttt agattgattt aaaacttcat ttttaattta    3840
aaaggatcta ggtgaagatc cttttttgata atctcatgac caaaatccct taacgtgagt    3900
tttcgttcca ctgagcgtca gacccegtag aaaagatcaa aggatcttct tgagatcctt    3960
tttttctgcg cgtaatctgc tgcttgcaaa caaaaaaacc accgctacca gcggtggttt    4020
gtttgccgga tcaagagcta ccaactcttt ttccgaaggt aactggcttc agcagagcgc    4080
agataccaaa tactgtcctt ctagtgtagc cgtagttagg ccaccacttc aagaactctg    4140
tagcaccgcc tacatacctc gctctgctaa tcctgttacc agtggctgct gccagtggcg    4200
ataagtcgtg tcttaccggg ttggactcaa gacgatagtt accggataag gcgcagcggt    4260
cgggctgaac ggggggttcg tgcacacagc ccagcttgga gcgaacgacc tacaccgaac    4320
tgagatacct acagcgtgag ctatgagaaa gcgccacgct tcccgaaggg agaaaggcgg    4380
acaggtatcc ggtaagcggc agggtcggaa caggagagcg cacagaggga cttccagggg    4440
gaaacgcctg gtatctttat agtcctgtcg ggtttcgcca cctctgactt gagcgtcgat    4500
ttttgtgatg ctcgtcaggg gggcggagcc tatggaaaaa cgccagcaac gcggcctttt    4560
tacggttcct ggccttttgc tggccttttg ctcacatgtt ctttcctgcg ttatcccctg    4620
attctgtgga taaccgtatt accgcctttg agtgagctga taccgctcgc cgcagccgaa    4680
cgaccgagcg cagcgagtca gtgagcgagg aagcggaaga gcgcctgatg cggtattttc    4740
tccttacgca tctgtgcggt atttcacacc gcatatatgg tgcactctca gtacaatctg    4800
ctctgatgcc gcatagttaa gccagtatac actccgctat cgctacgtga ctgggtcatg    4860
gctgcgcccc gacacccgcc aacacccgct gacgcgccct gacgggcttg tctgctcccg    4920
gcatccgctt acagacaagc tgtgaccgtc tccgggagct gcatgtgtca gaggttttca    4980
ccgtcatcac cgaaacgcgc gaggcagcag atcaattcgc gcgcgaaggc gaagcggcat    5040
gcataatgtg cctgtcaaat ggacgaagca gggattctgc aaaccctatg ctactccgtc    5100
aagccgtcaa ttgtctgatt cgttaccaat tatgacaact tgacggctac atcattcact    5160
ttttcttcac aaccggcacg gaactcgctc gggctggccc cggtgcattt tttaaatacc    5220
cgcgagaaat agagttgatc gtcaaaacca acattgcgac cgacggtggc gataggcatc    5280
cgggtggtgc tcaaaagcag cttcgcctgg ctgatacgtt ggtcctcgcg ccagcttaag    5340
```

-continued

```
acgctaatcc ctaactgctg gcggaaaaga tgtgacagac gcgacggcga caagcaaaca      5400
tgctgtgcga cgctggcgat atcaaaattg ctgtctgcca ggtgatcgct gatgtactga      5460
caagcctcgc gtacccgatt atccatcggt ggatggagcg actcgttaat cgcttccatg      5520
cgccgcagta acaattgctc aagcagattt atcgccagca gctccgaata gcgcccttcc      5580
ccttgcccgg cgttaatgat ttgcccaaac aggtcgctga atgcggctg gtgcgcttca       5640 tccgggcgaa agaaccccgt attggcaaat attgacggcc agttaagcca ttcatgccag      5700
taggcgcgcg gacgaaagta aacccactgg tgataccatt cgcgagcctc cggatgacga      5760
ccgtagtgat gaatctctcc tggcgggaac agcaaaatat cacccggtcg gcaaacaaat      5820
tctcgtccct gattttcac cacccctga ccgcgaatgg tgagattgag aatataacct        5880
ttcattccca gcggtcggtc gataaaaaaa tcgagataac cgttggcctc aatcggcgtt      5940
aaacccgcca ccagatgggc attaaacgag tatcccggca gcagggggatc attttgcgct     6000 tcagccatac ttttcatact cccgccattc agag                                   6034
```

<210> SEQ ID NO 8
<211> LENGTH: 63
<212> TYPE: PRT
<213> ORGANISM: artificial sequence
<220> FEATURE:
<223> OTHER INFORMATION: synthetic construct

<400> SEQUENCE: 8

```
Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Arg Cys Gly Gln Gln Arg Phe Gln Trp Gln Phe Glu Gln Gln Pro Glu
        35                  40                  45

Cys Gly Gln Gln Arg Phe Gln Trp Gln Phe Glu Gln Gln Pro Cys
    50                  55                  60
```

<210> SEQ ID NO 9
<211> LENGTH: 576
<212> TYPE: DNA
<213> ORGANISM: artificial sequence
<220> FEATURE:
<223> OTHER INFORMATION: synthetic construct

<400> SEQUENCE: 9

```
gctagctgcg gtcaacaacg ttttcaatgg caattcgaac aacagccgcg ttgcggccag        60
caacgcttcc aatggcagtt tgaacagcaa ccgcgttgcg gtcagcaacg tttccagtgg      120
caatttgaac aacagccaga gtgcggccag cagcgctttc agtggcagtt cgagcagcag      180
ccgtgcggat cttgctgtcc gggctgttgc ggatccgatc catctgctca atctcaactg      240
cctgataaac attctggtct gcatgaacgc gctcctcaac gttacggtcc ggaggaggcg      300
gcgaagaaag aagaggcggc taaaaagccg gctcacatta ataagaccaa cccgcatcag      360
ggcaaccatc actccgaaaa gacccagcgt cagggctccg gtggcggcgg tagcggcagc      420
ggtggcggtg gttctgactc ccatcacaac catcacaagc aggactcccg ccctcagcac      480
cgtaagacgc caaacggcgg tgtgactct caccataacc accacaaaca ggactctcgc       540
ccgcagcacc gcaaaacccc taacggtaaa taataa                                 576
```

<210> SEQ ID NO 10
<211> LENGTH: 191
<212> TYPE: PRT

```
<213> ORGANISM: artificial sequence
<220> FEATURE:
<223> OTHER INFORMATION: synthetic construct

<400> SEQUENCE: 10

Met Ala Ser Cys Gly Gln Gln Arg Phe Gln Trp Gln Phe Glu Gln Gln
1               5                   10                  15

Pro Arg Cys Gly Gln Gln Arg Phe Gln Trp Gln Phe Glu Gln Gln Pro
            20                  25                  30

Arg Cys Gly Gln Gln Arg Phe Gln Trp Gln Phe Glu Gln Gln Pro Glu
        35                  40                  45

Cys Gly Gln Gln Arg Phe Gln Trp Gln Phe Glu Gln Gln Pro Cys Gly
    50                  55                  60

Ser Cys Cys Pro Gly Cys Cys Gly Ser Asp Pro Ser Ala Gln Ser Gln
65                  70                  75                  80

Leu Pro Asp Lys His Ser Gly Leu His Glu Arg Ala Pro Gln Arg Tyr
                85                  90                  95

Gly Pro Glu Glu Ala Ala Lys Lys Glu Ala Ala Lys Lys Pro Ala
            100                 105                 110

His Ile Asn Lys Thr Asn Pro His Gln Gly Asn His His Ser Glu Lys
            115                 120                 125

Thr Gln Arg Gln Gly Ser Gly Gly Gly Ser Gly Ser Gly Gly Gly
        130                 135                 140

Gly Ser Asp Ser His His Asn His Lys Gln Asp Ser Arg Pro Gln
145                 150                 155                 160

His Arg Lys Thr Pro Asn Gly Gly Asp Ser His His Asn His His
                165                 170                 175

Lys Gln Asp Ser Arg Pro Gln His Arg Lys Thr Pro Asn Gly Lys
            180                 185                 190

<210> SEQ ID NO 11
<211> LENGTH: 360
<212> TYPE: DNA
<213> ORGANISM: artificial sequence
<220> FEATURE:
<223> OTHER INFORMATION: synthetic construct

<400> SEQUENCE: 11
gatccatctg ctcaatctca actgcctgat aaacattctg gtctgcatga acgcgctcct    60
caacgttacg gtccggagga ggcggcgaag aaagaagagg cggctaaaaa gccggctcac   120
attaataaga ccaacccgca tcagggcaac catcactccg aaaagaccca gcgtcagggc   180
tccggtggcg gcggtagcgg cagcggtggc ggtggttctg actcccatca caaccatcac   240
aagcaggact cccgccctca gcaccgtaag acgccaaacg gcgtggtgac tctcaccat   300 aaccaccaca acaggactc tcgcccgcag caccgcaaaa ccctaacgg taaataataa    360

<210> SEQ ID NO 12
<211> LENGTH: 118
<212> TYPE: PRT
<213> ORGANISM: artificial sequence
<220> FEATURE:
<223> OTHER INFORMATION: synthetic construct

<400> SEQUENCE: 12

Asp Pro Ser Ala Gln Ser Gln Leu Pro Asp Lys His Ser Gly Leu His
1               5                   10                  15

Glu Arg Ala Pro Gln Arg Tyr Gly Pro Glu Glu Ala Ala Lys Lys Glu
            20                  25                  30
```

```
Glu Ala Ala Lys Lys Pro Ala His Ile Asn Lys Thr Asn Pro His Gln
         35                  40                  45
Gly Asn His His Ser Glu Lys Thr Gln Arg Gln Gly Ser Gly Gly Gly
 50                  55                  60
Gly Ser Gly Ser Gly Gly Gly Ser Asp Ser His His Asn His His
 65                  70                  75                  80
Lys Gln Asp Ser Arg Pro Gln His Arg Lys Thr Pro Asn Gly Gly
                 85                  90                  95
Asp Ser His His Asn His His Lys Gln Asp Ser Arg Pro Gln His Arg
                 100                 105                 110
Lys Thr Pro Asn Gly Lys
             115

<210> SEQ ID NO 13
<211> LENGTH: 28
<212> TYPE: DNA
<213> ORGANISM: artificial sequence
<220> FEATURE:
<223> OTHER INFORMATION: primer

<400> SEQUENCE: 13
ctggtccacc tacaacaaag ctctcatc                                    28

<210> SEQ ID NO 14
<211> LENGTH: 34
<212> TYPE: DNA
<213> ORGANISM: artificial sequence
<220> FEATURE:
<223> OTHER INFORMATION: primer

<400> SEQUENCE: 14
cttgtgcaat gtaacatcag agattttgag acac                             34

<210> SEQ ID NO 15
<211> LENGTH: 918
<212> TYPE: DNA
<213> ORGANISM: Escherichia coli

<400> SEQUENCE: 15
atgtctaaac gattaccacc gctaaatgcc ttacgagttt ttgatgccgc agcacgccat    60
ttaagtttca ctcgcgcagc agaagagctt tttgtgaccc aagccgcagt aagtcatcaa   120
atcaagtctc ttgaggattt tttggggcta aaactgttcc gccgccgtaa tcgttcactc   180
ctgctgaccg aggaagggca agctatttc ctcgatatca agagatatt ttcgcaatta    240
accgaagcga cgcgtaaact ccaggcccgt agcgccaagg gggcgttgac ggtcagttta   300
ctccccagtt cgccattca ttggttggtt ccgcgacttt ccagctttaa ttcagcttat   360
ccgggaattg acgttcgaat ccaggcggtt gatcgtcagg aagataagct ggcggatgat   420
gttgatgtgg cgatatttta tggtcggggc aactggccgg gctacgggt ggaaaaactg    480
tacgccgaat atttattgcc ggtgtgttcg ccgctactgc tgactggcga aaacccttg    540
aagacaccgg aagatctggc taaacatacg ttattacatg atgcttcgcg ccgtgactgg   600
cagacatata cccgacagtt ggggttaaat catatcaacg ttcagcaagg gccaattttt   660
agccatagcg ccatggtgct gcaagcggct atccacgggc agggagtggc gctgcaaat    720
aacgtgatgg cgcaatctga atcgaggcc ggacgtcttg tttgcccgtt taatgatgtt    780
ctggtcagta aaaatgcttt ttatctggtt tgtcatgaca gtcaggcaga actgggtaaa   840
atagccgcct ttcgccaatg gatcctggcg aaagccgctg ctgaacaaga aaaattccgc   900
```
tttcgttatg aacaataa                                                918

```
<210> SEQ ID NO 16
<211> LENGTH: 305
<212> TYPE: PRT
<213> ORGANISM: Escherichia coli

<400> SEQUENCE: 16
```

Met Ser Lys Arg Leu Pro Pro Leu Asn Ala Leu Arg Val Phe Asp Ala
1               5                   10                  15

Ala Ala Arg His Leu Ser Phe Thr Arg Ala Ala Glu Glu Leu Phe Val
            20                  25                  30

Thr Gln Ala Ala Val Ser His Gln Ile Lys Ser Leu Glu Asp Phe Leu
        35                  40                  45

Gly Leu Lys Leu Phe Arg Arg Asn Arg Ser Leu Leu Leu Thr Glu
    50                  55                  60

Glu Gly Gln Ser Tyr Phe Leu Asp Ile Lys Glu Ile Phe Ser Gln Leu
65                  70                  75                  80

Thr Glu Ala Thr Arg Lys Leu Gln Ala Arg Ser Ala Lys Gly Ala Leu
                85                  90                  95

Thr Val Ser Leu Leu Pro Ser Phe Ala Ile His Trp Leu Val Pro Arg
            100                 105                 110

Leu Ser Ser Phe Asn Ser Ala Tyr Pro Gly Ile Asp Val Arg Ile Gln
        115                 120                 125

Ala Val Asp Arg Gln Glu Asp Lys Leu Ala Asp Asp Val Asp Val Ala
    130                 135                 140

Ile Phe Tyr Gly Arg Gly Asn Trp Pro Gly Leu Arg Val Glu Lys Leu
145                 150                 155                 160

Tyr Ala Glu Tyr Leu Leu Pro Val Cys Ser Pro Leu Leu Leu Thr Gly
                165                 170                 175

Glu Lys Pro Leu Lys Thr Pro Glu Asp Leu Ala Lys His Thr Leu Leu
            180                 185                 190

His Asp Ala Ser Arg Arg Asp Trp Gln Thr Tyr Thr Arg Gln Leu Gly
        195                 200                 205

Leu Asn His Ile Asn Val Gln Gln Gly Pro Ile Phe Ser His Ser Ala
    210                 215                 220

Met Val Leu Gln Ala Ala Ile His Gly Gln Gly Val Ala Leu Ala Asn
225                 230                 235                 240

Asn Val Met Ala Gln Ser Glu Ile Glu Ala Gly Arg Leu Val Cys Pro
                245                 250                 255

Phe Asn Asp Val Leu Val Ser Lys Asn Ala Phe Tyr Leu Val Cys His
            260                 265                 270

Asp Ser Gln Ala Glu Leu Gly Lys Ile Ala Ala Phe Arg Gln Trp Ile
        275                 280                 285

Leu Ala Lys Ala Ala Ala Glu Gln Glu Lys Phe Arg Phe Arg Tyr Glu
    290                 295                 300

Gln
305

```
<210> SEQ ID NO 17
<211> LENGTH: 567
<212> TYPE: DNA
<213> ORGANISM: Escherichia coli

<400> SEQUENCE: 17
```
atggtcaaat ctcaaccgat tttgagatat atcttgcgcg ggattccgc gattgcagta    60

```
gcggttctgc tttctgcatg tagtgcaaat aacaccgcaa agaatatgca tcctgagaca      120
cgtgcagtgg gtagtgaaac atcatcactg caagcttctc aggatgaatt tgaaaacctg      180
gttcgtaatg tcgacgtaaa atcgcgaatt atggatcagt atgctgactg gaaaggcgta      240
cgttatcgtc tgggcggcag cactaaaaaa ggtatcgatt gttctggttt cgtacagcgt      300
acattccgtg agcaatttgg cttagaactt ccgcgttcga cttacgaaca gcaggaaatg      360
ggtaaatctg tttcccgcag taatttgcgt acgggtgatt tagttctgtt ccgtgccggt      420
tcaacgggac gccatgtcgg tatttatatc ggcaacaatc agtttgtcca tgcttccacc      480
agcagtggtg ttattatttc cagcatgaat gaaccgtact ggaagaagcg ttacaacgaa      540
gcacgccggg ttctcagccg cagctaa                                         567
```

<210> SEQ ID NO 18
<211> LENGTH: 188
<212> TYPE: PRT
<213> ORGANISM: Escherichia coli

<400> SEQUENCE: 18

Met Val Lys Ser Gln Pro Ile Leu Arg Tyr Ile Leu Arg Gly Ile Pro
1               5                   10                  15

Ala Ile Ala Val Ala Val Leu Leu Ser Ala Cys Ser Ala Asn Asn Thr
            20                  25                  30

Ala Lys Asn Met His Pro Glu Thr Arg Ala Val Gly Ser Glu Thr Ser
        35                  40                  45

Ser Leu Gln Ala Ser Gln Asp Glu Phe Glu Asn Leu Val Arg Asn Val
    50                  55                  60

Asp Val Lys Ser Arg Ile Met Asp Gln Tyr Ala Asp Trp Lys Gly Val
65                  70                  75                  80

Arg Tyr Arg Leu Gly Gly Ser Thr Lys Lys Gly Ile Asp Cys Ser Gly
                85                  90                  95

Phe Val Gln Arg Thr Phe Arg Glu Gln Phe Gly Leu Glu Leu Pro Arg
            100                 105                 110

Ser Thr Tyr Glu Gln Gln Glu Met Gly Lys Ser Val Ser Arg Ser Asn
        115                 120                 125

Leu Arg Thr Gly Asp Leu Val Leu Phe Arg Ala Gly Ser Thr Gly Arg
    130                 135                 140

His Val Gly Ile Tyr Ile Gly Asn Asn Gln Phe Val His Ala Ser Thr
145                 150                 155                 160

Ser Ser Gly Val Ile Ile Ser Ser Met Asn Glu Pro Tyr Trp Lys Lys
                165                 170                 175

Arg Tyr Asn Glu Ala Arg Arg Val Leu Ser Arg Ser
            180                 185

<210> SEQ ID NO 19
<211> LENGTH: 16
<212> TYPE: PRT
<213> ORGANISM: artificial sequence
<220> FEATURE:
<223> OTHER INFORMATION: synthetic construct peptide linker

<400> SEQUENCE: 19

Gly Pro Glu Glu Ala Ala Lys Lys Glu Glu Ala Ala Lys Lys Pro Ala
1               5                   10                  15

<210> SEQ ID NO 20
<211> LENGTH: 100
<212> TYPE: DNA
<213> ORGANISM: Escherichia coli

<400> SEQUENCE: 20

```
tttttatcca taagattagc ggatcctacc tgacgctttt tatcgcaact ctctactgtt    60
tctccatacc cgttttttgg gctaacagga ggaattaacc                         100
```

<210> SEQ ID NO 21
<211> LENGTH: 591
<212> TYPE: DNA
<213> ORGANISM: Escherichia coli

<400> SEQUENCE: 21

```
atgaaagtag caaaagacct ggtggtcagc ctggcctatc aggtacgtac agaagacggt    60
gtgttggttg atgagtctcc ggtgagtgcg ccgctggact acctgcatgg tcacggttcc   120
ctgatctctg gcctggaaac ggcgctggaa ggtcatgaag ttggcgacaa atttgatgtc   180
gctgttggcg cgaacgacgc ttacggtcag tacgacgaaa acctggtgca acgtgttcct   240
aaagacgtat ttatgggcgt tgatgaactg caggtaggta tgcgtttcct ggctgaaacc   300
gaccagggtc cggtaccggt tgaaatcact gcggttgaag acgatcacgt cgtggttgat   360
ggtaaccaca tgctggccgg tcagaacctg aaattcaacg ttgaagttgt ggcgattcgc   420
gaagcgactg aagaagaact ggctcatggt cacgttcacg gcgcgcacga tcaccaccac   480
gatcacgacc acgacggttg ctgcggcggt catggccacg atcacggtca tgaacacggt   540
ggcgaaggct gctgtggcgg taaaggcaac ggcggttgcg gttgccacta a             591
```

<210> SEQ ID NO 22
<211> LENGTH: 196
<212> TYPE: PRT
<213> ORGANISM: Escherichia coli

<400> SEQUENCE: 22

```
Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Cys Cys Gly Gly His Gly His Asp His Gly
                165                 170                 175

His Glu His Gly Gly Glu Gly Cys Cys Gly Gly Lys Gly Asn Gly Gly
            180                 185                 190

Cys Gly Cys His
```

-continued

```
                195

<210> SEQ ID NO 23
<211> LENGTH: 8
<212> TYPE: PRT
<213> ORGANISM: Artificial Sequence
<220> FEATURE:
<223> OTHER INFORMATION: Caspase 3 cleavage site

<400> SEQUENCE: 23

Leu Glu Ser Gly Asp Glu Val Asp
1               5

<210> SEQ ID NO 24
<211> LENGTH: 12
<212> TYPE: PRT
<213> ORGANISM: artificial sequence
<220> FEATURE:
<223> OTHER INFORMATION: Synthetic construct

<400> SEQUENCE: 24

Arg Val Pro Asn Lys Thr Val Thr Val Asp Gly Ala
1               5                   10

<210> SEQ ID NO 25
<211> LENGTH: 12
<212> TYPE: PRT
<213> ORGANISM: artificial sequence
<220> FEATURE:
<223> OTHER INFORMATION: Synthetic construct

<400> SEQUENCE: 25

Asp Arg His Lys Ser Lys Tyr Ser Ser Thr Lys Ser
1               5                   10

<210> SEQ ID NO 26
<211> LENGTH: 12
<212> TYPE: PRT
<213> ORGANISM: artificial sequence
<220> FEATURE:
<223> OTHER INFORMATION: Synthetic construct

<400> SEQUENCE: 26

Lys Asn Phe Pro Gln Gln Lys Glu Phe Pro Leu Ser
1               5                   10

<210> SEQ ID NO 27
<211> LENGTH: 12
<212> TYPE: PRT
<213> ORGANISM: artificial sequence
<220> FEATURE:
<223> OTHER INFORMATION: Synthetic construct

<400> SEQUENCE: 27

Gln Arg Asn Ser Pro Ala Met Ser Arg Arg Asp
1               5                   10

<210> SEQ ID NO 28
<211> LENGTH: 12
<212> TYPE: PRT
<213> ORGANISM: artificial sequence
<220> FEATURE:
<223> OTHER INFORMATION: Synthetic construct

<400> SEQUENCE: 28

Thr Arg Lys Pro Asn Met Pro His Gly Gln Tyr Leu
1               5                   10
```

```
<210> SEQ ID NO 29
<211> LENGTH: 12
<212> TYPE: PRT
<213> ORGANISM: artificial sequence
<220> FEATURE:
<223> OTHER INFORMATION: Synthetic construct

<400> SEQUENCE: 29

Lys Pro Pro His Leu Ala Lys Leu Pro Phe Thr Thr
1               5                   10

<210> SEQ ID NO 30
<211> LENGTH: 12
<212> TYPE: PRT
<213> ORGANISM: artificial sequence
<220> FEATURE:
<223> OTHER INFORMATION: Synthetic construct

<400> SEQUENCE: 30

Asn Lys Arg Pro Pro Thr Ser His Arg Ile His Ala
1               5                   10

<210> SEQ ID NO 31
<211> LENGTH: 12
<212> TYPE: PRT
<213> ORGANISM: artificial sequence
<220> FEATURE:
<223> OTHER INFORMATION: Synthetic construct

<400> SEQUENCE: 31

Asn Leu Pro Arg Tyr Gln Pro Pro Cys Lys Pro Leu
1               5                   10

<210> SEQ ID NO 32
<211> LENGTH: 12
<212> TYPE: PRT
<213> ORGANISM: artificial sequence
<220> FEATURE:
<223> OTHER INFORMATION: Synthetic construct

<400> SEQUENCE: 32

Arg Pro Pro Trp Lys Lys Pro Ile Pro Pro Ser Glu
1               5                   10

<210> SEQ ID NO 33
<211> LENGTH: 12
<212> TYPE: PRT
<213> ORGANISM: artificial sequence
<220> FEATURE:
<223> OTHER INFORMATION: Synthetic construct

<400> SEQUENCE: 33

Arg Gln Arg Pro Lys Asp His Phe Phe Ser Arg Pro
1               5                   10

<210> SEQ ID NO 34
<211> LENGTH: 12
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa = Thr or Pro
<220> FEATURE:
<221> NAME/KEY: MISC_FEATURE
<222> LOCATION: (12)..(12)
<223> OTHER INFORMATION: Xaa = Thr or Pro
```

-continued

```
<400> SEQUENCE: 34

Ser Val Pro Asn Lys Xaa Val Thr Val Asp Gly Xaa
1               5                   10

<210> SEQ ID NO 35
<211> LENGTH: 12
<212> TYPE: PRT
<213> ORGANISM: artificial sequence
<220> FEATURE:
<223> OTHER INFORMATION: Synthetic construct

<400> SEQUENCE: 35

Thr Thr Lys Trp Arg His Arg Ala Pro Val Ser Pro
1               5                   10

<210> SEQ ID NO 36
<211> LENGTH: 12
<212> TYPE: PRT
<213> ORGANISM: artificial sequence
<220> FEATURE:
<223> OTHER INFORMATION: Synthetic construct

<400> SEQUENCE: 36

Trp Leu Gly Lys Asn Arg Ile Lys Pro Arg Ala Ser
1               5                   10

<210> SEQ ID NO 37
<211> LENGTH: 12
<212> TYPE: PRT
<213> ORGANISM: artificial sequence
<220> FEATURE:
<223> OTHER INFORMATION: Synthetic construct

<400> SEQUENCE: 37

Ser Asn Phe Lys Thr Pro Leu Pro Leu Thr Gln Ser
1               5                   10

<210> SEQ ID NO 38
<211> LENGTH: 12
<212> TYPE: PRT
<213> ORGANISM: artificial sequence
<220> FEATURE:
<223> OTHER INFORMATION: Synthetic construct

<400> SEQUENCE: 38

Ser Val Ser Val Gly Met Lys Pro Ser Pro Arg Pro
1               5                   10

<210> SEQ ID NO 39
<211> LENGTH: 7
<212> TYPE: PRT
<213> ORGANISM: artificial sequence
<220> FEATURE:
<223> OTHER INFORMATION: Synthetic construct

<400> SEQUENCE: 39

Asp Leu His Thr Val Tyr His
1               5

<210> SEQ ID NO 40
<211> LENGTH: 7
<212> TYPE: PRT
<213> ORGANISM: artificial sequence
<220> FEATURE:
<223> OTHER INFORMATION: Synthetic construct

<400> SEQUENCE: 40
```

His Ile Lys Pro Pro Thr Arg
1               5

<210> SEQ ID NO 41
<211> LENGTH: 7
<212> TYPE: PRT
<213> ORGANISM: artificial sequence
<220> FEATURE:
<223> OTHER INFORMATION: Synthetic construct

<400> SEQUENCE: 41

His Pro Val Trp Pro Ala Ile
1               5

<210> SEQ ID NO 42
<211> LENGTH: 7
<212> TYPE: PRT
<213> ORGANISM: artificial sequence
<220> FEATURE:
<223> OTHER INFORMATION: Synthetic construct

<400> SEQUENCE: 42

Met Pro Leu Tyr Tyr Leu Gln
1               5

<210> SEQ ID NO 43
<211> LENGTH: 26
<212> TYPE: PRT
<213> ORGANISM: artificial sequence
<220> FEATURE:
<223> OTHER INFORMATION: Synthetic construct

<400> SEQUENCE: 43

His Leu Thr Val Pro Trp Arg Gly Gly Gly Ser Ala Val Pro Phe Tyr
1               5                   10                  15

Ser His Ser Gln Ile Thr Leu Pro Asn His
            20                  25

<210> SEQ ID NO 44
<211> LENGTH: 41
<212> TYPE: PRT
<213> ORGANISM: artificial sequence
<220> FEATURE:
<223> OTHER INFORMATION: Synthetic construct

<400> SEQUENCE: 44

Gly Pro His Asp Thr Ser Ser Gly Gly Val Arg Pro Asn Leu His His
1               5                   10                  15

Thr Ser Lys Lys Glu Lys Arg Glu Asn Arg Lys Val Pro Phe Tyr Ser
            20                  25                  30

His Ser Val Thr Ser Arg Gly Asn Val
        35                  40

<210> SEQ ID NO 45
<211> LENGTH: 7
<212> TYPE: PRT
<213> ORGANISM: artificial sequence
<220> FEATURE:
<223> OTHER INFORMATION: Synthetic construct

<400> SEQUENCE: 45

Lys His Pro Thr Tyr Arg Gln
1               5

<210> SEQ ID NO 46

```
<211> LENGTH: 7
<212> TYPE: PRT
<213> ORGANISM: artificial sequence
<220> FEATURE:
<223> OTHER INFORMATION: Synthetic construct

<400> SEQUENCE: 46

His Pro Met Ser Ala Pro Arg
1               5

<210> SEQ ID NO 47
<211> LENGTH: 7
<212> TYPE: PRT
<213> ORGANISM: artificial sequence
<220> FEATURE:
<223> OTHER INFORMATION: Synthetic construct

<400> SEQUENCE: 47

Met Pro Lys Tyr Tyr Leu Gln
1               5

<210> SEQ ID NO 48
<211> LENGTH: 7
<212> TYPE: PRT
<213> ORGANISM: artificial sequence
<220> FEATURE:
<223> OTHER INFORMATION: Synthetic construct

<400> SEQUENCE: 48

Met His Ala His Ser Ile Ala
1               5

<210> SEQ ID NO 49
<211> LENGTH: 12
<212> TYPE: PRT
<213> ORGANISM: artificial sequence
<220> FEATURE:
<223> OTHER INFORMATION: Synthetic construct

<400> SEQUENCE: 49

Ala Lys Pro Ile Ser Gln His Leu Gln Arg Gly Ser
1               5                   10

<210> SEQ ID NO 50
<211> LENGTH: 12
<212> TYPE: PRT
<213> ORGANISM: artificial sequence
<220> FEATURE:
<223> OTHER INFORMATION: Synthetic construct

<400> SEQUENCE: 50

Ala Pro Pro Thr Pro Ala Ala Ala Ser Ala Thr Thr
1               5                   10

<210> SEQ ID NO 51
<211> LENGTH: 12
<212> TYPE: PRT
<213> ORGANISM: artificial sequence
<220> FEATURE:
<223> OTHER INFORMATION: Synthetic construct

<400> SEQUENCE: 51

Asp Pro Thr Glu Gly Ala Arg Arg Thr Ile Met Thr
1               5                   10

<210> SEQ ID NO 52
<211> LENGTH: 12
<212> TYPE: PRT
```

```
-continued

<213> ORGANISM: artificial sequence
<220> FEATURE:
<223> OTHER INFORMATION: Synthetic construct

<400> SEQUENCE: 52

Leu Asp Thr Ser Phe Pro Pro Val Pro Phe His Ala
1               5                   10

<210> SEQ ID NO 53
<211> LENGTH: 12
<212> TYPE: PRT
<213> ORGANISM: artificial sequence
<220> FEATURE:
<223> OTHER INFORMATION: Synthetic construct

<400> SEQUENCE: 53

Leu Asp Thr Ser Phe His Gln Val Pro Phe His Gln
1               5                   10

<210> SEQ ID NO 54
<211> LENGTH: 11
<212> TYPE: PRT
<213> ORGANISM: artificial sequence
<220> FEATURE:
<223> OTHER INFORMATION: Synthetic construct

<400> SEQUENCE: 54

Leu Pro Arg Ile Ala Asn Thr Trp Ser Pro Ser
1               5                   10

<210> SEQ ID NO 55
<211> LENGTH: 12
<212> TYPE: PRT
<213> ORGANISM: artificial sequence
<220> FEATURE:
<223> OTHER INFORMATION: Synthetic construct

<400> SEQUENCE: 55

Arg Thr Asn Ala Ala Asp His Pro Ala Ala Val Thr
1               5                   10

<210> SEQ ID NO 56
<211> LENGTH: 12
<212> TYPE: PRT
<213> ORGANISM: artificial sequence
<220> FEATURE:
<223> OTHER INFORMATION: Synthetic construct

<400> SEQUENCE: 56

Ser Leu Asn Trp Val Thr Ile Pro Gly Pro Lys Ile
1               5                   10

<210> SEQ ID NO 57
<211> LENGTH: 12
<212> TYPE: PRT
<213> ORGANISM: artificial sequence
<220> FEATURE:
<223> OTHER INFORMATION: Synthetic construct

<400> SEQUENCE: 57

Thr Asp Met Gln Ala Pro Thr Lys Ser Tyr Ser Asn
1               5                   10

<210> SEQ ID NO 58
<211> LENGTH: 12
<212> TYPE: PRT
<213> ORGANISM: artificial sequence
<220> FEATURE:
```

<223> OTHER INFORMATION: Synthetic construct

<400> SEQUENCE: 58

Thr Ile Met Thr Lys Ser Pro Ser Leu Ser Cys Gly
1               5                   10

<210> SEQ ID NO 59
<211> LENGTH: 12
<212> TYPE: PRT
<213> ORGANISM: artificial sequence
<220> FEATURE:
<223> OTHER INFORMATION: Synthetic construct

<400> SEQUENCE: 59

Thr Pro Ala Leu Asp Gly Leu Arg Gln Pro Leu Arg
1               5                   10

<210> SEQ ID NO 60
<211> LENGTH: 12
<212> TYPE: PRT
<213> ORGANISM: artificial sequence
<220> FEATURE:
<223> OTHER INFORMATION: Synthetic construct

<400> SEQUENCE: 60

Thr Tyr Pro Ala Ser Arg Leu Pro Leu Leu Ala Pro
1               5                   10

<210> SEQ ID NO 61
<211> LENGTH: 12
<212> TYPE: PRT
<213> ORGANISM: artificial sequence
<220> FEATURE:
<223> OTHER INFORMATION: Synthetic construct

<400> SEQUENCE: 61

Ala Lys Thr His Lys His Pro Ala Pro Ser Tyr Ser
1               5                   10

<210> SEQ ID NO 62
<211> LENGTH: 12
<212> TYPE: PRT
<213> ORGANISM: artificial sequence
<220> FEATURE:
<223> OTHER INFORMATION: Synthetic construct

<400> SEQUENCE: 62

Thr Asp Pro Thr Pro Phe Ser Ile Ser Pro Glu Arg
1               5                   10

<210> SEQ ID NO 63
<211> LENGTH: 12
<212> TYPE: PRT
<213> ORGANISM: artificial sequence
<220> FEATURE:
<223> OTHER INFORMATION: Synthetic construct

<400> SEQUENCE: 63

Ser Gln Asn Trp Gln Asp Ser Thr Ser Tyr Ser Asn
1               5                   10

<210> SEQ ID NO 64
<211> LENGTH: 12
<212> TYPE: PRT
<213> ORGANISM: artificial sequence
<220> FEATURE:
<223> OTHER INFORMATION: Synthetic construct

```
<400> SEQUENCE: 64

Trp His Asp Lys Pro Gln Asn Ser Ser Lys Ser Thr
1               5                   10

<210> SEQ ID NO 65
<211> LENGTH: 12
<212> TYPE: PRT
<213> ORGANISM: artificial sequence
<220> FEATURE:
<223> OTHER INFORMATION: Synthetic construct

<400> SEQUENCE: 65

Leu Asp Val Glu Ser Tyr Lys Gly Thr Ser Met Pro
1               5                   10

<210> SEQ ID NO 66
<211> LENGTH: 7
<212> TYPE: PRT
<213> ORGANISM: artificial sequence
<220> FEATURE:
<223> OTHER INFORMATION: Synthetic construct

<400> SEQUENCE: 66

Asn Thr Pro Lys Glu Asn Trp
1               5

<210> SEQ ID NO 67
<211> LENGTH: 7
<212> TYPE: PRT
<213> ORGANISM: artificial sequence
<220> FEATURE:
<223> OTHER INFORMATION: Synthetic construct

<400> SEQUENCE: 67

Asn Thr Pro Ala Ser Asn Arg
1               5

<210> SEQ ID NO 68
<211> LENGTH: 7
<212> TYPE: PRT
<213> ORGANISM: artificial sequence
<220> FEATURE:
<223> OTHER INFORMATION: Synthetic construct

<400> SEQUENCE: 68

Pro Arg Gly Met Leu Ser Thr
1               5

<210> SEQ ID NO 69
<211> LENGTH: 7
<212> TYPE: PRT
<213> ORGANISM: artificial sequence
<220> FEATURE:
<223> OTHER INFORMATION: Synthetic construct

<400> SEQUENCE: 69

Pro Pro Thr Tyr Leu Ser Thr
1               5

<210> SEQ ID NO 70
<211> LENGTH: 12
<212> TYPE: PRT
<213> ORGANISM: artificial sequence
<220> FEATURE:
<223> OTHER INFORMATION: Synthetic construct

<400> SEQUENCE: 70
```

```
Thr Ile Pro Thr His Arg Gln His Asp Tyr Arg Ser
1               5                   10

<210> SEQ ID NO 71
<211> LENGTH: 7
<212> TYPE: PRT
<213> ORGANISM: artificial sequence
<220> FEATURE:
<223> OTHER INFORMATION: Synthetic construct

<400> SEQUENCE: 71

Thr Pro Pro Thr His Arg Leu
1               5

<210> SEQ ID NO 72
<211> LENGTH: 7
<212> TYPE: PRT
<213> ORGANISM: artificial sequence
<220> FEATURE:
<223> OTHER INFORMATION: Synthetic construct

<400> SEQUENCE: 72

Leu Pro Thr Met Ser Thr Pro
1               5

<210> SEQ ID NO 73
<211> LENGTH: 7
<212> TYPE: PRT
<213> ORGANISM: artificial sequence
<220> FEATURE:
<223> OTHER INFORMATION: Synthetic construct

<400> SEQUENCE: 73

Leu Gly Thr Asn Ser Thr Pro
1               5

<210> SEQ ID NO 74
<211> LENGTH: 12
<212> TYPE: PRT
<213> ORGANISM: artificial sequence
<220> FEATURE:
<223> OTHER INFORMATION: Synthetic construct

<400> SEQUENCE: 74

Thr Pro Leu Thr Gly Ser Thr Asn Leu Leu Ser Ser
1               5                   10

<210> SEQ ID NO 75
<211> LENGTH: 7
<212> TYPE: PRT
<213> ORGANISM: artificial sequence
<220> FEATURE:
<223> OTHER INFORMATION: Synthetic construct

<400> SEQUENCE: 75

Thr Pro Leu Thr Lys Glu Thr
1               5

<210> SEQ ID NO 76
<211> LENGTH: 7
<212> TYPE: PRT
<213> ORGANISM: artificial sequence
<220> FEATURE:
<223> OTHER INFORMATION: Synthetic construct

<400> SEQUENCE: 76

Lys Gln Ser His Asn Pro Pro
1               5
```

<210> SEQ ID NO 77
<211> LENGTH: 7
<212> TYPE: PRT
<213> ORGANISM: artificial sequence
<220> FEATURE:
<223> OTHER INFORMATION: Synthetic construct

<400> SEQUENCE: 77

Gln Gln Ser His Asn Pro Pro
1               5

<210> SEQ ID NO 78
<211> LENGTH: 7
<212> TYPE: PRT
<213> ORGANISM: artificial sequence
<220> FEATURE:
<223> OTHER INFORMATION: Synthetic construct

<400> SEQUENCE: 78

Thr Gln Pro His Asn Pro Pro
1               5

<210> SEQ ID NO 79
<211> LENGTH: 12
<212> TYPE: PRT
<213> ORGANISM: artificial sequence
<220> FEATURE:
<223> OTHER INFORMATION: Synthetic construct

<400> SEQUENCE: 79

Ser Thr Asn Leu Leu Arg Thr Ser Thr Val His Pro
1               5                   10

<210> SEQ ID NO 80
<211> LENGTH: 12
<212> TYPE: PRT
<213> ORGANISM: artificial sequence
<220> FEATURE:
<223> OTHER INFORMATION: Synthetic construct

<400> SEQUENCE: 80

His Thr Gln Pro Ser Tyr Ser Ser Thr Asn Leu Phe
1               5                   10

<210> SEQ ID NO 81
<211> LENGTH: 7
<212> TYPE: PRT
<213> ORGANISM: artificial sequence
<220> FEATURE:
<223> OTHER INFORMATION: Synthetic construct

<400> SEQUENCE: 81

Ser Leu Leu Ser Ser His Ala
1               5

<210> SEQ ID NO 82
<211> LENGTH: 12
<212> TYPE: PRT
<213> ORGANISM: artificial sequence
<220> FEATURE:
<223> OTHER INFORMATION: Synthetic construct

<400> SEQUENCE: 82

Gln Gln Ser Ser Ile Ser Leu Ser Ser His Ala Val
1               5                   10

```
<210> SEQ ID NO 83
<211> LENGTH: 7
<212> TYPE: PRT
<213> ORGANISM: artificial sequence
<220> FEATURE:
<223> OTHER INFORMATION: Synthetic construct

<400> SEQUENCE: 83

Asn Ala Ser Pro Ser Ser Leu
1               5

<210> SEQ ID NO 84
<211> LENGTH: 7
<212> TYPE: PRT
<213> ORGANISM: artificial sequence
<220> FEATURE:
<223> OTHER INFORMATION: Synthetic construct

<400> SEQUENCE: 84

His Ser Pro Ser Ser Leu Arg
1               5

<210> SEQ ID NO 85
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X= H, R or N
<220> FEATURE:
<221> NAME/KEY: MISC_FEATURE
<222> LOCATION: (2)..(2)
<223> OTHER INFORMATION: X= His, Arg or Asn

<400> SEQUENCE: 85

Lys Xaa Ser His His Thr His
1               5

<210> SEQ ID NO 86
<211> LENGTH: 7
<212> TYPE: PRT
<213> ORGANISM: artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: X = H, R or N
<220> FEATURE:
<221> NAME/KEY: MISC_FEATURE
<222> LOCATION: (2)..(2)
<223> OTHER INFORMATION: X = His, Arg or Asn

<400> SEQUENCE: 86

Glu Xaa Ser His His Thr His
1               5

<210> SEQ ID NO 87
<211> LENGTH: 12
<212> TYPE: PRT
<213> ORGANISM: artificial sequence
<220> FEATURE:
<223> OTHER INFORMATION: Synthetic construct

<400> SEQUENCE: 87

Ser His His Thr His Tyr Gly Gln Pro Gly Pro Val
1               5                   10
```

```
<210> SEQ ID NO 88
<211> LENGTH: 7
<212> TYPE: PRT
<213> ORGANISM: artificial sequence
<220> FEATURE:
<223> OTHER INFORMATION: Synthetic construct

<400> SEQUENCE: 88

Leu Glu Ser Thr Ser Leu Leu
1               5

<210> SEQ ID NO 89
<211> LENGTH: 7
<212> TYPE: PRT
<213> ORGANISM: artificial sequence
<220> FEATURE:
<223> OTHER INFORMATION: Synthetic construct

<400> SEQUENCE: 89

Asp Leu Thr Leu Pro Phe His
1               5

<210> SEQ ID NO 90
<211> LENGTH: 8
<212> TYPE: PRT
<213> ORGANISM: artificial sequence
<220> FEATURE:
<223> OTHER INFORMATION: Synthetic construct

<400> SEQUENCE: 90

Arg Thr Asn Ala Ala Asp His Pro
1               5

<210> SEQ ID NO 91
<211> LENGTH: 12
<212> TYPE: PRT
<213> ORGANISM: artificial sequence
<220> FEATURE:
<223> OTHER INFORMATION: Synthetic construct

<400> SEQUENCE: 91

Ile Pro Trp Trp Asn Ile Arg Ala Pro Leu Asn Ala
1               5                   10

<210> SEQ ID NO 92
<211> LENGTH: 18
<212> TYPE: PRT
<213> ORGANISM: artificial sequence
<220> FEATURE:
<223> OTHER INFORMATION: Synthetic construct

<400> SEQUENCE: 92

Glu Gln Ile Ser Gly Ser Leu Val Ala Ala Pro Trp Glu Gly Glu Gly
1               5                   10                  15

Glu Arg

<210> SEQ ID NO 93
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 93

Thr Pro Pro Glu Leu Leu His Gly Ala Pro Arg Ser
1               5                   10
```

<210> SEQ ID NO 94
<211> LENGTH: 18
<212> TYPE: PRT
<213> ORGANISM: artificial sequence
<220> FEATURE:
<223> OTHER INFORMATION: Synthetic construct

<400> SEQUENCE: 94

Leu Asp Thr Ser Phe His Gln Val Pro Phe His Gln Lys Arg Lys Arg
1               5                   10                  15

Lys Asp

<210> SEQ ID NO 95
<211> LENGTH: 18
<212> TYPE: PRT
<213> ORGANISM: artificial sequence
<220> FEATURE:
<223> OTHER INFORMATION: Synthetic construct

<400> SEQUENCE: 95

Glu Gln Ile Ser Gly Ser Leu Val Ala Ala Pro Trp Lys Arg Lys Arg
1               5                   10                  15

Lys Asp

<210> SEQ ID NO 96
<211> LENGTH: 18
<212> TYPE: PRT
<213> ORGANISM: artificial sequence
<220> FEATURE:
<223> OTHER INFORMATION: Synthetic construct

<400> SEQUENCE: 96

Thr Pro Pro Glu Leu Leu His Gly Asp Pro Arg Ser Lys Arg Lys Arg
1               5                   10                  15

Lys Asp

<210> SEQ ID NO 97
<211> LENGTH: 13
<212> TYPE: PRT
<213> ORGANISM: artificial sequence
<220> FEATURE:
<223> OTHER INFORMATION: Synthetic construct

<400> SEQUENCE: 97

Asn Thr Ser Gln Leu Ser Thr Glu Gly Glu Gly Glu Asp
1               5                   10

<210> SEQ ID NO 98
<211> LENGTH: 13
<212> TYPE: PRT
<213> ORGANISM: artificial sequence
<220> FEATURE:
<223> OTHER INFORMATION: Synthetic construct

<400> SEQUENCE: 98

Thr Pro Pro Glu Leu Leu His Gly Asp Pro Arg Ser Cys
1               5                   10

<210> SEQ ID NO 99
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 99

```
His Ile Asn Lys Thr Asn Pro His Gln Gly Asn His His Ser Glu Lys
1               5                   10                  15

Thr Gln Arg Gln
            20

<210> SEQ ID NO 100
<211> LENGTH: 15
<212> TYPE: PRT
<213> ORGANISM: artificial sequence
<220> FEATURE:
<223> OTHER INFORMATION: Synthetic construct

<400> SEQUENCE: 100

His Ala His Lys Asn Gln Lys Glu Thr His Gln Arg His Ala Ala
1               5                   10                  15

<210> SEQ ID NO 101
<211> LENGTH: 15
<212> TYPE: PRT
<213> ORGANISM: artificial sequence
<220> FEATURE:
<223> OTHER INFORMATION: Synthetic construct

<400> SEQUENCE: 101

His Glu His Lys Asn Gln Lys Glu Thr His Gln Arg His Ala Ala
1               5                   10                  15

<210> SEQ ID NO 102
<211> LENGTH: 20
<212> TYPE: PRT
<213> ORGANISM: artificial sequence
<220> FEATURE:
<223> OTHER INFORMATION: Synthetic construct

<400> SEQUENCE: 102

His Asn His Met Gln Glu Arg Tyr Thr Glu Pro Gln His Ser Pro Ser
1               5                   10                  15

Val Asn Gly Leu
            20

<210> SEQ ID NO 103
<211> LENGTH: 17
<212> TYPE: PRT
<213> ORGANISM: artificial sequence
<220> FEATURE:
<223> OTHER INFORMATION: Synthetic construct

<400> SEQUENCE: 103

Thr His Ser Thr His Asn His Gly Ser Pro Arg His Thr Asn Ala Asp
1               5                   10                  15

Ala

<210> SEQ ID NO 104
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 104

Gly Ser Cys Val Asp Thr His Lys Ala Asp Ser Cys Val Ala Asn Asn
1               5                   10                  15

Gly Pro Ala Thr
            20
```

<210> SEQ ID NO 105
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 105

Ala Gln Ser Gln Leu Pro Asp Lys His Ser Gly Leu His Glu Arg Ala
1               5                   10                  15

Pro Gln Arg Tyr
            20

<210> SEQ ID NO 106
<211> LENGTH: 20
<212> TYPE: PRT
<213> ORGANISM: artificial sequence
<220> FEATURE:
<223> OTHER INFORMATION: Synthetic construct

<400> SEQUENCE: 106

Ala Gln Ser Gln Leu Pro Ala Lys His Ser Gly Leu His Glu Arg Ala
1               5                   10                  15

Pro Gln Arg Tyr
            20

<210> SEQ ID NO 107
<211> LENGTH: 20
<212> TYPE: PRT
<213> ORGANISM: artificial sequence
<220> FEATURE:
<223> OTHER INFORMATION: Synthetic construct

<400> SEQUENCE: 107

Ala Gln Ser Gln Leu Pro Glu Lys His Ser Gly Leu His Glu Arg Ala
1               5                   10                  15

Pro Gln Arg Tyr
            20

<210> SEQ ID NO 108
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 108

Thr Asp Met Met His Asn His Ser Asp Asn Ser Pro Pro His Arg Arg
1               5                   10                  15

Ser Pro Arg Asn
            20

<210> SEQ ID NO 109
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 109

Thr Pro Pro Glu Leu Ala His Thr Pro His His Leu Ala Gln Thr Arg
1               5                   10                  15

Leu Thr Asp Arg
            20

```
<210> SEQ ID NO 110
<211> LENGTH: 12
<212> TYPE: PRT
<213> ORGANISM: artificial sequence
<220> FEATURE:
<223> OTHER INFORMATION: Synthetic construct

<400> SEQUENCE: 110

Arg Leu Leu Arg Leu Leu Arg Leu Leu Arg Leu Leu
1               5                   10

<210> SEQ ID NO 111
<211> LENGTH: 12
<212> TYPE: PRT
<213> ORGANISM: artificial sequence
<220> FEATURE:
<223> OTHER INFORMATION: Synthetic construct

<400> SEQUENCE: 111

Thr Pro Pro Glu Leu Leu His Gly Glu Pro Arg Ser
1               5                   10

<210> SEQ ID NO 112
<211> LENGTH: 12
<212> TYPE: PRT
<213> ORGANISM: artificial sequence
<220> FEATURE:
<223> OTHER INFORMATION: Synthetic construct

<400> SEQUENCE: 112

Thr Pro Pro Glu Leu Leu His Gly Ala Pro Arg Ser
1               5                   10

<210> SEQ ID NO 113
<211> LENGTH: 12
<212> TYPE: PRT
<213> ORGANISM: artificial sequence
<220> FEATURE:
<223> OTHER INFORMATION: Synthetic construct

<400> SEQUENCE: 113

Glu Gln Ile Ser Gly Ser Leu Val Ala Ala Pro Trp
1               5                   10

<210> SEQ ID NO 114
<211> LENGTH: 12
<212> TYPE: PRT
<213> ORGANISM: artificial sequence
<220> FEATURE:
<223> OTHER INFORMATION: Synthetic construct

<400> SEQUENCE: 114

Asn Glu Val Pro Ala Arg Asn Ala Pro Trp Leu Val
1               5                   10

<210> SEQ ID NO 115
<211> LENGTH: 13
<212> TYPE: PRT
<213> ORGANISM: artificial sequence
<220> FEATURE:
<223> OTHER INFORMATION: Synthetic construct

<400> SEQUENCE: 115

Asn Ser Pro Gly Tyr Gln Ala Asp Ser Val Ala Ile Gly
1               5                   10

<210> SEQ ID NO 116
```

<211> LENGTH: 12
<212> TYPE: PRT
<213> ORGANISM: artificial sequence
<220> FEATURE:
<223> OTHER INFORMATION: Synthetic construct

<400> SEQUENCE: 116

Ala Lys Pro Ile Ser Gln His Leu Gln Arg Gly Ser
1               5                   10

<210> SEQ ID NO 117
<211> LENGTH: 12
<212> TYPE: PRT
<213> ORGANISM: artificial sequence
<220> FEATURE:
<223> OTHER INFORMATION: Synthetic construct

<400> SEQUENCE: 117

Leu Asp Thr Ser Phe Pro Pro Val Pro Phe His Ala
1               5                   10

<210> SEQ ID NO 118
<211> LENGTH: 12
<212> TYPE: PRT
<213> ORGANISM: artificial sequence
<220> FEATURE:
<223> OTHER INFORMATION: Synthetic construct

<400> SEQUENCE: 118

Ser Leu Asn Trp Val Thr Ile Pro Gly Pro Lys Ile
1               5                   10

<210> SEQ ID NO 119
<211> LENGTH: 12
<212> TYPE: PRT
<213> ORGANISM: artificial sequence
<220> FEATURE:
<223> OTHER INFORMATION: Synthetic construct

<400> SEQUENCE: 119

Thr Gln Asp Ser Ala Gln Lys Ser Pro Ser Pro Leu
1               5                   10

<210> SEQ ID NO 120
<211> LENGTH: 12
<212> TYPE: PRT
<213> ORGANISM: artificial sequence
<220> FEATURE:
<223> OTHER INFORMATION: Synthetic construct

<400> SEQUENCE: 120

Lys Glu Leu Gln Thr Arg Asn Val Val Gln Arg Glu
1               5                   10

<210> SEQ ID NO 121
<211> LENGTH: 12
<212> TYPE: PRT
<213> ORGANISM: artificial sequence
<220> FEATURE:
<223> OTHER INFORMATION: Synthetic construct

<400> SEQUENCE: 121

Gln Arg Asn Ser Pro Pro Ala Met Ser Arg Arg Asp
1               5                   10

<210> SEQ ID NO 122
<211> LENGTH: 12
<212> TYPE: PRT

```
<213> ORGANISM: artificial sequence
<220> FEATURE:
<223> OTHER INFORMATION: Synthetic construct

<400> SEQUENCE: 122

Thr Pro Thr Ala Asn Gln Phe Thr Gln Ser Val Pro
1               5                   10

<210> SEQ ID NO 123
<211> LENGTH: 12
<212> TYPE: PRT
<213> ORGANISM: artificial sequence
<220> FEATURE:
<223> OTHER INFORMATION: Synthetic construct

<400> SEQUENCE: 123

Ala Ala Gly Leu Ser Gln Lys His Glu Arg Asn Arg
1               5                   10

<210> SEQ ID NO 124
<211> LENGTH: 12
<212> TYPE: PRT
<213> ORGANISM: artificial sequence
<220> FEATURE:
<223> OTHER INFORMATION: Synthetic construct

<400> SEQUENCE: 124

Glu Thr Val His Gln Thr Pro Leu Ser Asp Arg Pro
1               5                   10

<210> SEQ ID NO 125
<211> LENGTH: 12
<212> TYPE: PRT
<213> ORGANISM: artificial sequence
<220> FEATURE:
<223> OTHER INFORMATION: Synthetic construct

<400> SEQUENCE: 125

Lys Asn Phe Pro Gln Gln Lys Glu Phe Pro Leu Ser
1               5                   10

<210> SEQ ID NO 126
<211> LENGTH: 12
<212> TYPE: PRT
<213> ORGANISM: artificial sequence
<220> FEATURE:
<223> OTHER INFORMATION: Synthetic construct

<400> SEQUENCE: 126

Leu Pro Ala Leu His Ile Gln Arg His Pro Arg Met
1               5                   10

<210> SEQ ID NO 127
<211> LENGTH: 12
<212> TYPE: PRT
<213> ORGANISM: artificial sequence
<220> FEATURE:
<223> OTHER INFORMATION: Synthetic construct

<400> SEQUENCE: 127

Gln Pro Ser His Ser Gln Ser His Asn Leu Arg Ser
1               5                   10

<210> SEQ ID NO 128
<211> LENGTH: 12
<212> TYPE: PRT
<213> ORGANISM: artificial sequence
<220> FEATURE:
```

<223> OTHER INFORMATION: Synthetic construct

<400> SEQUENCE: 128

Arg Gly Ser Gln Lys Ser Lys Pro Pro Arg Pro Pro
1               5                   10

<210> SEQ ID NO 129
<211> LENGTH: 12
<212> TYPE: PRT
<213> ORGANISM: artificial sequence
<220> FEATURE:
<223> OTHER INFORMATION: Synthetic construct

<400> SEQUENCE: 129

Thr His Thr Gln Lys Thr Pro Leu Leu Tyr Tyr His
1               5                   10

<210> SEQ ID NO 130
<211> LENGTH: 12
<212> TYPE: PRT
<213> ORGANISM: artificial sequence
<220> FEATURE:
<223> OTHER INFORMATION: Synthetic construct

<400> SEQUENCE: 130

Thr Lys Gly Ser Ser Gln Ala Ile Leu Lys Ser Thr
1               5                   10

<210> SEQ ID NO 131
<211> LENGTH: 7
<212> TYPE: PRT
<213> ORGANISM: artificial sequence
<220> FEATURE:
<223> OTHER INFORMATION: Synthetic construct

<400> SEQUENCE: 131

Thr Ala Ala Thr Thr Ser Pro
1               5

<210> SEQ ID NO 132
<211> LENGTH: 7
<212> TYPE: PRT
<213> ORGANISM: artificial sequence
<220> FEATURE:
<223> OTHER INFORMATION: Synthetic construct

<400> SEQUENCE: 132

Leu Gly Ile Pro Gln Asn Leu
1               5

<210> SEQ ID NO 133
<211> LENGTH: 20
<212> TYPE: PRT
<213> ORGANISM: artificial sequence
<220> FEATURE:
<223> OTHER INFORMATION: Synthetic construct

<400> SEQUENCE: 133

Thr His Ser Thr His Asn His Gly Ser Pro Arg His Thr Asn Ala Asp
1               5                   10                  15

Ala Gly Asn Pro
            20

<210> SEQ ID NO 134
<211> LENGTH: 20
<212> TYPE: PRT
<213> ORGANISM: artificial sequence
<220> FEATURE:
<223> OTHER INFORMATION: Synthetic construct

<400> SEQUENCE: 134

Gln Gln His Lys Val His His Gln Asn Pro Asp Arg Ser Thr Gln Asp
1               5                   10                  15

Ala His His Ser
            20

<210> SEQ ID NO 135
<211> LENGTH: 15
<212> TYPE: PRT
<213> ORGANISM: artificial sequence
<220> FEATURE:
<223> OTHER INFORMATION: Synthetic construct

<400> SEQUENCE: 135

His His Gly Thr His His Asn Ala Thr Lys Gln Lys Asn His Val
1               5                   10                  15

<210> SEQ ID NO 136
<211> LENGTH: 15
<212> TYPE: PRT
<213> ORGANISM: artificial sequence
<220> FEATURE:
<223> OTHER INFORMATION: Synthetic construct

<400> SEQUENCE: 136

Ser Thr Leu His Lys Tyr Lys Ser Gln Asp Pro Thr Pro His His
1               5                   10                  15

<210> SEQ ID NO 137
<211> LENGTH: 12
<212> TYPE: PRT
<213> ORGANISM: artificial sequence
<220> FEATURE:
<223> OTHER INFORMATION: Synthetic construct

<400> SEQUENCE: 137

Ser Val Ser Val Gly Met Lys Pro Ser Pro Arg Pro
1               5                   10

<210> SEQ ID NO 138
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 138

Thr Pro Pro Thr Asn Val Leu Met Leu Ala Thr Lys
1               5                   10

<210> SEQ ID NO 139
<211> LENGTH: 12
<212> TYPE: PRT
<213> ORGANISM: artificial sequence
<220> FEATURE:
<223> OTHER INFORMATION: Synthetic construct

<400> SEQUENCE: 139

Thr Pro Pro Glu Leu Leu His Gly Asp Pro Arg Ser
1               5                   10

<210> SEQ ID NO 140
<211> LENGTH: 7
<212> TYPE: PRT

```
<213> ORGANISM: artificial sequence
<220> FEATURE:
<223> OTHER INFORMATION: synthetic hair-binding peptide

<400> SEQUENCE: 140

Asn Thr Ser Gln Leu Ser Thr
1               5

<210> SEQ ID NO 141
<211> LENGTH: 15
<212> TYPE: PRT
<213> ORGANISM: artificial sequence
<220> FEATURE:
<223> OTHER INFORMATION: Synthetic construct

<400> SEQUENCE: 141

Ser Thr Leu His Lys Tyr Lys Ser Gln Asp Pro Thr Pro His His
1               5                   10                  15

<210> SEQ ID NO 142
<211> LENGTH: 12
<212> TYPE: PRT
<213> ORGANISM: artificial sequence
<220> FEATURE:
<223> OTHER INFORMATION: synthetic hair-binding peptide

<400> SEQUENCE: 142

Gly Met Pro Ala Met His Trp Ile His Pro Phe Ala
1               5                   10

<210> SEQ ID NO 143
<211> LENGTH: 15
<212> TYPE: PRT
<213> ORGANISM: artificial sequence
<220> FEATURE:
<223> OTHER INFORMATION: synthetic hair-binding peptide

<400> SEQUENCE: 143

His Asp His Lys Asn Gln Lys Glu Thr His Gln Arg His Ala Ala
1               5                   10                  15

<210> SEQ ID NO 144
<211> LENGTH: 20
<212> TYPE: PRT
<213> ORGANISM: artificial sequence
<220> FEATURE:
<223> OTHER INFORMATION: Synthetic construct

<400> SEQUENCE: 144

His Asn His Met Gln Glu Arg Tyr Thr Asp Pro Gln His Ser Pro Ser
1               5                   10                  15

Val Asn Gly Leu
            20

<210> SEQ ID NO 145
<211> LENGTH: 20
<212> TYPE: PRT
<213> ORGANISM: artificial sequence
<220> FEATURE:
<223> OTHER INFORMATION: synthetic hair-binding peptide

<400> SEQUENCE: 145

Thr Ala Glu Ile Gln Ser Ser Lys Asn Pro Asn Pro His Pro Gln Arg
1               5                   10                  15

Ser Trp Thr Asn
            20
```

-continued

```
<210> SEQ ID NO 146
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 146

Ser Ser Ala Asp Phe Ala Ser Phe Gly Phe Phe Gly Phe Ser Ala Ala
1               5                   10                  15

Ser Ala Asp Ser Arg
            20

<210> SEQ ID NO 147
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 147

Ser Ser Phe Ala Glu Ala Trp Ser Arg Ala Trp Pro Arg Ala Glu Val
1               5                   10                  15

Phe Phe Pro Ser Arg Gly Tyr
            20

<210> SEQ ID NO 148
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 148

Ser Ser Phe Ser Val Asn Glu Pro His Ala Trp Met Ala Pro Leu Ser
1               5                   10                  15

Arg

<210> SEQ ID NO 149
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 149

Ser Ser Phe Ser Trp Val Tyr Gly His Gly Gly Leu Gly Phe Ala Ser
1               5                   10                  15

Arg

<210> SEQ ID NO 150
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 150

Ser Ser Phe Val Ser Trp Ser Pro Tyr Lys Ser Pro Pro Glu Leu Ser
1               5                   10                  15

Arg

<210> SEQ ID NO 151
<211> LENGTH: 21
```

```
<212> TYPE: PRT
<213> ORGANISM: artificial sequence
<220> FEATURE:
<223> OTHER INFORMATION: Dyed-hair-bindg peptide

<400> SEQUENCE: 151

Ser Ser Phe Tyr Gly Ser Ser Ala Phe Val Ser Gly Val Ser Val
1               5                   10                  15

Ala Tyr Gly Ser Arg
            20

<210> SEQ ID NO 152
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 152

Ser Ser Gly Ser Val Ala Val Ser Ala Glu Ala Ser Trp Phe Ser Gly
1               5                   10                  15

Val Ala Ala Ser Arg
            20

<210> SEQ ID NO 153
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 153

Ser Ser His Asp Glu His Tyr Gln Tyr His Tyr Tyr Ser Ser Arg
1               5                   10                  15

<210> SEQ ID NO 154
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 154

Ser Ser His Tyr Tyr Tyr Asn Asp Tyr Asp His Gln Ser Ser Arg
1               5                   10                  15

<210> SEQ ID NO 155
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 155

Ser Ser Leu Phe Asn Met Tyr Gly His Gln Ser Val Leu Gly Pro Ser
1               5                   10                  15

Arg

<210> SEQ ID NO 156
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 156
```

```
Ser Ser Leu Phe Ser Asp Val His Tyr Gly Ser Asn Lys Ala Leu Ser
1               5                   10                  15

Arg
```

<210> SEQ ID NO 157
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 157

```
Ser Ser Leu Leu Ser Asp Phe His Tyr Gly Asp Met Trp Asp Ala Ser
1               5                   10                  15

Arg
```

<210> SEQ ID NO 158
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 158

```
Ser Ser Asn Tyr Asn Tyr Asn Tyr Asn Tyr Gln Tyr Ser Ser Arg
1               5                   10                  15
```

<210> SEQ ID NO 159
<211> LENGTH: 21
<212> TYPE: PRT
<213> ORGANISM: artificial sequence
<220> FEATURE:
<223> OTHER INFORMATION: synethetic construct

<400> SEQUENCE: 159

```
Ser Ser Asn Tyr Asn Tyr Asn Tyr Asn Tyr Gln Tyr Ser Ser Arg Glu
1               5                   10                  15

Gly Glu Gly Glu Arg
            20
```

<210> SEQ ID NO 160
<211> LENGTH: 21
<212> TYPE: PRT
<213> ORGANISM: ARTIFICIAL SEQUENCE
<220> FEATURE:
<223> OTHER INFORMATION: Synthetic construct

<400> SEQUENCE: 160

```
Ser Ser Asn Tyr Asn Tyr Asn Tyr Asn Tyr Gln Tyr Ser Ser Arg Lys
1               5                   10                  15

Arg Lys Arg Lys Asp
            20
```

<210> SEQ ID NO 161
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 161

```
Ser Ser Gln Tyr Tyr Gln Asp Tyr Gln Tyr Tyr His Ser Ser Arg
1               5                   10                  15
```

<210> SEQ ID NO 162

```
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 162

Ser Ser Ser Cys Met Gly Ser His Asn Pro Arg Met Ser Val Glu Glu
1               5                   10                  15

Ser Thr Arg Asn Cys Ser Arg
            20

<210> SEQ ID NO 163
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 163

Ser Ser Ser Cys Asn Asn Asn Trp Phe Tyr Ser Ser Thr Leu Pro Gly
1               5                   10                  15

Gly Asp His Ala Cys Ser Arg
            20

<210> SEQ ID NO 164
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 164

Ser Ser Ser Cys Tyr Asp Val Glu Cys Ser Ser Phe Val Ala Trp Met
1               5                   10                  15

Arg Gly Pro Ser Ser Ser Arg
            20

<210> SEQ ID NO 165
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 165

Ser Ser Ser Phe Ala Ala Ser Ser Ala Phe Ser Phe Leu Val Asp Ala
1               5                   10                  15

Val Ala Trp Ser Arg
            20

<210> SEQ ID NO 166
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 166

Ser Ser Ser Phe Ala Tyr Leu Val Pro Asp Asp Gly Trp Leu Ser Ser
1               5                   10                  15

Arg

<210> SEQ ID NO 167
<211> LENGTH: 21
```

```
<212> TYPE: PRT
<213> ORGANISM: artificial sequence
<220> FEATURE:
<223> OTHER INFORMATION: Dyed-hair-bindg peptide

<400> SEQUENCE: 167

Ser Ser Ser Gly Ala Val Phe Ser Ser Gly Gly Ala Asp Ala Gly Trp
1               5                   10                  15

Gly Val Trp Ser Arg
            20

<210> SEQ ID NO 168
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 168

Ser Ser Ser Ser Ala Asp Ala Ala Tyr Gly His Cys Cys Gly Ala Gly
1               5                   10                  15

Phe Ser Thr Phe Ser Ser Arg
            20

<210> SEQ ID NO 169
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 169

Ser Ser Ser Ser Asp Val His Asn Ser Ile Ile Gly Trp Asp Phe Tyr
1               5                   10                  15

His Ser Arg Gly Ser Ser Arg
            20

<210> SEQ ID NO 170
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 170

Ser Ser Ser Ser Leu Asp Phe Phe Ser Tyr Ser Ala Phe Ser Gly Gly
1               5                   10                  15

Val Ala Glu Ser Arg
            20

<210> SEQ ID NO 171
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 171

Ser Ser Ser Ser Asn Asp Ser Asn Val Ser Trp Phe His Tyr Tyr Ala
1               5                   10                  15

Ser Gly Leu Thr Ser Ser Arg
            20

<210> SEQ ID NO 172
<211> LENGTH: 21
```

```
<212> TYPE: PRT
<213> ORGANISM: artificial sequence
<220> FEATURE:
<223> OTHER INFORMATION: Dyed-hair-bindg peptide

<400> SEQUENCE: 172

Ser Ser Val Asp Tyr Glu Val Pro Leu Ala Val Ala Ala Glu Trp Gly
1               5                   10                  15

Phe Ser Val Ser Arg
            20

<210> SEQ ID NO 173
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 173

Ser Ser Tyr His Tyr Asp Tyr Asp His Tyr Tyr Glu Ser Ser Arg
1               5                   10                  15

<210> SEQ ID NO 174
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 174

Ser Ser Tyr Tyr Asn Tyr His Tyr Gln Tyr Gln Asp Ser Ser Arg
1               5                   10                  15

<210> SEQ ID NO 175
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 175

Ser Ser Tyr Tyr Tyr Asp Tyr Tyr Gln Gln Asp Tyr Ser Ser Arg
1               5                   10                  15

<210> SEQ ID NO 176
<211> LENGTH: 12
<212> TYPE: PRT
<213> ORGANISM: artificial sequence
<220> FEATURE:
<223> OTHER INFORMATION: Synthetic construct

<400> SEQUENCE: 176

Lys Arg Gly Arg His Lys Arg Pro Lys Arg His Lys
1               5                   10

<210> SEQ ID NO 177
<211> LENGTH: 7
<212> TYPE: PRT
<213> ORGANISM: artificial sequence
<220> FEATURE:
<223> OTHER INFORMATION: Synthetic construct

<400> SEQUENCE: 177

Arg Leu Leu Arg Leu Leu Arg
1               5

<210> SEQ ID NO 178
```

```
<211> LENGTH: 12
<212> TYPE: PRT
<213> ORGANISM: artificial sequence
<220> FEATURE:
<223> OTHER INFORMATION: Synthetic construct

<400> SEQUENCE: 178

His Lys Pro Arg Gly Gly Arg Lys Lys Ala Leu His
1               5                   10

<210> SEQ ID NO 179
<211> LENGTH: 18
<212> TYPE: PRT
<213> ORGANISM: artificial sequence
<220> FEATURE:
<223> OTHER INFORMATION: Synthetic construct

<400> SEQUENCE: 179

Lys Pro Arg Pro Pro His Gly Lys Lys His Arg Pro Lys His Arg Pro
1               5                   10                  15

Lys Lys

<210> SEQ ID NO 180
<211> LENGTH: 18
<212> TYPE: PRT
<213> ORGANISM: artificial sequence
<220> FEATURE:
<223> OTHER INFORMATION: Synthetic construct

<400> SEQUENCE: 180

Arg Gly Arg Pro Lys Lys Gly His Gly Lys Arg Pro Gly His Arg Ala
1               5                   10                  15

Arg Lys

<210> SEQ ID NO 181
<211> LENGTH: 12
<212> TYPE: PRT
<213> ORGANISM: artificial sequence
<220> FEATURE:
<223> OTHER INFORMATION: Synthetic construct

<400> SEQUENCE: 181

Thr Pro Phe His Ser Pro Glu Asn Ala Pro Gly Ser
1               5                   10

<210> SEQ ID NO 182
<211> LENGTH: 13
<212> TYPE: PRT
<213> ORGANISM: artificial sequence
<220> FEATURE:
<223> OTHER INFORMATION: Synthetic construct

<400> SEQUENCE: 182

Thr Pro Phe His Ser Pro Glu Asn Ala Pro Gly Ser Lys
1               5                   10

<210> SEQ ID NO 183
<211> LENGTH: 16
<212> TYPE: PRT
<213> ORGANISM: artificial sequence
<220> FEATURE:
<223> OTHER INFORMATION: Synthetic construct

<400> SEQUENCE: 183

Thr Pro Phe His Ser Pro Glu Asn Ala Pro Gly Ser Gly Gly Gly Ser
1               5                   10                  15
```

```
<210> SEQ ID NO 184
<211> LENGTH: 17
<212> TYPE: PRT
<213> ORGANISM: artificial sequence
<220> FEATURE:
<223> OTHER INFORMATION: Synthetic construct

<400> SEQUENCE: 184

Thr Pro Phe His Ser Pro Glu Asn Ala Pro Gly Ser Gly Gly Gly Ser
1               5                   10                  15

Ser

<210> SEQ ID NO 185
<211> LENGTH: 15
<212> TYPE: PRT
<213> ORGANISM: artificial sequence
<220> FEATURE:
<223> OTHER INFORMATION: Synthetic construct

<400> SEQUENCE: 185

Thr Pro Phe His Ser Pro Glu Asn Ala Pro Gly Ser Gly Gly Gly
1               5                   10                  15

<210> SEQ ID NO 186
<211> LENGTH: 7
<212> TYPE: PRT
<213> ORGANISM: artificial sequence
<220> FEATURE:
<223> OTHER INFORMATION: Synthetic construct

<400> SEQUENCE: 186

Phe Thr Gln Ser Leu Pro Arg
1               5

<210> SEQ ID NO 187
<211> LENGTH: 12
<212> TYPE: PRT
<213> ORGANISM: artificial sequence
<220> FEATURE:
<223> OTHER INFORMATION: Synthetic construct

<400> SEQUENCE: 187

Lys Gln Ala Thr Phe Pro Pro Asn Pro Thr Ala Tyr
1               5                   10

<210> SEQ ID NO 188
<211> LENGTH: 12
<212> TYPE: PRT
<213> ORGANISM: artificial sequence
<220> FEATURE:
<223> OTHER INFORMATION: Synthetic construct

<400> SEQUENCE: 188

His Gly His Met Val Ser Thr Ser Gln Leu Ser Ile
1               5                   10

<210> SEQ ID NO 189
<211> LENGTH: 7
<212> TYPE: PRT
<213> ORGANISM: artificial sequence
<220> FEATURE:
<223> OTHER INFORMATION: Synthetic construct

<400> SEQUENCE: 189

Leu Ser Pro Ser Arg Met Lys
1               5
```

```
<210> SEQ ID NO 190
<211> LENGTH: 7
<212> TYPE: PRT
<213> ORGANISM: artificial sequence
<220> FEATURE:
<223> OTHER INFORMATION: Synthetic construct

<400> SEQUENCE: 190

Leu Pro Ile Pro Arg Met Lys
1               5

<210> SEQ ID NO 191
<211> LENGTH: 7
<212> TYPE: PRT
<213> ORGANISM: artificial sequence
<220> FEATURE:
<223> OTHER INFORMATION: Synthetic construct

<400> SEQUENCE: 191

His Gln Arg Pro Tyr Leu Thr
1               5

<210> SEQ ID NO 192
<211> LENGTH: 7
<212> TYPE: PRT
<213> ORGANISM: artificial sequence
<220> FEATURE:
<223> OTHER INFORMATION: Synthetic construct

<400> SEQUENCE: 192

Phe Pro Pro Leu Leu Arg Leu
1               5

<210> SEQ ID NO 193
<211> LENGTH: 7
<212> TYPE: PRT
<213> ORGANISM: artificial sequence
<220> FEATURE:
<223> OTHER INFORMATION: Synthetic construct

<400> SEQUENCE: 193

Gln Ala Thr Phe Met Tyr Asn
1               5

<210> SEQ ID NO 194
<211> LENGTH: 11
<212> TYPE: PRT
<213> ORGANISM: artificial sequence
<220> FEATURE:
<223> OTHER INFORMATION: Synthetic construct

<400> SEQUENCE: 194

Val Leu Thr Ser Gln Leu Pro Asn His Ser Met
1               5                   10

<210> SEQ ID NO 195
<211> LENGTH: 7
<212> TYPE: PRT
<213> ORGANISM: artificial sequence
<220> FEATURE:
<223> OTHER INFORMATION: Synthetic construct

<400> SEQUENCE: 195

His Ser Thr Ala Tyr Leu Thr
1               5

<210> SEQ ID NO 196
```

<211> LENGTH: 12
<212> TYPE: PRT
<213> ORGANISM: artificial sequence
<220> FEATURE:
<223> OTHER INFORMATION: Synthetic construct

<400> SEQUENCE: 196

Ala Pro Gln Gln Arg Pro Met Lys Thr Phe Asn Thr
1               5                   10

<210> SEQ ID NO 197
<211> LENGTH: 12
<212> TYPE: PRT
<213> ORGANISM: artificial sequence
<220> FEATURE:
<223> OTHER INFORMATION: Synthetic construct

<400> SEQUENCE: 197

Ala Pro Gln Gln Arg Pro Met Lys Thr Val Gln Tyr
1               5                   10

<210> SEQ ID NO 198
<211> LENGTH: 7
<212> TYPE: PRT
<213> ORGANISM: artificial sequence
<220> FEATURE:
<223> OTHER INFORMATION: Synthetic construct

<400> SEQUENCE: 198

Pro Pro Trp Leu Asp Leu Leu
1               5

<210> SEQ ID NO 199
<211> LENGTH: 7
<212> TYPE: PRT
<213> ORGANISM: artificial sequence
<220> FEATURE:
<223> OTHER INFORMATION: Synthetic construct

<400> SEQUENCE: 199

Pro Pro Trp Thr Phe Pro Leu
1               5

<210> SEQ ID NO 200
<211> LENGTH: 7
<212> TYPE: PRT
<213> ORGANISM: artificial sequence
<220> FEATURE:
<223> OTHER INFORMATION: Synthetic construct

<400> SEQUENCE: 200

Ser Val Thr His Leu Thr Ser
1               5

<210> SEQ ID NO 201
<211> LENGTH: 7
<212> TYPE: PRT
<213> ORGANISM: artificial sequence
<220> FEATURE:
<223> OTHER INFORMATION: Synthetic construct

<400> SEQUENCE: 201

Val Ile Thr Arg Leu Thr Ser
1               5

<210> SEQ ID NO 202
<211> LENGTH: 12
<212> TYPE: PRT

```
<213> ORGANISM: artificial sequence
<220> FEATURE:
<223> OTHER INFORMATION: Synthetic construct

<400> SEQUENCE: 202

Asp Leu Lys Pro Pro Leu Leu Ala Leu Ser Lys Val
1               5                   10

<210> SEQ ID NO 203
<211> LENGTH: 12
<212> TYPE: PRT
<213> ORGANISM: artificial sequence
<220> FEATURE:
<223> OTHER INFORMATION: Synthetic construct

<400> SEQUENCE: 203

Ser His Pro Ser Gly Ala Leu Gln Glu Gly Thr Phe
1               5                   10

<210> SEQ ID NO 204
<211> LENGTH: 12
<212> TYPE: PRT
<213> ORGANISM: artificial sequence
<220> FEATURE:
<223> OTHER INFORMATION: Synthetic construct

<400> SEQUENCE: 204

Phe Pro Leu Thr Ser Lys Pro Ser Gly Ala Cys Thr
1               5                   10

<210> SEQ ID NO 205
<211> LENGTH: 12
<212> TYPE: PRT
<213> ORGANISM: artificial sequence
<220> FEATURE:
<223> OTHER INFORMATION: Synthetic construct

<400> SEQUENCE: 205

Asp Leu Lys Pro Pro Leu Leu Ala Leu Ser Lys Val
1               5                   10

<210> SEQ ID NO 206
<211> LENGTH: 7
<212> TYPE: PRT
<213> ORGANISM: artificial sequence
<220> FEATURE:
<223> OTHER INFORMATION: Synthetic construct

<400> SEQUENCE: 206

Pro Leu Leu Ala Leu His Ser
1               5

<210> SEQ ID NO 207
<211> LENGTH: 7
<212> TYPE: PRT
<213> ORGANISM: artificial sequence
<220> FEATURE:
<223> OTHER INFORMATION: Synthetic construct

<400> SEQUENCE: 207

Val Pro Ile Ser Thr Gln Ile
1               5

<210> SEQ ID NO 208
<211> LENGTH: 12
<212> TYPE: PRT
<213> ORGANISM: artificial sequence
<220> FEATURE:
```

<223> OTHER INFORMATION: Synthetic construct

<400> SEQUENCE: 208

Tyr Ala Lys Gln His Tyr Pro Ile Ser Thr Phe Lys
1               5                   10

<210> SEQ ID NO 209
<211> LENGTH: 7
<212> TYPE: PRT
<213> ORGANISM: artificial sequence
<220> FEATURE:
<223> OTHER INFORMATION: Synthetic construct

<400> SEQUENCE: 209

His Ser Thr Ala Tyr Leu Thr
1               5

<210> SEQ ID NO 210
<211> LENGTH: 12
<212> TYPE: PRT
<213> ORGANISM: artificial sequence
<220> FEATURE:
<223> OTHER INFORMATION: Synthetic construct

<400> SEQUENCE: 210

Ser Thr Ala Tyr Leu Val Ala Met Ser Ala Ala Pro
1               5                   10

<210> SEQ ID NO 211
<211> LENGTH: 12
<212> TYPE: PRT
<213> ORGANISM: artificial sequence
<220> FEATURE:
<223> OTHER INFORMATION: Synthetic construct

<400> SEQUENCE: 211

Ser Val Ser Val Gly Met Lys Pro Ser Pro Arg Pro
1               5                   10

<210> SEQ ID NO 212
<211> LENGTH: 12
<212> TYPE: PRT
<213> ORGANISM: artificial sequence
<220> FEATURE:
<223> OTHER INFORMATION: Synthetic construct

<400> SEQUENCE: 212

Thr Met Gly Phe Thr Ala Pro Arg Phe Pro His Tyr
1               5                   10

<210> SEQ ID NO 213
<211> LENGTH: 12
<212> TYPE: PRT
<213> ORGANISM: artificial sequence
<220> FEATURE:
<223> OTHER INFORMATION: Synthetic construct

<400> SEQUENCE: 213

Asn Leu Gln His Ser Val Gly Thr Ser Pro Val Trp
1               5                   10

<210> SEQ ID NO 214
<211> LENGTH: 15
<212> TYPE: PRT
<213> ORGANISM: artificial sequence
<220> FEATURE:
<223> OTHER INFORMATION: Synthetic construct

```
<400> SEQUENCE: 214

Gln Leu Ser Tyr His Ala Tyr Pro Gln Ala Asn His His Ala Pro
1               5                   10                  15

<210> SEQ ID NO 215
<211> LENGTH: 12
<212> TYPE: PRT
<213> ORGANISM: artificial sequence
<220> FEATURE:
<223> OTHER INFORMATION: Synthetic construct

<400> SEQUENCE: 215

Asn Gln Ala Ala Ser Ile Thr Lys Arg Val Pro Tyr
1               5                   10

<210> SEQ ID NO 216
<211> LENGTH: 14
<212> TYPE: PRT
<213> ORGANISM: artificial sequence
<220> FEATURE:
<223> OTHER INFORMATION: Synthetic construct

<400> SEQUENCE: 216

Ser Gly Cys His Leu Val Tyr Asp Asn Gly Phe Cys Asp His
1               5                   10

<210> SEQ ID NO 217
<211> LENGTH: 14
<212> TYPE: PRT
<213> ORGANISM: artificial sequence
<220> FEATURE:
<223> OTHER INFORMATION: Synthetic construct

<400> SEQUENCE: 217

Ala Ser Cys Pro Ser Ala Ser His Ala Asp Pro Cys Ala His
1               5                   10

<210> SEQ ID NO 218
<211> LENGTH: 14
<212> TYPE: PRT
<213> ORGANISM: artificial sequence
<220> FEATURE:
<223> OTHER INFORMATION: Synthetic construct

<400> SEQUENCE: 218

Asn Leu Cys Asp Ser Ala Arg Asp Ser Pro Arg Cys Lys Val
1               5                   10

<210> SEQ ID NO 219
<211> LENGTH: 12
<212> TYPE: PRT
<213> ORGANISM: artificial sequence
<220> FEATURE:
<223> OTHER INFORMATION: Synthetic construct

<400> SEQUENCE: 219

Asn His Ser Asn Trp Lys Thr Ala Ala Asp Phe Leu
1               5                   10

<210> SEQ ID NO 220
<211> LENGTH: 12
<212> TYPE: PRT
<213> ORGANISM: artificial sequence
<220> FEATURE:
<223> OTHER INFORMATION: Synthetic construct

<400> SEQUENCE: 220
```

```
Gly Ser Ser Thr Val Gly Arg Pro Leu Ser Tyr Glu
1               5                   10
```

<210> SEQ ID NO 221
<211> LENGTH: 12
<212> TYPE: PRT
<213> ORGANISM: artificial sequence
<220> FEATURE:
<223> OTHER INFORMATION: Synthetic construct

<400> SEQUENCE: 221

```
Ser Asp Thr Ile Ser Arg Leu His Val Ser Met Thr
1               5                   10
```

<210> SEQ ID NO 222
<211> LENGTH: 12
<212> TYPE: PRT
<213> ORGANISM: artificial sequence
<220> FEATURE:
<223> OTHER INFORMATION: Synthetic construct

<400> SEQUENCE: 222

```
Ser Pro Leu Thr Val Pro Tyr Glu Arg Lys Leu Leu
1               5                   10
```

<210> SEQ ID NO 223
<211> LENGTH: 12
<212> TYPE: PRT
<213> ORGANISM: artificial sequence
<220> FEATURE:
<223> OTHER INFORMATION: Synthetic construct

<400> SEQUENCE: 223

```
Ser Pro Tyr Pro Ser Trp Ser Thr Pro Ala Gly Arg
1               5                   10
```

<210> SEQ ID NO 224
<211> LENGTH: 12
<212> TYPE: PRT
<213> ORGANISM: artificial sequence
<220> FEATURE:
<223> OTHER INFORMATION: Synthetic construct

<400> SEQUENCE: 224

```
Val Gln Pro Ile Thr Asn Thr Arg Tyr Glu Gly Gly
1               5                   10
```

<210> SEQ ID NO 225
<211> LENGTH: 12
<212> TYPE: PRT
<213> ORGANISM: artificial sequence
<220> FEATURE:
<223> OTHER INFORMATION: Synthetic construct

<400> SEQUENCE: 225

```
Trp Pro Met His Pro Glu Lys Gly Ser Arg Trp Ser
1               5                   10
```

<210> SEQ ID NO 226
<211> LENGTH: 14
<212> TYPE: PRT
<213> ORGANISM: artificial sequence
<220> FEATURE:
<223> OTHER INFORMATION: Synthetic construct

<400> SEQUENCE: 226

```
Asp Ala Cys Ser Gly Asn Gly His Pro Asn Asn Cys Asp Arg
1               5                   10
```

```
<210> SEQ ID NO 227
<211> LENGTH: 14
<212> TYPE: PRT
<213> ORGANISM: artificial sequence
<220> FEATURE:
<223> OTHER INFORMATION: Synthetic construct

<400> SEQUENCE: 227

Asp His Cys Leu Gly Arg Gln Leu Gln Pro Val Cys Tyr Pro
1               5                   10

<210> SEQ ID NO 228
<211> LENGTH: 14
<212> TYPE: PRT
<213> ORGANISM: artificial sequence
<220> FEATURE:
<223> OTHER INFORMATION: Synthetic construct

<400> SEQUENCE: 228

Asp Trp Cys Asp Thr Ile Ile Pro Gly Arg Thr Cys His Gly
1               5                   10

<210> SEQ ID NO 229
<211> LENGTH: 12
<212> TYPE: PRT
<213> ORGANISM: artificial sequence
<220> FEATURE:
<223> OTHER INFORMATION: Synthetic construct

<400> SEQUENCE: 229

Ala Leu Pro Arg Ile Ala Asn Thr Trp Ser Pro Ser
1               5                   10

<210> SEQ ID NO 230
<211> LENGTH: 12
<212> TYPE: PRT
<213> ORGANISM: artificial sequence
<220> FEATURE:
<223> OTHER INFORMATION: Synthetic construct

<400> SEQUENCE: 230

Tyr Pro Ser Phe Ser Pro Thr Tyr Arg Pro Ala Phe
1               5                   10

<210> SEQ ID NO 231
<211> LENGTH: 20
<212> TYPE: PRT
<213> ORGANISM: artificial sequence
<220> FEATURE:
<223> OTHER INFORMATION: Synthetic construct

<400> SEQUENCE: 231

Ala His Pro Glu Ser Leu Gly Ile Lys Tyr Ala Leu Asp Gly Asn Ser
1               5                   10                  15

Asp Pro His Ala
            20

<210> SEQ ID NO 232
<211> LENGTH: 20
<212> TYPE: PRT
<213> ORGANISM: artificial sequence
<220> FEATURE:
<223> OTHER INFORMATION: Synthetic construct

<400> SEQUENCE: 232

Ala Ser Val Ser Asn Tyr Pro Pro Ile His His Leu Ala Thr Ser Asn
```

```
                1               5                  10                  15

Thr Thr Val Asn
            20

<210> SEQ ID NO 233
<211> LENGTH: 14
<212> TYPE: PRT
<213> ORGANISM: artificial sequence
<220> FEATURE:
<223> OTHER INFORMATION: Synthetic construct

<400> SEQUENCE: 233

Asp Glu Cys Met Glu Pro Leu Asn Ala Ala His Cys Trp Arg
1               5                  10

<210> SEQ ID NO 234
<211> LENGTH: 14
<212> TYPE: PRT
<213> ORGANISM: artificial sequence
<220> FEATURE:
<223> OTHER INFORMATION: Synthetic construct

<400> SEQUENCE: 234

Asp Glu Cys Met His Gly Ser Asp Val Glu Phe Cys Thr Ser
1               5                  10

<210> SEQ ID NO 235
<211> LENGTH: 14
<212> TYPE: PRT
<213> ORGANISM: artificial sequence
<220> FEATURE:
<223> OTHER INFORMATION: Synthetic construct

<400> SEQUENCE: 235

Asp Leu Cys Ser Met Gln Met Met Asn Thr Gly Cys His Tyr
1               5                  10

<210> SEQ ID NO 236
<211> LENGTH: 14
<212> TYPE: PRT
<213> ORGANISM: artificial sequence
<220> FEATURE:
<223> OTHER INFORMATION: Synthetic construct

<400> SEQUENCE: 236

Asp Leu Cys Ser Ser Pro Ser Thr Trp Gly Ser Cys Ile Arg
1               5                  10

<210> SEQ ID NO 237
<211> LENGTH: 20
<212> TYPE: PRT
<213> ORGANISM: artificial sequence
<220> FEATURE:
<223> OTHER INFORMATION: Synthetic construct

<400> SEQUENCE: 237

Asp Pro Asn Glu Ser Asn Tyr Glu Asn Ala Thr Thr Val Ser Gln Pro
1               5                  10                  15

Thr Arg His Leu
            20

<210> SEQ ID NO 238
<211> LENGTH: 20
<212> TYPE: PRT
<213> ORGANISM: artificial sequence
<220> FEATURE:
<223> OTHER INFORMATION: Synthetic construct
```

<400> SEQUENCE: 238

Glu Pro Thr His Pro Thr Met Arg Ala Gln Met His Gln Ser Leu Arg
1               5                   10                  15

Ser Ser Ser Pro
            20

<210> SEQ ID NO 239
<211> LENGTH: 20
<212> TYPE: PRT
<213> ORGANISM: artificial sequence
<220> FEATURE:
<223> OTHER INFORMATION: Synthetic construct

<400> SEQUENCE: 239

Gly Asn Thr Asp Thr Thr Pro Pro Asn Ala Val Met Glu Pro Thr Val
1               5                   10                  15

Gln His Lys Trp
            20

<210> SEQ ID NO 240
<211> LENGTH: 15
<212> TYPE: PRT
<213> ORGANISM: artificial sequence
<220> FEATURE:
<223> OTHER INFORMATION: Synthetic construct

<400> SEQUENCE: 240

Asn Gly Pro Asp Met Val Gln Ser Val Gly Lys His Lys Asn Ser
1               5                   10                  15

<210> SEQ ID NO 241
<211> LENGTH: 15
<212> TYPE: PRT
<213> ORGANISM: artificial sequence
<220> FEATURE:
<223> OTHER INFORMATION: Synthetic construct

<400> SEQUENCE: 241

Asn Gly Pro Glu Val Arg Gln Ile Pro Ala Asn Phe Glu Lys Leu
1               5                   10                  15

<210> SEQ ID NO 242
<211> LENGTH: 20
<212> TYPE: PRT
<213> ORGANISM: artificial sequence
<220> FEATURE:
<223> OTHER INFORMATION: Synthetic construct

<400> SEQUENCE: 242

Asn Asn Thr Ser Ala Asp Asn Pro Pro Glu Thr Asp Ser Lys His His
1               5                   10                  15

Leu Ser Met Ser
            20

<210> SEQ ID NO 243
<211> LENGTH: 20
<212> TYPE: PRT
<213> ORGANISM: artificial sequence
<220> FEATURE:
<223> OTHER INFORMATION: Synthetic construct

<400> SEQUENCE: 243

Asn Asn Thr Trp Pro Glu Gly Ala Gly His Thr Met Pro Ser Thr Asn
1               5                   10                  15

Ile Arg Gln Ala
            20

<210> SEQ ID NO 244
<211> LENGTH: 20
<212> TYPE: PRT
<213> ORGANISM: artificial sequence
<220> FEATURE:
<223> OTHER INFORMATION: Synthetic construct

<400> SEQUENCE: 244

Asn Pro Thr Ala Thr Pro His Met Lys Asp Pro Met His Ser Asn Ala
1               5                   10                  15

His Ser Ser Ala
            20

<210> SEQ ID NO 245
<211> LENGTH: 20
<212> TYPE: PRT
<213> ORGANISM: artificial sequence
<220> FEATURE:
<223> OTHER INFORMATION: Synthetic construct

<400> SEQUENCE: 245

Asn Pro Thr Asp His Ile Pro Ala Asn Ser Thr Asn Ser Arg Val Ser
1               5                   10                  15

Lys Gly Asn Thr
            20

<210> SEQ ID NO 246
<211> LENGTH: 15
<212> TYPE: PRT
<213> ORGANISM: artificial sequence
<220> FEATURE:
<223> OTHER INFORMATION: Synthetic construct

<400> SEQUENCE: 246

Asn Pro Thr Asp Ser Thr His Met Met His Ala Arg Asn His Glu
1               5                   10                  15

<210> SEQ ID NO 247
<211> LENGTH: 14
<212> TYPE: PRT
<213> ORGANISM: artificial sequence
<220> FEATURE:
<223> OTHER INFORMATION: Synthetic construct

<400> SEQUENCE: 247

Gln His Cys Ile Thr Glu Arg Leu His Pro Pro Cys Thr Lys
1               5                   10

<210> SEQ ID NO 248
<211> LENGTH: 14
<212> TYPE: PRT
<213> ORGANISM: artificial sequence
<220> FEATURE:
<223> OTHER INFORMATION: Synthetic construct

<400> SEQUENCE: 248

Thr Pro Cys Ala Pro Ala Ser Phe Asn Pro His Cys Ser Arg
1               5                   10

<210> SEQ ID NO 249
<211> LENGTH: 14
<212> TYPE: PRT
<213> ORGANISM: artificial sequence
<220> FEATURE:

<223> OTHER INFORMATION: Synthetic construct

<400> SEQUENCE: 249

Thr Pro Cys Ala Thr Tyr Pro His Phe Ser Gly Cys Arg Ala
1               5                   10

<210> SEQ ID NO 250
<211> LENGTH: 20
<212> TYPE: PRT
<213> ORGANISM: artificial sequence
<220> FEATURE:
<223> OTHER INFORMATION: Synthetic construct

<400> SEQUENCE: 250

Trp Cys Thr Asp Phe Cys Thr Arg Ser Thr Pro Thr Ser Thr Ser Arg
1               5                   10                  15

Ser Thr Thr Ser
            20

<210> SEQ ID NO 251
<211> LENGTH: 20
<212> TYPE: PRT
<213> ORGANISM: artificial sequence
<220> FEATURE:
<223> OTHER INFORMATION: Synthetic construct

<400> SEQUENCE: 251

Ala Pro Pro Leu Lys Thr Tyr Met Gln Glu Arg Glu Leu Thr Met Ser
1               5                   10                  15

Gln Asn Lys Asp
            20

<210> SEQ ID NO 252
<211> LENGTH: 20
<212> TYPE: PRT
<213> ORGANISM: artificial sequence
<220> FEATURE:
<223> OTHER INFORMATION: Synthetic construct

<400> SEQUENCE: 252

Glu Pro Pro Thr Arg Thr Arg Val Asn Asn His Thr Val Thr Val Gln
1               5                   10                  15

Ala Gln Gln His
            20

<210> SEQ ID NO 253
<211> LENGTH: 14
<212> TYPE: PRT
<213> ORGANISM: artificial sequence
<220> FEATURE:
<223> OTHER INFORMATION: Synthetic construct

<400> SEQUENCE: 253

Gly Tyr Cys Leu Arg Gly Asp Glu Pro Ala Val Cys Ser Gly
1               5                   10

<210> SEQ ID NO 254
<211> LENGTH: 20
<212> TYPE: PRT
<213> ORGANISM: artificial sequence
<220> FEATURE:
<223> OTHER INFORMATION: Synthetic construct

<400> SEQUENCE: 254

Leu Ser Ser Lys Asp Phe Gly Val Thr Asn Thr Asp Gln Arg Thr Tyr
1               5                   10                  15

Asp Tyr Thr Thr
            20

<210> SEQ ID NO 255
<211> LENGTH: 14
<212> TYPE: PRT
<213> ORGANISM: artificial sequence
<220> FEATURE:
<223> OTHER INFORMATION: Synthetic construct

<400> SEQUENCE: 255

Asn Phe Cys Glu Thr Gln Leu Asp Leu Ser Val Cys Thr Val
1               5                   10

<210> SEQ ID NO 256
<211> LENGTH: 14
<212> TYPE: PRT
<213> ORGANISM: artificial sequence
<220> FEATURE:
<223> OTHER INFORMATION: Synthetic construct

<400> SEQUENCE: 256

Asn Thr Cys Gln Pro Thr Lys Asn Ala Thr Pro Cys Ser Ala
1               5                   10

<210> SEQ ID NO 257
<211> LENGTH: 20
<212> TYPE: PRT
<213> ORGANISM: artificial sequence
<220> FEATURE:
<223> OTHER INFORMATION: Synthetic construct

<400> SEQUENCE: 257

Pro Ser Glu Pro Glu Arg Arg Asp Arg Asn Ile Ala Ala Asn Ala Gly
1               5                   10                  15

Arg Phe Asn Thr
            20

<210> SEQ ID NO 258
<211> LENGTH: 18
<212> TYPE: PRT
<213> ORGANISM: artificial sequence
<220> FEATURE:
<223> OTHER INFORMATION: Synthetic construct

<400> SEQUENCE: 258

Thr His Asn Met Ser His Phe Pro Pro Ser Gly His Pro Lys Arg Thr
1               5                   10                  15

Ala Thr

<210> SEQ ID NO 259
<211> LENGTH: 14
<212> TYPE: PRT
<213> ORGANISM: artificial sequence
<220> FEATURE:
<223> OTHER INFORMATION: Synthetic construct

<400> SEQUENCE: 259

Thr Thr Cys Pro Thr Met Gly Thr Tyr His Val Cys Trp Leu
1               5                   10

<210> SEQ ID NO 260
<211> LENGTH: 20
<212> TYPE: PRT
<213> ORGANISM: artificial sequence
<220> FEATURE:

<223> OTHER INFORMATION: Synthetic construct

<400> SEQUENCE: 260

Tyr Cys Ala Asp His Thr Pro Asp Pro Ala Asn Pro Asn Lys Ile Cys
1               5                   10                  15

Gly Tyr Ser His
            20

<210> SEQ ID NO 261
<211> LENGTH: 20
<212> TYPE: PRT
<213> ORGANISM: artificial sequence
<220> FEATURE:
<223> OTHER INFORMATION: Synthetic construct

<400> SEQUENCE: 261

Ala Ala Asn Pro His Thr Glu Trp Asp Arg Asp Ala Phe Gln Leu Ala
1               5                   10                  15

Met Pro Pro Lys
            20

<210> SEQ ID NO 262
<211> LENGTH: 20
<212> TYPE: PRT
<213> ORGANISM: artificial sequence
<220> FEATURE:
<223> OTHER INFORMATION: Synthetic construct

<400> SEQUENCE: 262

Asp Leu His Pro Met Asp Pro Ser Asn Lys Arg Pro Asp Asn Pro Ser
1               5                   10                  15

Asp Leu His Thr
            20

<210> SEQ ID NO 263
<211> LENGTH: 14
<212> TYPE: PRT
<213> ORGANISM: artificial sequence
<220> FEATURE:
<223> OTHER INFORMATION: Synthetic construct

<400> SEQUENCE: 263

Glu Ser Cys Val Ser Asn Ala Leu Met Asn Gln Cys Ile Tyr
1               5                   10

<210> SEQ ID NO 264
<211> LENGTH: 20
<212> TYPE: PRT
<213> ORGANISM: artificial sequence
<220> FEATURE:
<223> OTHER INFORMATION: Synthetic construct

<400> SEQUENCE: 264

His Asn Lys Ala Asp Ser Trp Asp Pro Asp Leu Pro Pro His Ala Gly
1               5                   10                  15

Met Ser Leu Gly
            20

<210> SEQ ID NO 265
<211> LENGTH: 20
<212> TYPE: PRT
<213> ORGANISM: artificial sequence
<220> FEATURE:
<223> OTHER INFORMATION: Synthetic construct

<400> SEQUENCE: 265

Leu Asn Asp Gln Arg Lys Pro Gly Pro Pro Thr Met Pro Thr His Ser
1               5                   10                  15

Pro Ala Val Gly
            20

<210> SEQ ID NO 266
<211> LENGTH: 14
<212> TYPE: PRT
<213> ORGANISM: artificial sequence
<220> FEATURE:
<223> OTHER INFORMATION: Synthetic construct

<400> SEQUENCE: 266

Asn Thr Cys Ala Thr Ser Pro Asn Ser Tyr Thr Cys Ser Asn
1               5                   10

<210> SEQ ID NO 267
<211> LENGTH: 14
<212> TYPE: PRT
<213> ORGANISM: artificial sequence
<220> FEATURE:
<223> OTHER INFORMATION: Synthetic construct

<400> SEQUENCE: 267

Ser Asp Cys Thr Ala Gly Leu Val Pro Pro Leu Cys Ala Thr
1               5                   10

<210> SEQ ID NO 268
<211> LENGTH: 20
<212> TYPE: PRT
<213> ORGANISM: artificial sequence
<220> FEATURE:
<223> OTHER INFORMATION: Synthetic construct

<400> SEQUENCE: 268

Thr Ile Glu Ser Ser Gln His Ser Arg Thr His Gln Gln Asn Tyr Gly
1               5                   10                  15

Ser Thr Lys Thr
            20

<210> SEQ ID NO 269
<211> LENGTH: 20
<212> TYPE: PRT
<213> ORGANISM: artificial sequence
<220> FEATURE:
<223> OTHER INFORMATION: Synthetic construct

<400> SEQUENCE: 269

Val Gly Thr Met Lys Gln His Pro Thr Thr Gln Pro Pro Arg Val
1               5                   10                  15

Ser Ala Thr Asn
            20

<210> SEQ ID NO 270
<211> LENGTH: 20
<212> TYPE: PRT
<213> ORGANISM: artificial sequence
<220> FEATURE:
<223> OTHER INFORMATION: Synthetic construct

<400> SEQUENCE: 270

Tyr Ser Glu Thr Pro Asn Asp Gln Lys Pro Asn Pro His Tyr Lys Val
1               5                   10                  15

Ser Gly Thr Lys
            20

<210> SEQ ID NO 271
<211> LENGTH: 12
<212> TYPE: PRT
<213> ORGANISM: Artificial sequence
<220> FEATURE:
<223> OTHER INFORMATION: Polymethylmethacrylate binding peptides

<400> SEQUENCE: 271

Ile Pro Trp Trp Asn Ile Arg Ala Pro Leu Asn Ala
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 272

Thr Ala Val Met Asn Val Val Asn Asn Gln Leu Ser
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 273

Val Pro Trp Trp Ala Pro Ser Lys Leu Ser Met Gln
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 274

Met Val Met Ala Pro His Thr Pro Arg Ala Arg Ser
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Polymethylmethacrylate-binding peptide

<400> SEQUENCE: 275

Thr Tyr Pro Asn Trp Ala His Leu Leu Ser His Tyr
1               5                   10

<210> SEQ ID NO 276
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 276

Thr Pro Trp Trp Arg Ile Thr
1               5

```
<210> SEQ ID NO 277
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 277

Asp Leu Thr Leu Pro Phe His
1               5

<210> SEQ ID NO 278
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 278

Gly Thr Ser Ile Pro Ala Met
1               5

<210> SEQ ID NO 279
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 279

His His Lys His Val Val Ala
1               5

<210> SEQ ID NO 280
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 280

His His His Lys His Phe Met
1               5

<210> SEQ ID NO 281
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 281

His His His Arg His Gln Gly
1               5

<210> SEQ ID NO 282
<211> LENGTH: 7
<212> TYPE: PRT
<213> ORGANISM: Artificial Sequence
<220> FEATURE:
<223> OTHER INFORMATION: Polymethylmethacrylate-binding peptide

<400> SEQUENCE: 282

His His Trp His Ala Pro Arg
1               5

<210> SEQ ID NO 283
<211> LENGTH: 12
```

```
<212> TYPE: PRT
<213> ORGANISM: Artificial Sequence
<220> FEATURE:
<223> OTHER INFORMATION: Shampoo-resistant, PMMA-binding peptide

<400> SEQUENCE: 283

Ala Pro Trp His Leu Ser Ser Gln Tyr Ser Gly Thr
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Shampoo-resistant PMMA-binding peptide

<400> SEQUENCE: 284

Gly Tyr Cys Leu Arg Val Asp Glu Pro Thr Val Cys Ser Gly
1               5                   10

<210> SEQ ID NO 285
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 285

His Ile His Pro Ser Asp Asn Phe Pro His Lys Asn Arg Thr His
1               5                   10                  15

<210> SEQ ID NO 286
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 286

His Thr His His Asp Thr His Lys Pro Trp Pro Thr Asp Asp His Arg
1               5                   10                  15

Asn Ser Ser Val
            20

<210> SEQ ID NO 287
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 287

Pro Glu Asp Arg Pro Ser Arg Thr Asn Ala Leu His His Asn Ala His
1               5                   10                  15

His His Asn Ala
            20

<210> SEQ ID NO 288
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 288

Thr Pro His Asn His Ala Thr Thr Asn His His Ala Gly Lys Lys
1               5                   10                  15
```

-continued

```
<210> SEQ ID NO 289
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 289

Glu Met Val Lys Asp Ser Asn Gln Arg Asn Thr Arg Ile Ser Ser
1               5                   10                  15

<210> SEQ ID NO 290
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 290

His Tyr Ser Arg Tyr Asn Pro Gly Pro His Pro Leu
1               5                   10

<210> SEQ ID NO 291
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 291

Ile Asp Thr Phe Tyr Met Ser Thr Met Ser His Ser
1               5                   10

<210> SEQ ID NO 292
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 292

Pro Met Lys Glu Ala Thr His Pro Val Pro Pro His Lys His Ser Glu
1               5                   10                  15

Thr Pro Thr Ala
            20

<210> SEQ ID NO 293
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 293

Tyr Gln Thr Ser Ser Pro Ala Lys Gln Ser Val Gly
1               5                   10

<210> SEQ ID NO 294
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 294

His Leu Pro Ser Tyr Gln Ile Thr Gln Thr His Ala Gln Tyr Arg
```

```
1               5                  10                  15
```

<210> SEQ ID NO 295
<211> LENGTH: 20
<212> TYPE: PRT
<213> ORGANISM: Artificial Sequence
<220> FEATURE:
<223> OTHER INFORMATION: Shampoo-resistant PMMA-binding peptide

<400> SEQUENCE: 295

```
Thr Thr Pro Lys Thr Thr Tyr His Gln Ser Arg Ala Pro Val Thr Ala
1               5                  10                  15

Met Ser Glu Val
            20
```

<210> SEQ ID NO 296
<211> LENGTH: 15
<212> TYPE: PRT
<213> ORGANISM: Artificial Sequence
<220> FEATURE:
<223> OTHER INFORMATION: Shampoo-resistant PMMA-binding peptide

<400> SEQUENCE: 296

```
Asp Arg Ile His His Lys Ser His His Val Thr Asn His Phe
1               5                  10                  15
```

<210> SEQ ID NO 297
<211> LENGTH: 12
<212> TYPE: PRT
<213> ORGANISM: Artificial Sequence
<220> FEATURE:
<223> OTHER INFORMATION: Shampoo-resistant PMMA-binding peptide

<400> SEQUENCE: 297

```
Trp Ala Pro Glu Lys Asp Tyr Met Gln Leu Met Lys
1               5                  10
```

<210> SEQ ID NO 298
<211> LENGTH: 12
<212> TYPE: PRT
<213> ORGANISM: Artificial sequence
<220> FEATURE:
<223> OTHER INFORMATION: Polypropylene-binding peptides

<400> SEQUENCE: 298

```
Thr Ser Asp Ile Lys Ser Arg Ser Pro His His Arg
1               5                  10
```

<210> SEQ ID NO 299
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 299

```
His Thr Gln Asn Met Arg Met Tyr Glu Pro Trp Phe
1               5                  10
```

<210> SEQ ID NO 300
<211> LENGTH: 7
<212> TYPE: PRT
<213> ORGANISM: Artificial Sequence
<220> FEATURE:
<223> OTHER INFORMATION: Polypropylene-binding peptide

<400> SEQUENCE: 300

```
Leu Pro Pro Gly Ser Leu Ala
1               5

<210> SEQ ID NO 301
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 301

Met Pro Ala Val Met Ser Ser Ala Gln Val Pro Arg
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 302

Asn Gln Ser Phe Leu Pro Leu Asp Phe Pro Phe Arg
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Polypropylene-binding peptide

<400> SEQUENCE: 303

Ser Ile Leu Ser Thr Met Ser Pro His Gly Ala Thr
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Polypropylenebinding peptide

<400> SEQUENCE: 304

Ser Met Lys Tyr Ser His Ser Thr Ala Pro Ala Leu
1               5                   10

<210> SEQ ID NO 305
<211> LENGTH: 12
<212> TYPE: PRT
<213> ORGANISM: Artificial sequence
<220> FEATURE:
<223> OTHER INFORMATION: Polytetrafluoroethylene-binding peptides

<400> SEQUENCE: 305

Glu Ser Ser Tyr Ser Trp Ser Pro Ala Arg Leu Ser
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 306

Gly Pro Leu Lys Leu Leu His Ala Trp Trp Gln Pro
1               5                   10
```

<210> SEQ ID NO 307
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 307

Asn Ala Leu Thr Arg Pro Val
1               5

<210> SEQ ID NO 308
<211> LENGTH: 7
<212> TYPE: PRT
<213> ORGANISM: Artificial Sequence
<220> FEATURE:
<223> OTHER INFORMATION: Polytetrafluoroethylene-binding peptide

<400> SEQUENCE: 308

Ser Ala Pro Ser Ser Lys Asn
1               5

<210> SEQ ID NO 309
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 309

Ser Val Ser Val Gly Met Lys Pro Ser Pro Arg Pro
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 310

Ser Tyr Tyr Ser Leu Pro Pro Ile Phe His Ile Pro
1               5                   10

<210> SEQ ID NO 311
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 311

Thr Phe Thr Pro Tyr Ser Ile Thr His Ala Leu Leu
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 312

Thr Met Gly Phe Thr Ala Pro Arg Phe Pro His Tyr
1               5                   10

```
<210> SEQ ID NO 313
<211> LENGTH: 12
<212> TYPE: PRT
<213> ORGANISM: Artificial Sequence
<220> FEATURE:
<223> OTHER INFORMATION: Polytetrafluoroethylene-binding peptide

<400> SEQUENCE: 313

Thr Asn Pro Phe Pro Pro Pro Ser Ser Pro Ala
1               5                   10

<210> SEQ ID NO 314
<211> LENGTH: 12
<212> TYPE: PRT
<213> ORGANISM: Artificial sequence
<220> FEATURE:
<223> OTHER INFORMATION: Polyethylene-binding peptides

<400> SEQUENCE: 314

His Asn Lys Ser Ser Pro Leu Thr Ala Ala Leu Pro
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 315

Leu Pro Pro Trp Lys His Lys Thr Ser Gly Val Ala
1               5                   10

<210> SEQ ID NO 316
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 316

Leu Pro Trp Trp Leu Arg Asp Ser Tyr Leu Leu Pro
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 317

Val Pro Trp Trp Lys His Pro Pro Leu Pro Val Pro
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 318

His His Lys Gln Trp His Asn His Pro His His Ala
1               5                   10

<210> SEQ ID NO 319
<211> LENGTH: 12
```

```
<212> TYPE: PRT
<213> ORGANISM: Artificial Sequence
<220> FEATURE:
<223> OTHER INFORMATION: Polyethylene-binding peptide

<400> SEQUENCE: 319

His Ile Phe Ser Ser Trp His Gln Met Trp His Arg
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Polyethylene-binding peptide

<400> SEQUENCE: 320

Trp Pro Ala Trp Lys Thr His Pro Ile Leu Arg Met
1               5                   10

<210> SEQ ID NO 321
<211> LENGTH: 7
<212> TYPE: PRT
<213> ORGANISM: Artificial sequence
<220> FEATURE:
<223> OTHER INFORMATION: Nylon-binding peptides

<400> SEQUENCE: 321

Lys Thr Pro Pro Thr Arg Pro
1               5

<210> SEQ ID NO 322
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 322

Val Ile Asn Pro Asn Leu Asp
1               5

<210> SEQ ID NO 323
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 323

Lys Val Trp Ile Val Ser Thr
1               5

<210> SEQ ID NO 324
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 324

Ala Glu Pro Val Ala Met Leu
1               5

<210> SEQ ID NO 325
<211> LENGTH: 7
<212> TYPE: PRT
<213> ORGANISM: Artificial Sequence
```

```
<220> FEATURE:
<223> OTHER INFORMATION: Nylon-binding peptide

<400> SEQUENCE: 325

Ala Glu Leu Val Ala Met Leu
1               5

<210> SEQ ID NO 326
<211> LENGTH: 7
<212> TYPE: PRT
<213> ORGANISM: Artificial Sequence
<220> FEATURE:
<223> OTHER INFORMATION: Nylon-binding peptide

<400> SEQUENCE: 326

His Ser Leu Arg Leu Asp Trp
1               5

<210> SEQ ID NO 327
<211> LENGTH: 13
<212> TYPE: PRT
<213> ORGANISM: Artificial sequence
<220> FEATURE:
<223> OTHER INFORMATION: Polystyrene-binding peptide

<400> SEQUENCE: 327

Thr Ser Thr Ala Ser Pro Thr Met Gln Ser Lys Ile Arg
1               5                   10

<210> SEQ ID NO 328
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 328

Lys Arg Asn His Trp Gln Arg Met His Leu Ser Ala
1               5                   10

<210> SEQ ID NO 329
<211> LENGTH: 12
<212> TYPE: PRT
<213> ORGANISM: Artificial Sequence
<220> FEATURE:
<223> OTHER INFORMATION: Polystyrene-binding peptide

<400> SEQUENCE: 329

Ser His Ala Thr Pro Pro Gln Gly Leu Gly Pro Gln
1               5                   10

<210> SEQ ID NO 330
<211> LENGTH: 20
<212> TYPE: PRT
<213> ORGANISM: artificial sequence
<220> FEATURE:
<223> OTHER INFORMATION: cellulose acetate-binding peptide

<400> SEQUENCE: 330

Ala Thr Thr Pro Pro Ser Gly Lys Ala Ala Ala His Ser Ala Ala Arg
1               5                   10                  15

Gln Lys Gly Asn
            20

<210> SEQ ID NO 331
<211> LENGTH: 15
<212> TYPE: PRT
```

<213> ORGANISM: artificial sequence
<220> FEATURE:
<223> OTHER INFORMATION: cellulose acetate-binding peptide

<400> SEQUENCE: 331

Asp Thr Ile His Pro Asn Lys Met Lys Ser Pro Ser Ser Pro Leu
1               5                   10                  15

<210> SEQ ID NO 332
<211> LENGTH: 20
<212> TYPE: PRT
<213> ORGANISM: artificial sequence
<220> FEATURE:
<223> OTHER INFORMATION: cellulose aceteate-binding peptide

<400> SEQUENCE: 332

Asn Gly Asn Asn His Thr Asp Ile Pro Asn Arg Ser Ser Tyr Thr Gly
1               5                   10                  15

Gly Ser Phe Ala
            20

<210> SEQ ID NO 333
<211> LENGTH: 15
<212> TYPE: PRT
<213> ORGANISM: ARTIFICIAL SEQUENCE
<220> FEATURE:
<223> OTHER INFORMATION: synthetic cellulose acetate-binding peptide

<400> SEQUENCE: 333

Ser Asp Glu Thr Gly Pro Gln Ile Pro His Arg Arg Pro Thr Trp
1               5                   10                  15

<210> SEQ ID NO 334
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 334

Met Pro Pro Pro Leu Met Gln
1               5

<210> SEQ ID NO 335
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 335

Phe His Glu Asn Trp Pro Ser
1               5

<210> SEQ ID NO 336
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 336

Arg Thr Ala Pro Thr Thr Pro Leu Leu Leu Ser Leu
1               5                   10

<210> SEQ ID NO 337
<211> LENGTH: 12

```
<212> TYPE: PRT
<213> ORGANISM: Artificial Sequence
<220> FEATURE:
<223> OTHER INFORMATION: Pigment-binding peptide

<400> SEQUENCE: 337

Trp His Leu Ser Trp Ser Pro Val Pro Leu Pro Thr
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 338

Pro His Ala Arg Leu Val Gly
1               5

<210> SEQ ID NO 339
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 339

Asn Ile Pro Tyr His His Pro
1               5

<210> SEQ ID NO 340
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 340

Thr Thr Met Pro Ala Ile Pro
1               5

<210> SEQ ID NO 341
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 341

His Asn Leu Pro Pro Arg Ser
1               5

<210> SEQ ID NO 342
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 342

Ala His Lys Thr Gln Met Gly Val Arg Gln Pro Ala
1               5                   10

<210> SEQ ID NO 343
<211> LENGTH: 12
<212> TYPE: PRT
<213> ORGANISM: Artificial Sequence
```

```
<220> FEATURE:
<223> OTHER INFORMATION: Pigment-binding peptide

<400> SEQUENCE: 343

Ala Asp Asn Val Gln Met Gly Val Ser His Thr Pro
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 344

Ala His Asn Ala Gln Met Gly Val Ser His Pro Pro
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 345

Ala Asp Tyr Val Gly Met Gly Val Ser His Arg Pro
1               5                   10

<210> SEQ ID NO 346
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 346

Ser Val Ser Val Gly Met Lys Pro Ser Pro Arg Pro
1               5                   10

<210> SEQ ID NO 347
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 347

Tyr Pro Asn Thr Ala Leu Val
1               5

<210> SEQ ID NO 348
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 348

Val Ala Thr Arg Ile Val Ser
1               5

<210> SEQ ID NO 349
<211> LENGTH: 12
<212> TYPE: PRT
<213> ORGANISM: Artificial Sequence
<220> FEATURE:
<223> OTHER INFORMATION: Pigment-binding peptide
```

```
<400> SEQUENCE: 349

His Ser Leu Lys Asn Ser Met Leu Thr Val Met Ala
1               5                   10

<210> SEQ ID NO 350
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 350

Asn Tyr Pro Thr Gln Ala Pro
1               5

<210> SEQ ID NO 351
<211> LENGTH: 7
<212> TYPE: PRT
<213> ORGANISM: Artificial Sequence
<220> FEATURE:
<223> OTHER INFORMATION: Pigment-binding peptide

<400> SEQUENCE: 351

Lys Cys Cys Tyr Ser Val Gly
1               5

<210> SEQ ID NO 352
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 352

Arg His Asp Leu Asn Thr Trp Leu Pro Pro Val Lys
1               5                   10

<210> SEQ ID NO 353
<211> LENGTH: 12
<212> TYPE: PRT
<213> ORGANISM: artificial sequence
<220> FEATURE:
<223> OTHER INFORMATION: Pigment-binding peptide

<400> SEQUENCE: 353

Glu Ile Ser Leu Pro Ala Lys Leu Pro Ser Ala Ser
1               5                   10

<210> SEQ ID NO 354
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 354

Ser Asp Tyr Val Gly Met Arg Pro Ser Pro Arg His
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 355
```

```
Ser Asp Tyr Val Gly Met Arg Leu Ser Pro Ser Gln
1               5                   10
```

<210> SEQ ID NO 356
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 356

```
Ser Val Ser Val Gly Ile Gln Pro Ser Pro Arg Pro
1               5                   10
```

<210> SEQ ID NO 357
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 357

```
Tyr Val Ser Val Gly Ile Lys Pro Ser Pro Arg Pro
1               5                   10
```

<210> SEQ ID NO 358
<211> LENGTH: 12
<212> TYPE: PRT
<213> ORGANISM: Artificial Sequence
<220> FEATURE:
<223> OTHER INFORMATION: Pigment-binding peptide

<400> SEQUENCE: 358

```
Tyr Val Cys Glu Gly Ile His Pro Cys Pro Arg Pro
1               5                   10
```

<210> SEQ ID NO 359
<211> LENGTH: 12
<212> TYPE: PRT
<213> ORGANISM: artificial sequence
<220> FEATURE:
<223> OTHER INFORMATION: synthetic iron oxide pigment binding peptide

<400> SEQUENCE: 359

```
Trp Ala Pro Glu Lys Asp His Met Gln Leu Met Lys
1               5                   10
```

<210> SEQ ID NO 360
<211> LENGTH: 12
<212> TYPE: PRT
<213> ORGANISM: artificial sequence
<220> FEATURE:
<223> OTHER INFORMATION: Iron oxide-binding peptide

<400> SEQUENCE: 360

```
Trp Ala Pro Glu Lys Asp Tyr Met Gln Leu Met Lys
1               5                   10
```

<210> SEQ ID NO 361
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 361

```
Cys Pro Leu Asp Thr Pro Thr His Lys Thr Lys His Glu Tyr Lys Thr
```

```
                1               5                  10                  15
Arg Cys Arg His
            20

<210> SEQ ID NO 362
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 362

Asp His Asp His Pro Arg Leu His Lys Arg Gln Glu Lys Ser Glu His
1               5                  10                  15

Leu His

<210> SEQ ID NO 363
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 363

Asp Ser His His Asn His His Lys Gln Asp Ser Arg Pro Gln His Arg
1               5                  10                  15

Lys Thr Pro Asn
            20

<210> SEQ ID NO 364
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 364

Glu Gly Gly Asn Ala Pro His His Lys Pro His His Arg Lys His
1               5                  10                  15

<210> SEQ ID NO 365
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 365

His Asp Ser His Arg Pro Leu Thr Gln His Gly His Arg His Ser His
1               5                  10                  15

Val Pro

<210> SEQ ID NO 366
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 366

His Asp Ser Asn His Cys Ser His Ser Thr Arg Arg Pro Asn Cys Ala
1               5                  10                  15

Arg Thr
```

```
<210> SEQ ID NO 367
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 367

Ala Thr Arg Val Asp Asn Thr Pro Ala Ser Asn Pro Pro Ser Leu
1               5                   10                  15

<210> SEQ ID NO 368
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 368

Asp Gly Ile Lys Pro Phe His Leu Met Thr Pro Thr Leu Ala Asn
1               5                   10                  15

<210> SEQ ID NO 369
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 369

Asp Ile Thr Pro Pro Gly Ser Thr His His Arg Lys Pro His Arg His
1               5                   10                  15

Gln His

<210> SEQ ID NO 370
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 370

Asp Asn Leu Trp Pro Gln Pro Leu Asn Val Glu Asp Asp Arg Tyr
1               5                   10                  15

<210> SEQ ID NO 371
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 371

Glu Asn Glu Lys His Arg His Asn Thr His Glu Ala Leu His Ser His
1               5                   10                  15

Phe Lys

<210> SEQ ID NO 372
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 372

Gly Ala Ile Trp Pro Ala Ser Ser Ala Leu Met Thr Glu His Asn Pro
1               5                   10                  15
```

```
Thr Asp Asn His
        20

<210> SEQ ID NO 373
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 373

Gly Asp Thr Asn Gln Asp Thr Val Met Trp Tyr Tyr Thr Val Asn
1               5                   10                  15

<210> SEQ ID NO 374
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 374

His Asn Gly Pro Tyr Gly Met Leu Ser Thr Gly Lys Ile His Phe
1               5                   10                  15

<210> SEQ ID NO 375
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 375

Leu Asp Gly Gly Tyr Arg Asp Thr Pro Asp Asn Tyr Leu Lys Gly
1               5                   10                  15

<210> SEQ ID NO 376
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 376

Leu His Thr Lys Thr Glu Asn Ser His Thr Asn Met Lys Thr Thr
1               5                   10                  15

<210> SEQ ID NO 377
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 377

Asn Ala Gln Tyr Asp Pro Pro Thr Leu Asn Lys Gly Ala Val Arg Lys
1               5                   10                  15

Ala Ala Ser Thr
        20

<210> SEQ ID NO 378
<211> LENGTH: 15
<212> TYPE: PRT
<213> ORGANISM: artificial sequence
<220> FEATURE:
<223> OTHER INFORMATION: Iron oxide-binding peptide
```

```
<400> SEQUENCE: 378

Asn Gly Asn Asn His Thr Asp Ile Pro Asn Arg Ser Ser Tyr Thr
1               5                  10                  15

<210> SEQ ID NO 379
<211> LENGTH: 18
<212> TYPE: PRT
<213> ORGANISM: artificial sequence
<220> FEATURE:
<223> OTHER INFORMATION: Iron oxide-binding peptide

<400> SEQUENCE: 379

Gln Ser Thr Asn His His His Pro His Ala Lys His Pro Arg Val Asn
1               5                  10                  15

Thr His

<210> SEQ ID NO 380
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 380

Ser Asn Asn Asp Tyr Val Gly Thr Tyr Pro Ala Thr Ala Ile Gln
1               5                  10                  15

<210> SEQ ID NO 381
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 381

Ser Thr Gln His Asn Leu His Asp Arg Asn Ile Tyr Phe Val Ser
1               5                  10                  15

<210> SEQ ID NO 382
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 382

Thr Ala Asn Asn Lys Thr Pro Ala Gly Ala Pro Asn Ala Ala Val Gly
1               5                  10                  15

Leu Ala Gln Arg
            20

<210> SEQ ID NO 383
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 383

Thr Glu Pro Thr Arg Ile Ser Asn Tyr Arg Ser Ile Pro Asn Asp
1               5                  10                  15

<210> SEQ ID NO 384
<211> LENGTH: 18
<212> TYPE: PRT
<213> ORGANISM: artificial sequence
```

```
<220> FEATURE:
<223> OTHER INFORMATION: Iron oxide-binding peptide

<400> SEQUENCE: 384

Thr His Asn Pro Arg Glu His Ala Arg His His His Asn Glu Tyr
1               5                   10                  15

Lys His

<210> SEQ ID NO 385
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 385

Thr His Pro Pro Cys Trp Tyr Glu Thr Asn Cys Ile Val Gln Glu
1               5                   10                  15

<210> SEQ ID NO 386
<211> LENGTH: 20
<212> TYPE: PRT
<213> ORGANISM: artificial sequence
<220> FEATURE:
<223> OTHER INFORMATION: Iron oxide-binding peptide

<400> SEQUENCE: 386

Thr Thr Asn Pro His Lys Pro Ala Ser His His Asp His Arg Pro
1               5                   10                  15

Ala Leu Arg His
            20

<210> SEQ ID NO 387
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 387

Trp Leu Val Ala Asp Asn Ala Thr Asp Gly His Ser His Gln Lys
1               5                   10                  15

<210> SEQ ID NO 388
<211> LENGTH: 15
<212> TYPE: PRT
<213> ORGANISM: artificial sequence
<220> FEATURE:
<223> OTHER INFORMATION: Iron oxide-binding peptide

<400> SEQUENCE: 388

Tyr Thr Asp Ser Met Ser Asp Gln Thr Pro Glu Phe Ala Lys Tyr
1               5                   10                  15

<210> SEQ ID NO 389
<211> LENGTH: 7
<212> TYPE: PRT
<213> ORGANISM: Artificial Sequence
<220> FEATURE:
<223> OTHER INFORMATION: Print Media Binding Peptide

<400> SEQUENCE: 389

Ser Ile Leu Pro Tyr Pro Tyr
1               5

<210> SEQ ID NO 390
```

```
<211> LENGTH: 7
<212> TYPE: PRT
<213> ORGANISM: Artificial Sequence
<220> FEATURE:
<223> OTHER INFORMATION: Cotton Binding Peptide

<400> SEQUENCE: 390

Ser Thr Ala Ser Tyr Thr Arg
1               5

<210> SEQ ID NO 391
<211> LENGTH: 7
<212> TYPE: PRT
<213> ORGANISM: Artificial Sequence
<220> FEATURE:
<223> OTHER INFORMATION: Polyester/Cotton Binding Peptide

<400> SEQUENCE: 391

Leu Pro Val Arg Pro Trp Thr
1               5

<210> SEQ ID NO 392
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 392

Gly Asn Thr Pro Ser Arg Ala
1               5

<210> SEQ ID NO 393
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 393

His Ala Ile Tyr Pro Arg His
1               5

<210> SEQ ID NO 394
<211> LENGTH: 7
<212> TYPE: PRT
<213> ORGANISM: Artificial Sequence
<220> FEATURE:
<223> OTHER INFORMATION: Paper Binding Peptide

<400> SEQUENCE: 394

Tyr Gln Asp Ser Ala Lys Thr
1               5

<210> SEQ ID NO 395
<211> LENGTH: 7
<212> TYPE: PRT
<213> ORGANISM: Artificial Sequence
<220> FEATURE:
<223> OTHER INFORMATION: Cellulose Binding Peptide

<400> SEQUENCE: 395

Val Pro Arg Val Thr Ser Ile
1               5

<210> SEQ ID NO 396
<211> LENGTH: 7
<212> TYPE: PRT
```

```
<213> ORGANISM: Artificial Sequence
<220> FEATURE:
<223> OTHER INFORMATION: Cellulose Binding Peptide

<400> SEQUENCE: 396

Met Ala Asn His Asn Leu Ser
1               5

<210> SEQ ID NO 397
<211> LENGTH: 7
<212> TYPE: PRT
<213> ORGANISM: Artificial Sequence
<220> FEATURE:
<223> OTHER INFORMATION: Pigment Binding and Cellulose Binding Peptide

<400> SEQUENCE: 397

Phe His Glu Asn Trp Pro Ser
1               5

<210> SEQ ID NO 398
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 398

Thr His Lys Thr Ser Thr Gln Arg Leu Leu Ala Ala
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 399

Lys Cys Cys Tyr Val Asn Val Gly Ser Val Phe Ser
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Cellulose Binding Peptide

<400> SEQUENCE: 400

Ala His Met Gln Phe Arg Thr Ser Leu Thr Pro His
1               5                   10

<210> SEQ ID NO 401
<211> LENGTH: 27
<212> TYPE: PRT
<213> ORGANISM: artificial sequence
<220> FEATURE:
<223> OTHER INFORMATION: Clay-binding peptide

<400> SEQUENCE: 401

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 402
<211> LENGTH: 27
```

```
<212> TYPE: PRT
<213> ORGANISM: artificial sequence
<220> FEATURE:
<223> OTHER INFORMATION: Clay-binding peptide

<400> SEQUENCE: 402

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25

<210> SEQ ID NO 403
<211> LENGTH: 27
<212> TYPE: PRT
<213> ORGANISM: artificial sequence
<220> FEATURE:
<223> OTHER INFORMATION: Clay-binding peptide

<400> SEQUENCE: 403

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 404
<211> LENGTH: 27
<212> TYPE: PRT
<213> ORGANISM: artificial sequence
<220> FEATURE:
<223> OTHER INFORMATION: Clay-binding peptide

<400> SEQUENCE: 404

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 405
<211> LENGTH: 22
<212> TYPE: PRT
<213> ORGANISM: artificial sequence
<220> FEATURE:
<223> OTHER INFORMATION: Clay-binding peptide

<400> SEQUENCE: 405

Val Gly Arg His His Ser Lys Ala Lys Gln Lys Arg Pro His Gly Gly
1               5                   10                  15

Lys Gly Gln Asn Lys Asn
            20

<210> SEQ ID NO 406
<211> LENGTH: 22
<212> TYPE: PRT
<213> ORGANISM: artificial sequence
<220> FEATURE:
<223> OTHER INFORMATION: Clay-binding peptide

<400> SEQUENCE: 406

Val Gly Arg His His Pro Lys Ala Lys Gln Lys Arg Pro His Gly Gly
1               5                   10                  15

Lys Gly Gln Asn Lys Asn
            20

<210> SEQ ID NO 407
<211> LENGTH: 17
```

```
<212> TYPE: PRT
<213> ORGANISM: artificial sequence
<220> FEATURE:
<223> OTHER INFORMATION: Clay-binding peptide

<400> SEQUENCE: 407

Gly Arg Arg Pro Arg Ala Arg Gly Arg Ser Arg Arg Gly Ser Thr Lys
1               5                   10                  15

Thr

<210> SEQ ID NO 408
<211> LENGTH: 19
<212> TYPE: PRT
<213> ORGANISM: artificial sequence
<220> FEATURE:
<223> OTHER INFORMATION: Clay-binding peptide

<400> SEQUENCE: 408

Leu Gly Val Ile Arg Asn His Val Val Arg Gly Arg Arg His His Gln
1               5                   10                  15

His Val Arg

<210> SEQ ID NO 409
<211> LENGTH: 27
<212> TYPE: PRT
<213> ORGANISM: artificial sequence
<220> FEATURE:
<223> OTHER INFORMATION: Clay-binding peptide

<400> SEQUENCE: 409

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 410
<211> LENGTH: 27
<212> TYPE: PRT
<213> ORGANISM: artificial sequence
<220> FEATURE:
<223> OTHER INFORMATION: Clay-binding peptide

<400> SEQUENCE: 410

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 411
<211> LENGTH: 27
<212> TYPE: PRT
<213> ORGANISM: artificial sequence
<220> FEATURE:
<223> OTHER INFORMATION: Clay-binding peptide

<400> SEQUENCE: 411

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 412
<211> LENGTH: 27
<212> TYPE: PRT
<213> ORGANISM: artificial sequence
```

```
<220> FEATURE:
<223> OTHER INFORMATION: Clay-binding peptide

<400> SEQUENCE: 412

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25

<210> SEQ ID NO 413
<211> LENGTH: 27
<212> TYPE: PRT
<213> ORGANISM: artificial sequence
<220> FEATURE:
<223> OTHER INFORMATION: Clay-binding peptide

<400> SEQUENCE: 413

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 414
<211> LENGTH: 27
<212> TYPE: PRT
<213> ORGANISM: artificial sequence
<220> FEATURE:
<223> OTHER INFORMATION: Clay-binding peptide

<400> SEQUENCE: 414

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 415
<211> LENGTH: 27
<212> TYPE: PRT
<213> ORGANISM: artificial sequence
<220> FEATURE:
<223> OTHER INFORMATION: Clay-binding peptide

<400> SEQUENCE: 415

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 416
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 416

Arg Asn Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 417
<211> LENGTH: 27
<212> TYPE: PRT
<213> ORGANISM: artificial sequence
```

```
<220> FEATURE:
<223> OTHER INFORMATION: Calcium carbonate binding peptide

<400> SEQUENCE: 417

Arg Asn Asn Lys Gly Ser Lys Lys Val Asp Asp Lys Arg Arg Lys Thr
1               5                   10                  15

Val His Asn Thr Lys Ser Arg Ala Lys His Ser
            20                  25

<210> SEQ ID NO 418
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 418

Arg Asp Asn Lys Gly Ser Lys Lys Val Asp Asp Lys Arg Arg Lys Thr
1               5                   10                  15

Val His Asn Thr Lys Ser Arg Ala Lys Tyr Ser
            20                  25

<210> SEQ ID NO 419
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 419

Arg Asn Asn Lys Gly Ser Lys Lys Val Asp Asp Lys Arg Arg Lys Thr
1               5                   10                  15

Val His Ser Thr Lys Ser Arg Ala Lys Tyr Ser
            20                  25

<210> SEQ ID NO 420
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 420

Arg Asn Asn Lys Gly Ser Arg Lys Val Asp Asp Lys Arg Arg Lys Thr
1               5                   10                  15

Val His Asn Thr Lys Ser Arg Ala Lys Tyr Ser
            20                  25

<210> SEQ ID NO 421
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 421

Arg Asn Asn Lys Gly Ser Lys Lys Ala Asp Asp Lys Arg Arg Lys Thr
1               5                   10                  15

Val His Ser Thr Lys Ser Arg Ala Lys Tyr Ser
            20                  25

<210> SEQ ID NO 422
<211> LENGTH: 27
<212> TYPE: PRT
<213> ORGANISM: artificial sequence
```

```
<220> FEATURE:
<223> OTHER INFORMATION: Calcium carbonate binding peptide

<400> SEQUENCE: 422

Arg Asn Asn Lys Gly Ser Lys Lys Val Asp Asp Lys Arg Arg Lys Ala
1               5                   10                  15
Val His Asn Lys Lys Ser Arg Ala Lys Tyr Ser
            20                  25

<210> SEQ ID NO 423
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 423

Arg Asn Asn Lys Gly Ser Lys Lys Val Asp Asp Lys Arg Arg Lys Thr
1               5                   10                  15
Val His Asn Thr Arg Ser Arg Ala Lys Tyr Ser
            20                  25

<210> SEQ ID NO 424
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 424

Arg Asn Asn Lys Gly Ser Lys Lys Val Asp Asp Lys Arg Arg Lys Thr
1               5                   10                  15
Val His Asn Thr Lys Ser Arg Ala Lys Phe Ser
            20                  25

<210> SEQ ID NO 425
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 425

Gln Arg Arg Lys Leu Arg His Pro Lys Glu Lys Trp Phe Gly Trp Ser
1               5                   10                  15
Glu Lys Lys Val Ile Lys Lys Trp Ser Arg Lys
            20                  25

<210> SEQ ID NO 426
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (23)..(23)
<223> OTHER INFORMATION: Xaa = any naturally occurring amino acid

<400> SEQUENCE: 426

Gln Arg Arg Lys Phe Arg His Pro Lys Glu Lys Trp Phe Gly Trp Ser
1               5                   10                  15
Glu Lys Lys Val Ile Lys Xaa Asn Gly Arg Pro
            20                  25
```

```
<210> SEQ ID NO 427
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 427

His Lys Arg Leu Val Gln Asn Lys Pro His Arg Thr Arg Lys Ile Glu
1               5                   10                  15

Gly Trp Ile Lys His Met Val Lys Arg Gln His
            20                  25

<210> SEQ ID NO 428
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 428

Thr Arg Gly His Ile Met Arg Pro Cys Trp Ile Gly Ala Met Lys Gln
1               5                   10                  15

Gly Val Lys Lys Lys Arg Thr Pro Gly Trp Arg
            20                  25

<210> SEQ ID NO 429
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 429

Trp Lys Val Lys Arg Arg Met Val Thr Arg Thr Tyr Glu Phe Met Gly
1               5                   10                  15

Lys Lys Pro Cys Met Met Leu Thr Lys Arg Leu
            20                  25

<210> SEQ ID NO 430
<211> LENGTH: 26
<212> TYPE: PRT
<213> ORGANISM: artificial sequence
<220> FEATURE:
<223> OTHER INFORMATION: Calcium carbonate binding peptide

<400> SEQUENCE: 430

Lys Lys Ser Asn Lys Gly His His Ser Lys Ala Lys Gln Lys Arg Pro
1               5                   10                  15

His Gly Gly Lys Ala Gln Asn Lys Asn Thr
            20                  25

<210> SEQ ID NO 431
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 431

Arg Ala His Lys Glu Arg Phe Val Val Arg Gln Ile Gly Arg Ser Gln
1               5                   10                  15

Gly Tyr Lys Thr Trp Gln Cys Val Arg Val Ala
            20                  25
```

```
<210> SEQ ID NO 432
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 432

Ser Gln Lys Pro Lys Gly His Lys Val Lys Val Val Val Lys Leu Cys
1               5                   10                  15

Lys Arg Pro Tyr Trp Arg Met Leu Asn Thr Ala
            20                  25

<210> SEQ ID NO 433
<211> LENGTH: 27
<212> TYPE: PRT
<213> ORGANISM: artificial sequence
<220> FEATURE:
<223> OTHER INFORMATION: Calcium carbonate binding peptide
<220> FEATURE:
<221> NAME/KEY: MISC_FEATURE
<222> LOCATION: (11)..(11)
<223> OTHER INFORMATION: Xaa = any naturally occurring amino acid

<400> SEQUENCE: 433

Asn His Gly Cys Pro Val Asn Trp Lys Val Xaa Asn Pro Pro Arg Gly
1               5                   10                  15

Trp Gln Arg Leu Asn His Cys Lys Trp Trp Asn
            20                  25

<210> SEQ ID NO 434
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 434

Arg Asn Ser Arg His Lys Glu Trp Arg Arg Tyr Lys Arg Thr His Val
1               5                   10                  15

His Ser His Glu Phe Tyr His Val Glu Cys Trp
            20                  25

<210> SEQ ID NO 435
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 435

His Arg Ser Glu Lys Pro Lys Asn Val Asn Tyr Lys Arg Gly Tyr Trp
1               5                   10                  15

Glu Arg Gly Asn Gln Lys Lys His Gly Pro Gly
            20                  25

<210> SEQ ID NO 436
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 436

His Glu Arg Thr Arg Arg Gly Lys Pro Asp Arg Gln Lys Thr Thr His
1               5                   10                  15
```

```
Glu Lys Arg Arg Gln Gly Leu Trp Ile Phe Met
            20                  25

<210> SEQ ID NO 437
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 437

Pro Trp Gly Thr Asn Lys Arg Gln Lys His Lys Val His Glu Ala Lys
1               5                   10                  15

Ala Leu Lys Lys Ser Leu Trp Tyr Ser Asn Ser
            20                  25

<210> SEQ ID NO 438
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 438

Arg Arg Gly Val Val Leu Cys His Thr His Arg Asn Lys Arg Ile Arg
1               5                   10                  15

Leu Ala Tyr Ser Val Thr Lys Lys Ala Trp Ala
            20                  25

<210> SEQ ID NO 439
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 439

Glu Arg Ile Arg Trp Arg Arg Leu Ser Ala Glu Ile Arg Ala His Lys
1               5                   10                  15

Trp Ser Val Leu Lys Phe Arg Leu Ser Cys Met
            20                  25

<210> SEQ ID NO 440
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 440

Lys Thr Lys Glu Lys Lys Glu Val Lys Leu His Lys Lys Ser Leu
1               5                   10                  15

Ser Leu Val Leu Leu Ala Asp Leu Trp Arg Leu
            20                  25

<210> SEQ ID NO 441
<211> LENGTH: 27
<212> TYPE: PRT
<213> ORGANISM: artificial sequence
<220> FEATURE:
<223> OTHER INFORMATION: Calcium carbonate binding peptide

<400> SEQUENCE: 441

Leu Gly Lys Lys His Lys Gln His Ser Lys Val Gly His Gly Lys Leu
1               5                   10                  15
```

Ser Thr Arg Phe Leu Arg Arg Ser Lys Leu Phe
            20                  25

<210> SEQ ID NO 442
<211> LENGTH: 17
<212> TYPE: PRT
<213> ORGANISM: artificial sequence
<220> FEATURE:
<223> OTHER INFORMATION: Antimicrobial peptide

<400> SEQUENCE: 442

Pro Lys Gly Leu Lys Lys Leu Leu Lys Gly Leu Lys Lys Leu Leu Lys
1               5                   10                  15

Leu

<210> SEQ ID NO 443
<211> LENGTH: 16
<212> TYPE: PRT
<213> ORGANISM: artificial sequence
<220> FEATURE:
<223> OTHER INFORMATION: Antimicrobial peptide

<400> SEQUENCE: 443

Lys Gly Leu Lys Lys Leu Leu Lys Gly Leu Lys Lys Leu Leu Lys Leu
1               5                   10                  15

<210> SEQ ID NO 444
<211> LENGTH: 16
<212> TYPE: PRT
<213> ORGANISM: artificial sequence
<220> FEATURE:
<223> OTHER INFORMATION: Antimicrobial peptide

<400> SEQUENCE: 444

Lys Gly Leu Lys Lys Leu Leu Lys Leu Leu Lys Lys Leu Leu Lys Leu
1               5                   10                  15

<210> SEQ ID NO 445
<211> LENGTH: 14
<212> TYPE: PRT
<213> ORGANISM: artificial sequence
<220> FEATURE:
<223> OTHER INFORMATION: Antimicrobial peptide

<400> SEQUENCE: 445

Leu Lys Lys Leu Leu Lys Leu Leu Lys Lys Leu Leu Lys Leu
1               5                   10

<210> SEQ ID NO 446
<211> LENGTH: 12
<212> TYPE: PRT
<213> ORGANISM: artificial sequence
<220> FEATURE:
<223> OTHER INFORMATION: Antimicrobial peptide

<400> SEQUENCE: 446

Leu Lys Lys Leu Leu Lys Leu Leu Lys Lys Leu Leu
1               5                   10

<210> SEQ ID NO 447
<211> LENGTH: 17
<212> TYPE: PRT
<213> ORGANISM: artificial sequence
<220> FEATURE:
<223> OTHER INFORMATION: Antimicrobial peptide

<400> SEQUENCE: 447

Val Ala Lys Lys Leu Ala Lys Leu Ala Lys Lys Leu Ala Lys Leu Ala
1               5                   10                  15

Leu

<210> SEQ ID NO 448
<211> LENGTH: 13
<212> TYPE: PRT
<213> ORGANISM: artificial sequence
<220> FEATURE:
<223> OTHER INFORMATION: Antimicrobial peptide

<400> SEQUENCE: 448

Phe Ala Lys Leu Leu Ala Lys Ala Leu Lys Lys Leu Leu
1               5                   10

<210> SEQ ID NO 449
<211> LENGTH: 16
<212> TYPE: PRT
<213> ORGANISM: artificial sequence
<220> FEATURE:
<223> OTHER INFORMATION: Antimicrobial peptide

<400> SEQUENCE: 449

Lys Gly Leu Lys Lys Gly Leu Lys Leu Leu Lys Leu Leu Lys Lys Leu
1               5                   10                  15

<210> SEQ ID NO 450
<211> LENGTH: 16
<212> TYPE: PRT
<213> ORGANISM: artificial sequence
<220> FEATURE:
<223> OTHER INFORMATION: Antimicrobial peptide

<400> SEQUENCE: 450

Lys Gly Leu Lys Lys Leu Leu Lys Leu Gly Lys Lys Leu Leu Lys Leu
1               5                   10                  15

<210> SEQ ID NO 451
<211> LENGTH: 16
<212> TYPE: PRT
<213> ORGANISM: artificial sequence
<220> FEATURE:
<223> OTHER INFORMATION: Antimicrobial peptide

<400> SEQUENCE: 451

Lys Gly Leu Lys Lys Leu Gly Lys Leu Leu Lys Lys Leu Leu Lys Leu
1               5                   10                  15

<210> SEQ ID NO 452
<211> LENGTH: 16
<212> TYPE: PRT
<213> ORGANISM: artificial sequence
<220> FEATURE:
<223> OTHER INFORMATION: Antimicrobial peptide

<400> SEQUENCE: 452

Lys Gly Leu Lys Lys Leu Leu Lys Leu Leu Lys Lys Gly Leu Lys Leu
1               5                   10                  15

<210> SEQ ID NO 453
<211> LENGTH: 16
<212> TYPE: PRT
<213> ORGANISM: artificial sequence
<220> FEATURE:
<223> OTHER INFORMATION: Antimicrobial peptide

<400> SEQUENCE: 453

```
Lys Gly Leu Lys Lys Leu Leu Lys Leu Lys Lys Leu Gly Lys Leu
1               5                   10                  15
```

<210> SEQ ID NO 454
<211> LENGTH: 19
<212> TYPE: PRT
<213> ORGANISM: artificial sequence
<220> FEATURE:
<223> OTHER INFORMATION: Antimicrobial peptide

<400> SEQUENCE: 454

```
Phe Ala Leu Ala Leu Lys Ala Leu Lys Lys Leu Lys Lys Ala Leu Lys
1               5                   10                  15

Lys Ala Leu
```

<210> SEQ ID NO 455
<211> LENGTH: 17
<212> TYPE: PRT
<213> ORGANISM: artificial sequence
<220> FEATURE:
<223> OTHER INFORMATION: Antimicrobial peptide

<400> SEQUENCE: 455

```
Phe Ala Lys Lys Leu Ala Lys Leu Ala Lys Lys Leu Ala Lys Leu Ala
1               5                   10                  15

Leu
```

<210> SEQ ID NO 456
<211> LENGTH: 13
<212> TYPE: PRT
<213> ORGANISM: artificial sequence
<220> FEATURE:
<223> OTHER INFORMATION: Antimicrobial peptide

<400> SEQUENCE: 456

```
Phe Ala Lys Leu Leu Ala Lys Leu Ala Lys Lys Leu Leu
1               5                   10
```

<210> SEQ ID NO 457
<211> LENGTH: 15
<212> TYPE: PRT
<213> ORGANISM: artificial sequence
<220> FEATURE:
<223> OTHER INFORMATION: Antimicrobial peptide

<400> SEQUENCE: 457

```
Phe Ala Lys Lys Leu Ala Lys Leu Ala Leu Lys Leu Ala Lys Leu
1               5                   10                  15
```

<210> SEQ ID NO 458
<211> LENGTH: 10
<212> TYPE: PRT
<213> ORGANISM: artificial sequence
<220> FEATURE:
<223> OTHER INFORMATION: Antimicrobial peptide

<400> SEQUENCE: 458

```
Phe Ala Lys Lys Leu Ala Lys Lys Leu Leu
1               5                   10
```

<210> SEQ ID NO 459
<211> LENGTH: 13
<212> TYPE: PRT
<213> ORGANISM: artificial sequence
<220> FEATURE:
<223> OTHER INFORMATION: Antimicrobial peptide

<400> SEQUENCE: 459

Phe Ala Lys Leu Leu Ala Lys Leu Ala Lys Lys Val Leu
1               5                   10

<210> SEQ ID NO 460
<211> LENGTH: 13
<212> TYPE: PRT
<213> ORGANISM: artificial sequence
<220> FEATURE:
<223> OTHER INFORMATION: Antimicrobial peptide

<400> SEQUENCE: 460

Lys Tyr Lys Lys Ala Leu Lys Lys Leu Ala Lys Leu Leu
1               5                   10

<210> SEQ ID NO 461
<211> LENGTH: 12
<212> TYPE: PRT
<213> ORGANISM: artificial sequence
<220> FEATURE:
<223> OTHER INFORMATION: Antimicrobial peptide

<400> SEQUENCE: 461

Phe Ala Leu Leu Lys Ala Leu Leu Lys Lys Ala Leu
1               5                   10

<210> SEQ ID NO 462
<211> LENGTH: 14
<212> TYPE: PRT
<213> ORGANISM: artificial sequence
<220> FEATURE:
<223> OTHER INFORMATION: Antimicrobial peptide

<400> SEQUENCE: 462

Lys Arg Leu Phe Lys Lys Leu Lys Phe Ser Leu Arg Lys Tyr
1               5                   10

<210> SEQ ID NO 463
<211> LENGTH: 14
<212> TYPE: PRT
<213> ORGANISM: artificial sequence
<220> FEATURE:
<223> OTHER INFORMATION: Antimicrobial peptide

<400> SEQUENCE: 463

Lys Arg Leu Phe Lys Lys Leu Leu Phe Ser Leu Arg Lys Tyr
1               5                   10

<210> SEQ ID NO 464
<211> LENGTH: 14
<212> TYPE: PRT
<213> ORGANISM: artificial sequence
<220> FEATURE:
<223> OTHER INFORMATION: Antimicrobial peptide

<400> SEQUENCE: 464

Leu Leu Leu Phe Leu Leu Lys Lys Arg Lys Lys Arg Lys Tyr
1               5                   10

<210> SEQ ID NO 465
<211> LENGTH: 36
<212> TYPE: PRT
<213> ORGANISM: Hyalophora cecropia

<400> SEQUENCE: 465

Lys Trp Lys Leu Phe Lys Lys Ile Glu Lys Val Gly Gln Asn Ile Arg
1               5                   10                  15

-continued

Asp Gly Ile Ile Lys Ala Gly Pro Ala Val Ala Trp Gly Gln Ala Thr
            20                  25                  30

Gln Ile Ala Lys
        35

<210> SEQ ID NO 466
<211> LENGTH: 23
<212> TYPE: PRT
<213> ORGANISM: Xenopus laevis

<400> SEQUENCE: 466

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 467
<211> LENGTH: 22
<212> TYPE: PRT
<213> ORGANISM: Xenopus laevis

<400> SEQUENCE: 467

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 468
<211> LENGTH: 12
<212> TYPE: PRT
<213> ORGANISM: Bos Taurus

<400> SEQUENCE: 468

Arg Leu Cys Arg Ile Val Val Ile Arg Val Cys Arg
1               5                   10

<210> SEQ ID NO 469
<211> LENGTH: 13
<212> TYPE: PRT
<213> ORGANISM: Bos taurus

<400> SEQUENCE: 469

Ile Leu Pro Trp Lys Trp Pro Trp Trp Pro Trp Arg Arg
1               5                   10

<210> SEQ ID NO 470
<211> LENGTH: 24
<212> TYPE: PRT
<213> ORGANISM: Homo sapiens

<400> SEQUENCE: 470

Asp Ser His Ala Lys Arg His His Gly Tyr Lys Arg Lys Phe His Glu
1               5                   10                  15

Lys His His Ser His Arg Gly Tyr
            20

<210> SEQ ID NO 471
<211> LENGTH: 5068
<212> TYPE: DNA
<213> ORGANISM: artificial sequence
<220> FEATURE:
<223> OTHER INFORMATION: Synthetic plasmid

<400> SEQUENCE: 471

-continued

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgcttttta tcgcaactct ctactgtttc tccatacccg ttttttgggc     300
taacaggagg aattacatat ggctagctgc ggtcaacaac gttttcaatg gcaattcgaa     360
caacagccgc gttgcggcca gcaacgcttc caatggcagt ttgaacagca accgcgttgc     420
ggtcagcaac gtttccagtg gcaatttgaa caacagccag agtgcggcca gcagcgcttt     480
cagtggcagt tcgagcagca gccgtgcgga tccgatccat ctgctcaatc tcaactgcct     540
gataaacatt ctggtctgca tgaacgcgct cctcaacgtt acggtccgga ggaggcggcg     600
aagaaagaag aggcggctaa aaagccggct cacattaata agaccaaccc gcatcagggc     660
aaccatcact ccgaaaagac ccagcgtcag ggctccggtg gcggcggtag cggcagcggt     720
ggcggtggtt ctgactccca tcacaaccat cacaagcagg actcccgccc tcagcaccgt     780
aagacgccaa acggcggtgg tgactctcac cataaccacc acaaacagga ctctcgcccg     840
cagcaccgca aaccccctaa cggtaaataa taaggcgcgc cgacccagct ttcttgtaca     900
aagtggttga ttcgaggctg ctaacaaagc ccgaaaggaa gctgagttgg ctgctgccac     960
cgctgagcaa taactagcat aacccctggg ggcctctaaa cgggtcttga ggggttttttt    1020 gctgaaagga ggaactatat ccggatatcc acaggacggg tgtggtcgcc atgatcgcgt    1080
agtcgatagt ggctccaagt agcgaagcga gcaggactgg gcggcggcca aagcggtcgg    1140
acagtgctcc gagaacgggt gcgcatagaa attgcatcaa cgcatatagc gctagcagca    1200
cgccatagtg actggcgatg ctgtcggaat ggacgatatc ccgcaagagg cccggcagta    1260
ccggcataac caagcctatg cctacagcat ccagggtgac ggtgccgagg atgacgatga    1320
gcgcattgtt agatttcata cacggtgcct gactgcgtta gcaatttaac tgtgataaac    1380
taccgcatta aagcttatcg atgataagct gtcaaacatg agaattcgaa gcttggctgt    1440
tttggcggat gagagaagat tttcagcctg atacagatta aatcagaacg cagaagcggt    1500
ctgataaaac agaatttgcc tggcggcagt agcgcggtgg tcccacctga ccccatgccg    1560
aactcagaag tgaaacgccg tagcgccgat ggtagtgtgg ggtctcccca tgcgagagta    1620
gggaactgcc aggcatcaaa taaaacgaaa ggctcagtcg aaagactggg cctttcgttt    1680
tatctgttgt ttgtcggtga acgctctcct gagtaggaca aatccgccgg agcggatttt    1740
gaacgttgcg aagcaacggc ccggagggtg cgggcagga cgcccgccat aaactgccag    1800
gcatcaaatt aagcagaagg ccatcctgac ggatggcctt tttgcgtttc tacaaactct    1860
tttgtttatt tttctaaata cattcaaata tgtatccgct catgagacaa taaccctgat    1920
aaatgcttca ataatattga aaaggaaga gtatgagtat tcaacatttc cgtgtcgccc    1980
ttattccctt ttttgcggca ttttgccttc ctgttttttgc tcacccagaa acgctggtga    2040
aagtaaaaga tgctgaagat cagttgggtg cacgagtggg ttacatcgaa ctggatctca    2100
acagcggtaa gatccttgag agttttcgcc ccgaagaacg ttttccaatg atgagcactt    2160
ttaaagttct gctatgtggc gcggtattat cccgtgttga cgccgggcaa gagcaactcg    2220
gtcgccgcat acactattct cagaatgact tggttgagta ctcaccagtc acagaaaagc    2280
atcttacgga tggcatgaca gtaagagaat tatgcagtgc tgccataacc atgagtgata    2340
acactgcggc caacttactt ctgacaacga tcggaggacc gaaggagcta accgcttttt    2400
```

```
tgcacaacat gggggatcat gtaactcgcc ttgatcgttg ggaaccggag ctgaatgaag    2460
ccataccaaa cgacgagcgt gacaccacga tgcctgtagc aatggcaaca acgttgcgca    2520
aactattaac tggcgaacta cttactctag cttcccggca acaattaata gactggatgg    2580
aggcggataa agttgcagga ccacttctgc gctcggccct tccggctggc tggtttattg    2640
ctgataaatc tggagccggt gagcgtgggt ctcgcggtat cattgcagca ctggggccag    2700
atggtaagcc ctcccgtatc gtagttatct acacgacggg gagtcaggca actatggatg    2760
aacgaaatag acagatcgct gagataggtg cctcactgat taagcattgg taactgtcag    2820
accaagttta ctcatatata ctttagattg atttaaaact tcattttaa tttaaaagga    2880 tctaggtgaa gatccttttt gataatctca tgaccaaaat cccttaacgt gagttttcgt    2940
tccactgagc gtcagacccc gtagaaaaga tcaaaggatc ttcttgagat ccttttttc    3000 tgcgcgtaat ctgctgcttg caaacaaaaa aaccaccgct accagcggtg gtttgtttgc    3060
cggatcaaga gctaccaact ctttttccga aggtaactgg cttcagcaga gcgcagatac    3120
caaatactgt ccttctagtg tagccgtagt taggccacca cttcaagaac tctgtagcac    3180
cgcctacata cctcgctctg ctaatcctgt taccagtggc tgctgccagt ggcgataagt    3240
cgtgtcttac cgggttggac tcaagacgat agttaccgga taaggcgcag cggtcgggct    3300 gaacggggg ttcgtgcaca cagcccagct tggagcgaac gacctacacc gaactgagat    3360
acctacagcg tgagctatga gaaagcgcca cgcttcccga agggagaaag gcggacaggt    3420
atccggtaag cggcagggtc ggaacaggag agcgcacgag ggagcttcca gggggaaacg    3480
cctggtatct ttatagtcct gtcgggtttc gccacctctg acttgagcgt cgatttttgt    3540
gatgctcgtc agggggcgg agcctatgga aaaacgccag caacgcggcc tttttacggt    3600
tcctggcctt ttgctggcct tttgctcaca tgttctttcc tgcgttatcc cctgattctg    3660
tggataaccg tattaccgcc tttgagtgag ctgataccgc tcgccgcagc cgaacgaccg    3720
agcgcagcga gtcagtgagc gaggaagcgg aagagcgcct gatgcggtat tttctcctta    3780
cgcatctgtg cggtatttca caccgcatat atggtgcact ctcagtacaa tctgctctga    3840
tgccgcatag ttaagccagt atacactccg ctatcgctac gtgactgggt catggctgcg    3900
ccccgacacc cgccaacacc cgctgacgcg ccctgacggg cttgtctgct cccggcatcc    3960
gcttacagac aagctgtgac cgtctccggg agctgcatgt gtcagaggtt ttcaccgtca    4020
tcaccgaaac gcgcgaggca gcagatcaat tcgcgcgcga aggcgaagcg gcatgcataa    4080
tgtgcctgtc aaatggacga agcagggatt ctgcaaaccc tatgctactc cgtcaagccg    4140
tcaattgtct gattcgttac caattatgac aacttgacgg ctacatcatt cacttttct    4200 tcacaaccgg cacggaactc gctcgggctg ccccggtgc atttttaaa tacccgcgag    4260 aaatagagtt gatcgtcaaa accaacattg cgaccgacgg tggcgatagg catccgggtg    4320
gtgctcaaaa gcagcttcgc ctggctgata cgttggtcct cgcgccagct taagacgcta    4380
atccctaact gctggcggaa agatgtgaca gacgcgacg gcgacaagca acatgctgt    4440 gcgacgctgg cgatatcaaa attgctgtct gccaggtgat cgctgatgta ctgacaagcc    4500
tcgcgtaccc gattatccat cggtggatgg agcgactcgt taatcgcttc catgcgccgc    4560
agtaacaatt gctcaagcag atttatcgcc agcagctccg aatagcgccc ttccccttgc    4620
ccggcgttaa tgatttgccc aaacaggtcg ctgaaatgcg gctggtgcgc ttcatccggg    4680
cgaaagaacc ccgtattggc aaatattgac ggccagttaa gccattcatg ccagtaggcg    4740
cgcggacgaa agtaaaccca ctggtgatac cattcgcgag cctccggatg acgaccgtag    4800
```

```
tgatgaatct ctcctggcgg aacagcaaa atatcaccg gtcggcaaac aaattctcgt    4860
ccctgatttt tcaccacccc ctgaccgcga atggtgagat tgagaatata acctttcatt    4920
cccagcggtc ggtcgataaa aaaatcgaga taaccgttgg cctcaatcgg cgttaaaccc    4980
gccaccagat gggcattaaa cgagtatccc ggcagcaggg gatcattttg cgcttcagcc    5040
atacttttca tactcccgcc attcagag                                        5068
```

```
<210> SEQ ID NO 472
<211> LENGTH: 546
<212> TYPE: DNA
<213> ORGANISM: artificial sequence
<220> FEATURE:
<223> OTHER INFORMATION: synethic construct

<400> SEQUENCE: 472
gctagctgcg gtcaacaacg ttttcaatgg caattcgaac aacagccgcg ttgcggccag     60
caacgcttcc aatggcagtt tgaacagcaa ccgcgttgcg gtcagcaacg tttccagtgg    120
caatttgaac aacagccaga gtgcggccag cagcgctttc agtggcagtt cgagcagcag    180
ccgtgcgatc catctgctca atctcaactg cctgataaac attctggtct gcatgaacgc    240
gctcctcaac gttacggtcc ggaggaggcg gcgaagaaag aagaggcggc taaaaagccg    300
gctcacatta ataagaccaa cccgcatcag ggcaaccatc actccgaaaa gacccagcgt    360
cagggctccg gtggcggcgg tagcggcagc ggtggcggtg gttctgactc ccatcacaac    420
catcacaagc aggactcccg ccctcagcac cgtaagacgc caaacggcgg tggtgactct    480
caccataacc accacaaaca ggactctcgc ccgcagcacc gcaaaacccc taacggtaaa    540
taataa                                                                546
```

```
<210> SEQ ID NO 473
<211> LENGTH: 180
<212> TYPE: PRT
<213> ORGANISM: artificial sequence
<220> FEATURE:
<223> OTHER INFORMATION: synethic construct

<400> SEQUENCE: 473

Ala Ser Cys Gly Gln Gln Arg Phe Gln Trp Gln Phe Glu Gln Gln Pro
1               5                   10                  15

Arg Cys Gly Gln Gln Arg Phe Gln Trp Gln Phe Glu Gln Gln Pro Arg
                20                  25                  30

Cys Gly Gln Gln Arg Phe Gln Trp Gln Phe Glu Gln Gln Pro Glu Cys
            35                  40                  45

Gly Gln Gln Arg Phe Gln Trp Gln Phe Glu Gln Gln Pro Cys Asp Pro
        50                  55                  60

Ser Ala Gln Ser Gln Leu Pro Asp Lys His Ser Gly Leu His Glu Arg
65                  70                  75                  80

Ala Pro Gln Arg Tyr Gly Pro Glu Glu Ala Ala Lys Lys Glu Glu Ala
                85                  90                  95

Ala Lys Lys Pro Ala His Ile Asn Lys Thr Asn Pro His Gln Gly Asn
            100                 105                 110

His His Ser Glu Lys Thr Gln Arg Gln Gly Ser Gly Gly Gly Gly Ser
        115                 120                 125

Gly Ser Gly Gly Gly Gly Ser Asp Ser His His Asn His His Lys Gln
    130                 135                 140

Asp Ser Arg Pro Gln His Arg Lys Thr Pro Asn Gly Gly Gly Asp Ser
145                 150                 155                 160
```

His His Asn His His Lys Gln Asp Ser Arg Pro Gln His Arg Lys Thr
                165                 170                 175
Pro Asn Gly Lys
            180

<210> SEQ ID NO 474
<211> LENGTH: 3772
<212> TYPE: DNA
<213> ORGANISM: artificial sequence
<220> FEATURE:
<223> OTHER INFORMATION: synthetic plasmid

<400> SEQUENCE: 474

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgacagct | gtctcttata | cacatctcaa | ccatcatcga | tgaattttct | cgggtgttct | 360 |
| cgcatattgg | ctcgaattct | acctgcagat | gagttaattt | ctcctcttta | atgaattctg | 420 |
| tgtgaaattg | ttatccgctc | acaattgaat | ctattataat | tgttatccgc | tcacaaagca | 480 |
| aataaatttt | ttatgatttc | tcgaggtgaa | gacgaaaggg | cctcgtgata | cgcctatttt | 540 |
| tatagggccg | gccataactt | cgtatagcat | acattatacg | aagttattta | attaacacac | 600 |
| aacaggccaa | gactacaaag | gcgcgcttag | aaaaactcat | cgagcatcaa | atgaaactgc | 660 |
| aatttattca | tatcaggatt | atcaatacca | tattttttgaa | aaagccgttt | ctgtaatgaa | 720 |
| ggagaaaact | caccgaggca | gttccatagg | atggcaagat | cctggtatcg | gtctgcgatt | 780 |
| ccgactcgtc | caacatcaat | acaacctatt | aatttcccct | cgtcaaaaat | aaggttatca | 840 |
| agtgagaaat | caccatgagt | gacgactgaa | tccggtgaga | atggcaaaag | tttatgcatt | 900 |
| tctttccaga | cttgttcaac | aggccagcca | ttacgctcgt | catcaaaatc | actcgcatca | 960 |
| accaaaccgt | tattcattcg | tgattgcgcc | tgagcgagac | gaaatacgcg | atcgctgtta | 1020 |
| aaaggacaat | tacaaacagg | aatcgaatgc | aaccggcgca | ggaacactgc | cagcgcatca | 1080 |
| acaatatttt | cacctgaatc | aggatattct | tctaatacct | ggaatgctgt | tttcccgggg | 1140 |
| atcgcagtgg | tgagtaacca | tgcatcatca | ggagtacgga | taaaatgctt | gatggtcgga | 1200 |
| agaggcataa | attccgtcag | ccagtttagt | ctgaccatct | catctgtaac | atcattggca | 1260 |
| acgctacctt | tgccatgttt | cagaaacaac | tctggcgcat | cgggcttccc | atacaatcga | 1320 |
| tagattgtcg | cacctgattg | cccgacatta | tcgcgagccc | atttataccc | atataaatca | 1380 |
| gcatccatgt | tggaatttaa | tcgcggccta | gagcaagacg | tttcccgttg | aatatggctc | 1440 |
| ataacacccc | ttgtattact | gtttatgtaa | gcagacagtt | ttattgttca | tgaccaaaat | 1500 |
| cccttaacgt | gagttttcgt | tccactgagc | gtcagacccc | gtagaaaaga | tcaaaggatc | 1560 |
| ttcttgagat | cctttttttc | tgcgcgtaat | ctgctgcttt | gcggccgca | taacttcgta | 1620 |
| tagcatacat | tatacgaagt | tatgcgatcg | caagcttgcc | aacgactacg | cactagccaa | 1680 |
| caagagcttc | agggttgaga | tgtgtataag | agacagctgt | cttaatgaat | cggccaacgc | 1740 |
| gcggggagag | gcggtttgcg | tattgggcgc | tcttccgctt | cctcgctcac | tgactcgctg | 1800 |
| cgctcggtcg | ttcggctgcg | gcgagcggta | tcagctcact | caaaggcggt | aatacggtta | 1860 |
| tccacagaat | caggggataa | cgcaggaaag | aacatgtgag | caaaaggcca | gcaaaaggcc | 1920 |

```
aggaaccgta aaaaggccgc gttgctggcg ttttttccata ggctccgccc ccctgacgag    1980
catcacaaaa atcgacgctc aagtcagagg tggcgaaacc cgacaggact ataaagatac    2040
caggcgtttc ccctggaag  ctccctcgtg cgctctcctg ttccgaccct gccgcttacc    2100
ggatacctgt ccgcctttct cccttcggga agcgtggcgc tttctcatag ctcacgctgt    2160
aggtatctca gttcggtgta ggtcgttcgc tccaagctgg gctgtgtgca cgaaccccc     2220 gttcagcccg accgctgcgc cttatccggt aactatcgtc ttgagtccaa cccggtaaga    2280
cacgacttat cgccactggc agcagccact ggtaacagga ttagcagagc gaggtatgta    2340
ggcggtgcta cagagttctt gaagtggtgg cctaactacg gctacactag aaggacagta    2400
tttggtatct gcgctctgct gaagccagtt accttcggaa aaagagttgg tagctcttga    2460
tccggcaaac aaaccaccgc tggtagcggt ggttttttg  tttgcaagca gcagattacg    2520
cgcagaaaaa aaggatctca agaagatcct ttgatctttt ctacggggtc tgacgctcag    2580
tggaacgaaa actcacgtta agggatttg  gtcatgagat tatcaaaaag gatcttcacc    2640
tagatccttt taaattaaaa atgaagtttt aaatcaatct aaagtatata tgagtaaact    2700
tggtctgaca gttaccaatg cttaatcagt gaggcaccta tctcagcgat ctgtctattt    2760
cgttcatcca tagttgcctg actccccgtc gtgtagataa ctacgatacg ggagggctta    2820
ccatctggcc ccagtgctgc aatgatacc  cgagacccac gctcaccggc tccagattta    2880
tcagcaataa accagccagc cggaagggcc gagcgcagaa gtggtcctgc aactttatcc    2940
gcctccatcc agtctattaa ttgttgccgg gaagctagag taagtagttc gccagttaat    3000
agtttgcgca acgttgttgc cattgctaca ggcatcgtgg tgtcacgctc gtcgtttggt    3060
atggcttcat tcagctccgg ttcccaacga tcaaggcgag ttacatgatc ccccatgttg    3120
tgcaaaaaag cggttagctc cttcggtcct ccgatcgttg tcagaagtaa gttggccgca    3180
gtgttatcac tcatggttat ggcagcactg cataattctc ttactgtcat gccatccgta    3240
agatgctttt ctgtgactgg tgagtactca accaagtcat tctgagaata gtgtatgcgg    3300
cgaccgagtt gctcttgccc ggcgtcaata cgggataata ccgcgccaca tagcagaact    3360
ttaaaagtgc tcatcattgg aaaacgttct tcggggcgaa aactctcaag gatcttaccg    3420
ctgttgagat ccagttcgat gtaacccact cgtgcaccca actgatcttc agcatctttt    3480
actttcacca gcgtttctgg gtgagcaaaa acaggaaggc aaaatgccgc aaaaaaggga    3540
ataagggcga cacggaaatg ttgaatactc atactcttcc tttttcaata ttattgaagc    3600
atttatcagg gttattgtct catgagcgga tacatatttg aatgtattta gaaaaataaa    3660 caaataggg  ttccgcgcac atttccccga aaagtgccac ctgacgtcta agaaaccatt    3720
attatcatga cattaaccta taaaaatagg cgtatcacga ggccctttcg tc            3772
```

<210> SEQ ID NO 475
<211> LENGTH: 3868
<212> TYPE: DNA
<213> ORGANISM: artificial sequence
<220> FEATURE:
<223> OTHER INFORMATION: synthetic plasmid

<400> SEQUENCE: 475

```
tcgcgcgttt cggtgatgac ggtgaaaacc tctgacacat gcagctcccg gagacggtca     60
cagcttgtct gtaagcggat gccgggagca gacaagcccg tcaggcgcg  tcagcgggtg    120 ttggcgggtg tcgggctgg  cttaactatg cggcatcaga gcagattgta ctgagagtgc    180
accatatgcg gtgtgaaata ccgcacagat gcgtaaggag aaaataccgc atcaggcgcc    240
```

```
attcgccatt caggctgcgc aactgttggg aagggcgatc ggtgcgggcc tcttcgctat    300
tacgacagct gtctcttata cacatctcaa ccatcatcga tgaattttct cgggtgttct    360
cgcatattgg ctcgaattct acctgcagtt tagcttcctt agctcctgaa aatctcgata    420
actcaaaaaa tacgcccggt agtgatctta tttcattatg gtgaaagttg gaacctctta    480
cgtgccgatc aacgtctcat tttcgccaaa agttggccca gggcttcccg gtatcaacag    540
ggacaccagg atttatttat tctgcgaagt gatcttccgt cacaggtatt tattcggcgc    600
aaagggcctc gtgatacgcc tatttttata ggttaatgtc aggccggcca taacttcgta    660
tagcatacat tatacgaagt tatttaatta acacacaaca ggccaagact acaaaggcgc    720
gcttagaaaa actcatcgag catcaaatga aactgcaatt tattcatatc aggattatca    780
ataccatatt tttgaaaaag ccgtttctgt aatgaaggag aaaactcacc gaggcagttc    840
cataggatgg caagatcctg gtatcggtct gcgattccga ctcgtccaac atcaatacaa    900
cctattaatt tcccctcgtc aaaaataagg ttatcaagtg agaaatcacc atgagtgacg    960
actgaatccg gtgagaatgg caaaagttta tgcatttctt ccagacttg ttcaacaggc    1020 cagccattac gctcgtcatc aaaatcactc gcatcaacca aaccgttatt cattcgtgat    1080
tgcgcctgag cgagacgaaa tacgcgatcg ctgttaaaag gacaattaca acaggaatc    1140 gaatgcaacc ggcgcaggaa cactgccagc gcatcaacaa tattttcacc tgaatcagga    1200
tattcttcta atacctggaa tgctgttttc ccggggatcg cagtggtgag taaccatgca    1260
tcatcaggag tacggataaa atgcttgatg gtcggaagag gcataaattc cgtcagccag    1320
tttagtctga ccatctcatc tgtaacatca ttggcaacgc tacctttgcc atgtttcaga    1380
aacaactctg gcgcatcggg cttcccatac aatcgataga ttgtcgcacc tgattgcccg    1440
acattatcgc gagcccattt atacccatat aaatcagcat ccatgttgga atttaatcgc    1500
ggcctagagc aagacgtttc ccgttgaata tggctcataa cacccccttgt attactgttt    1560 atgtaagcag acagttttat tgttcatgac caaaatccct taacgtgagt tttcgttcca    1620
ctgagcgtca gacccgtag aaaagatcaa aggatcttct tgagatcctt ttttttctgcg    1680 cgtaatctgc tgcttctagcg gccgcataac ttcgtatagc atacattata cgaagttatg    1740
cgatcgcaag cttgccaacg actacgcact agccaacaag agcttcaggg ttgagatgtg    1800
tataagagac agctgtctta atgaatcggc caacgcgcgg ggagaggcgg tttgcgtatt    1860
gggcgctctt ccgcttcctc gctcactgac tcgctgcgct cggtcgttcg gctgcggcga    1920
gcggtatcag ctcactcaaa ggcggtaata cggttatcca cagaatcagg ggataacgca    1980
ggaaagaaca tgtgagcaaa aggccagcaa aaggccagga accgtaaaaa ggccgcgttg    2040
ctggcgtttt tccataggct ccgcccccct gacgagcatc acaaaaatcg acgctcaagt    2100
cagaggtggc gaaacccgac aggactataa agataccagg cgtttccccc tggaagctcc    2160
ctcgtgcgct ctcctgttcc gaccctgccg cttaccggat acctgtccgc ctttctccct    2220
tcgggaagcg tggcgctttc tcatagctca cgctgtaggt atctcagttc ggtgtaggtc    2280
gttcgctcca agctgggctg tgtgcacgaa ccccccgttc agcccgaccg ctgcgcctta    2340
tccggtaact atcgtcttga gtccaacccg gtaagacacg acttatcgcc actggcagca    2400
gccactggta acaggattag cagagcgagg tatgtaggcg gtgctacaga gttcttgaag    2460
tggtggccta actacggcta cactagaagg acagtatttg gtatctgcgc tctgctgaag    2520
ccagttacct tcggaaaaag agttggtagc tcttgatccg gcaaacaaac caccgctggt    2580
agcggtggtt tttttgtttg caagcagcag attacgcgca gaaaaaaagg atctcaagaa    2640
```

```
gatcctttga tctttctac ggggtctgac gctcagtgga acgaaaactc acgttaaggg      2700
attttggtca tgagattatc aaaaaggatc ttcacctaga tccttttaaa ttaaaaatga      2760
agttttaaat caatctaaag tatatatgag taaacttggt ctgacagtta ccaatgctta      2820
atcagtgagg cacctatctc agcgatctgt ctatttcgtt catccatagt tgcctgactc      2880
cccgtcgtgt agataactac gatacgggag ggcttaccat ctggccccag tgctgcaatg      2940
ataccgcgag acccacgctc accggctcca gatttatcag caataaacca gccagccgga      3000
agggccgagc gcagaagtgg tcctgcaact ttatccgcct ccatccagtc tattaattgt      3060
tgccgggaag ctagagtaag tagttcgcca gttaatagtt tgcgcaacgt tgttgccatt      3120
gctacaggca tcgtggtgtc acgctcgtcg tttggtatgg cttcattcag ctccggttcc      3180
caacgatcaa ggcgagttac atgatccccc atgttgtgca aaaaagcggt tagctccttc      3240
ggtcctccga tcgttgtcag aagtaagttg gccgcagtgt tatcactcat ggttatggca      3300
gcactgcata attctcttac tgtcatgcca tccgtaagat gcttttctgt gactggtgag      3360
tactcaacca agtcattctg agaatagtgt atgcggcgac cgagttgctc ttgcccggcg      3420
tcaatacggg ataataccgc gccacatagc agaactttaa aagtgctcat cattggaaaa      3480
cgttcttcgg ggcgaaaact ctcaaggatc ttaccgctgt tgagatccag ttcgatgtaa      3540
cccactcgtg cacccaactg atcttcagca tcttttactt tcaccagcgt ttctgggtga      3600
gcaaaaacag gaaggcaaaa tgccgcaaaa aagggaataa gggcgacacg gaaatgttga      3660
atactcatac tcttcctttt tcaatattat tgaagcattt atcagggtta ttgtctcatg      3720
agcggataca tatttgaatg tatttagaaa aataaacaaa tagggggttcc gcgcacattt      3780 ccccgaaaag tgccacctga cgtctaagaa accattatta tcatgacatt aacctataaa      3840
aataggcgta tcacgaggcc ctttcgtc                                        3868

<210> SEQ ID NO 476
<211> LENGTH: 3847
<212> TYPE: DNA
<213> ORGANISM: artificial sequence
<220> FEATURE:
<223> OTHER INFORMATION: synethic plasmid

<400> SEQUENCE: 476
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgacagct gtctcttata cacatctcaa ccatcatcga tgaattttct cgggtgttct       360
cgcatattgg ctcgaattct acctgcaggg tttattcctc cttatttaat cgatacatta       420
atatatacct cttaatttt taataataaa gttaatcgat aattccgtc gagtgcccac       480 acagattgtc tgataaattg ttaaagagca gtgccgcttc gctttttctc agcggcgctg       540
tttcctgtgt gaaattgtta tccgctcaca attccacaca ttatacgagc cggatgatta       600
attgtcaaca gctcatttca ggccggccat aacttcgtat agcatacatt atacgaagtt       660
atttaattaa cacacaacag gccaagacta caaaggcgcg cttagaaaaa ctcatcgagc       720
atcaaatgaa actgcaattt attcatatca ggattatcaa taccatattt tgaaaaagc       780 cgtttctgta atgaaggaga aaactcaccg aggcagttcc ataggatggc aagatcctgg       840
```

```
tatcggtctg cgattccgac tcgtccaaca tcaatacaac ctattaattt cccctcgtca    900
aaaataaggt tatcaagtga gaaatcacca tgagtgacga ctgaatccgg tgagaatggc    960
aaaagtttat gcatttcttt ccagacttgt tcaacaggcc agccattacg ctcgtcatca   1020
aaatcactcg catcaaccaa accgttattc attcgtgatt gcgcctgagc gagacgaaat   1080
acgcgatcgc tgttaaaagg acaattacaa acaggaatcg aatgcaaccg cgcaggaac    1140
actgccagcg catcaacaat attttcacct gaatcaggat attcttctaa tacctggaat   1200
gctgttttcc cggggatcgc agtggtgagt aaccatgcat catcaggagt acggataaaa   1260
tgcttgatgg tcggaagagg cataaattcc gtcagccagt ttagtctgac catctcatct   1320
gtaacatcat tggcaacgct acctttgcca tgtttcagaa acaactctgg cgcatcgggc   1380
ttcccataca atcgatagat tgtcgcacct gattgcccga cattatcgcg agcccattta   1440
tacccatata aatcagcatc catgttggaa tttaatcgcg gcctagagca agacgtttcc   1500
cgttgaatat ggctcataac accccttgta ttactgttta tgtaagcaga cagtttatt    1560
gttcatgacc aaaatccctt aacgtgagtt ttcgttccac tgagcgtcag accccgtaga   1620
aaagatcaaa ggatcttctt gagatccttt ttttctgcgc gtaatctgct gcttctagcgg  1680
ccgcataact tcgtatagca tacattatac gaagttatgc gatcgcaagc ttgccaacga   1740
ctacgcacta gccaacaaga gcttcagggt tgagatgtgt ataagagaca gctgtcttaa   1800
tgaatcggcc aacgcgcggg gagaggcggt ttgcgtattg ggcgctcttc cgcttcctcg   1860
ctcactgact cgctgcgctc ggtcgttcgg ctgcggcgag cggtatcagc tcactcaaag   1920
gcggtaatac ggttatccac agaatcaggg gataacgcag gaaagaacat gtgagcaaaa   1980
ggccagcaaa aggccaggaa ccgtaaaaag gccgcgttgc tggcgttttt ccataggctc   2040
cgccccctg acgagcatca caaaaatcga cgctcaagtc agaggtggcg aaacccgaca    2100
ggactataaa gataccaggc gtttccccct ggaagctccc tcgtgcgctc tcctgttccg   2160
accctgccgc ttaccggata cctgtccgcc tttctccctt cgggaagcgt ggcgctttct   2220
catagctcac gctgtaggta tctcagttcg gtgtaggtcg ttcgctccaa gctgggctgt   2280
gtgcacgaac cccccgttca gcccgaccgc tgcgccttat ccggtaacta tcgtcttgag   2340
tccaacccgg taagacacga cttatcgcca ctggcagcag ccactggtaa caggattagc   2400
agagcgaggt atgtaggcgg tgctacagag ttcttgaagt ggtggcctaa ctacggctac   2460
actagaagga cagtatttgg tatctgcgct ctgctgaagc cagttacctt cggaaaaaga   2520
gttggtagct cttgatccgg caaacaaacc accgctggta gcggtggttt ttttgtttgc   2580
aagcagcaga ttacgcgcag aaaaaaagga tctcaagaag atcctttgat cttttctacg   2640
gggtctgacg ctcagtggaa cgaaaactca cgttaaggga ttttggtcat gagattatca   2700
aaaaggatct tcacctagat ccttttaaat taaaaatgaa gttttaaatc aatctaaagt   2760
atatatgagt aaacttggtc tgacagttac caatgcttaa tcagtgaggc acctatctca   2820
gcgatctgtc tatttcgttc atccatagtt gcctgactcc ccgtcgtgta gataactacg   2880
atacgggagg gcttaccatc tggccccagt gctgcaatga taccgcgaga cccacgctca   2940
ccggctccag atttatcagc aataaaccag ccagccggaa gggccgagcg cagaagtggt   3000
cctgcaactt tatccgcctc catccagtct attaattgtt gccgggaagc tagagtaagt   3060
agttcgccag ttaatagttt gcgcaacgtt gttgccattg ctacaggcat cgtggtgtca   3120
cgctcgtcgt ttggtatggc ttcattcagc tccggttccc aacgatcaag gcgagttaca   3180
tgatccccca tgttgtgcaa aaaagcggtt agctccttcg gtcctccgat cgttgtcaga   3240
```

```
agtaagttgg ccgcagtgtt atcactcatg gttatggcag cactgcataa ttctcttact    3300
gtcatgccat ccgtaagatg cttttctgtg actggtgagt actcaaccaa gtcattctga    3360
gaatagtgta tgcggcgacc gagttgctct tgcccggcgt caatacggga taataccgcg    3420
ccacatagca gaactttaaa agtgctcatc attggaaaac gttcttcggg gcgaaaactc    3480
tcaaggatct taccgctgtt gagatccagt tcgatgtaac ccactcgtgc acccaactga    3540
tcttcagcat cttttacttt caccagcgtt tctgggtgag caaaaacagg aaggcaaaat    3600
gccgcaaaaa agggaataag ggcgacacgg aaatgttgaa tactcatact cttcctttt    3660
caatattatt gaagcattta tcagggttat tgtctcatga gcggatacat atttgaatgt    3720
atttagaaaa ataaacaaat aggggttccg cgcacatttc cccgaaaagt gccacctgac    3780
gtctaagaaa ccattattat catgacatta acctataaaa ataggcgtat cacgaggccc    3840
tttcgtc                                                              3847

<210> SEQ ID NO 477
<211> LENGTH: 1408
<212> TYPE: DNA
<213> ORGANISM: artificial sequence
<220> FEATURE:
<223> OTHER INFORMATION: synethic construct

<400> SEQUENCE: 477
ctgtctctta tacacatctc aaccctgaag ctcttgttgg ctagtgcgta gtcgttggca      60
agcttgcgat cgcataactt cgtataatgt atgctatacg aagttatgcg gccgctagag     120
cagcagatta cgcgcagaaa aaaggatctc aagaagatcc tttgatcttt tctacgggg     180
tctgacgctc agtggaacga aaactcacgt taagggattt tggtcatgaa caataaaact     240
gtctgcttac ataaacagta atacaagggg tgttatgagc catattcaac gggaaacgtc     300
ttgctctagg ccgcgattaa attccaacat ggatgctgat ttatatgggt ataaatgggc     360
tcgcgataat gtcgggcaat caggtgcgac aatctatcga ttgtatggga agcccgatgc     420
gccagagttg tttctgaaac atggcaaagg tagcgttgcc aatgatgtta cagatgagat     480
ggtcagacta aactggctga cggaatttat gcctcttccg accatcaagc attttatccg     540
tactcctgat gatgcatggt tactcaccac tgcgatcccc gggaaaacag cattccaggt     600
attagaagaa tatcctgatt caggtgaaaa tattgttgat gcgctggcag tgttcctgcg     660
ccggttgcat tcgattcctg tttgtaattg tccttttaac agcgatcgcg tatttcgtct     720
cgctcaggcg caatcacgaa tgaataacgg tttggttgat gcgagtgatt ttgatgacga     780
gcgtaatggc tggcctgttg aacaagtctg gaaagaaatg cataaacttt tgccattctc     840
accggattca gtcgtcactc atggtgattt ctcacttgat aaccttattt ttgacgaggg     900
gaaattaata ggttgtattg atgttggacg agtcggaatc gcagaccgat accaggatct     960
tgccatccta tggaactgcc tcggtgagtt ttctccttca ttacagaaac ggcttttca    1020
aaaatatggt attgataatc ctgatatgaa taaattgcag tttcatttga tgctcgatga    1080
gttttttcta agcgcgcctt tgtagtcttg gcctgttgtgt gttaattaaa taacttcgta    1140
taatgtatgc tatacgaagt tatggccggc cctataaaaa taggcgtatc acgaggccct    1200
ttcgtcttca cctcgagaaa tcataaaaaa tttatttgct ttgtgagcgg ataacaatta    1260
taatagattc aattgtgagc ggataacaat ttcacacaga attcattaaa gaggagaaat    1320
taactcatct gcaggtagaa ttcgagccaa tatgcgagaa caccccgagaa aattcatcga    1380
tgatggttga gatgtgtata agagacag                                       1408
```

<210> SEQ ID NO 478
<211> LENGTH: 1504
<212> TYPE: DNA
<213> ORGANISM: artificial sequence
<220> FEATURE:
<223> OTHER INFORMATION: synethic construct

<400> SEQUENCE: 478

```
ctgtctctta tacacatctc aaccctgaag ctcttgttgg ctagtgcgta gtcgttggca    60
agcttgcgat cgcataactt cgtataatgt atgctatacg aagttatgcg gccgctagag   120
cagcagatta cgcgcagaaa aaaggatctc aagaagatcc tttgatcttt tctacgggg    180
tctgacgctc agtggaacga aaactcacgt taagggattt tggtcatgaa caataaaact   240
gtctgcttac ataaacagta atacaagggg tgttatgagc catattcaac gggaaacgtc   300
ttgctctagg ccgcgattaa attccaacat ggatgctgat ttatatgggt ataaatgggc   360
tcgcgataat gtcgggcaat caggtgcgac aatctatcga ttgtatggga agcccgatgc   420
gccagagttg tttctgaaac atggcaaagg tagcgttgcc aatgatgtta cagatgagat   480
ggtcagacta aactggctga cggaatttat gcctcttccg accatcaagc attttatccg   540
tactcctgat gatgcatggt tactcaccac tgcgatcccc gggaaaacag cattccaggt   600
attagaagaa tatcctgatt caggtgaaaa tattgttgat gcgctggcag tgttcctgcg   660
ccggttgcat tcgattcctg tttgtaattg tccttttaac agcgatcgcg tatttcgtct   720
cgctcaggcg caatcacgaa tgaataacgg tttggttgat gcgagtgatt ttgatgacga   780
gcgtaatggc tggcctgttg aacaagtctg gaaagaaatg cataaacttt tgccattctc   840
accggattca gtcgtcactc atggtgattt ctcacttgat aaccttattt ttgacgaggg   900
gaaattaata ggttgtattg atgttggacg agtcggaatc gcagaccgat accaggatct   960
tgccatccta tggaactgcc tcggtgagtt ttctccttca ttacagaaac ggctttttca  1020
aaaatatggt attgataatc ctgatatgaa taaattgcag tttcatttga tgctcgatga  1080
gttttttcta agcgcgccttt gtagtcttgg cctgttgtgt gttaattaaa taacttcgta  1140
taatgtatgc tatacgaagt tatggccggc ctgacattaa cctataaaaa taggcgtatc  1200
acgaggccct ttcgccgaa taaatacctg tgacggaaga tcacttcgca gaataaataa  1260
atcctggtgt ccctgttgat accgggaagc cctgggccaa cttttggcga aaatgagacg  1320
ttgatcggca cgtaagaggt tccaactttc accataatga aataagatca ctaccgggcg  1380
tattttttga gttatcgaga ttttcaggag ctaaggaagc taaactgcag gtagaattcg  1440
agccaatatg cgagaacacc cgagaaaatt catcgatgat ggttgagatg tgtataagag  1500
acag                                                              1504
```

<210> SEQ ID NO 479
<211> LENGTH: 1483
<212> TYPE: DNA
<213> ORGANISM: artificial sequence
<220> FEATURE:
<223> OTHER INFORMATION: synethic construct

<400> SEQUENCE: 479

```
ctgtctctta tacacatctc aaccctgaag ctcttgttgg ctagtgcgta gtcgttggca    60
agcttgcgat cgcataactt cgtataatgt atgctatacg aagttatgcg gccgctagag   120
cagcagatta cgcgcagaaa aaaggatctc aagaagatcc tttgatcttt tctacgggg    180
tctgacgctc agtggaacga aaactcacgt taagggattt tggtcatgaa caataaaact   240
```

```
gtctgcttac ataaacagta atacaagggg tgttatgagc catattcaac gggaaacgtc      300
ttgctctagg ccgcgattaa attccaacat ggatgctgat ttatatgggt ataaatgggc      360
tcgcgataat gtcgggcaat caggtgcgac aatctatcga ttgtatggga agcccgatgc      420
gccagagttg tttctgaaac atggcaaagg tagcgttgcc aatgatgtta cagatgagat      480
ggtcagacta aactggctga cggaatttat gcctcttccg accatcaagc attttatccg      540
tactcctgat gatgcatggt tactcaccac tgcgatcccc gggaaaacag cattccaggt      600
attagaagaa tatcctgatt caggtgaaaa tattgttgat gcgctggcag tgttcctgcg      660
ccggttgcat tcgattcctg tttgtaattg tccttttaac agcgatcgcg tatttcgtct      720
cgctcaggcg caatcacgaa tgaataacg tttggttgat gcgagtgatt ttgatgacga      780
gcgtaatggc tggcctgttg aacaagtctg gaaagaaatg cataaacttt tgccattctc      840
accggattca gtcgtcactc atggtgattt ctcacttgat aaccttattt ttgacgaggg      900
gaaattaata ggttgtattg atgttggacg agtcggaatc gcagaccgat accaggatct      960
tgccatccta tggaactgcc tcggtgagtt ttctccttca ttacagaaac ggcttttca     1020 aaaatatggt attgataatc ctgatatgaa taaattgcag tttcatttga tgctcgatga     1080 gttttctaa gcgcgccttt gtagtcttgg cctgttgtgt gttaattaaa taacttcgta     1140
taatgtatgc tatacgaagt tatggccggc ctgaaatgag ctgttgacaa ttaatcatcc     1200
ggctcgtata atgtgtggaa ttgtgagcgg ataacaattt cacacaggaa acagcgccgc     1260
tgagaaaaag cgaagcggca ctgctcttta acaatttatc agacaatctg tgtgggcact     1320
cgaccggaat tatcgattaa cttttattatt aaaaattaaa gaggtatata ttaatgtatc     1380
gattaaataa ggaggaataa accctgcagg tagaattcga gccaatatgc gagaacaccc     1440
gagaaaattc atcgatgatg gttgagatgt gtataagaga cag                       1483
```

<210> SEQ ID NO 480
<211> LENGTH: 22
<212> TYPE: DNA
<213> ORGANISM: artificial sequence
<220> FEATURE:
<223> OTHER INFORMATION: primer

<400> SEQUENCE: 480

```
ctgtctctta tacacatctc aa                                                22
```

<210> SEQ ID NO 481
<211> LENGTH: 20
<212> TYPE: DNA
<213> ORGANISM: artificial seqeunce
<220> FEATURE:
<223> OTHER INFORMATION: primer

<400> SEQUENCE: 481

```
gcttgccaac gactacgcac                                                   20
```

<210> SEQ ID NO 482
<211> LENGTH: 1761
<212> TYPE: DNA
<213> ORGANISM: Escherichia coli

<400> SEQUENCE: 482

```
atggtaactc atcgtcagcg ctaccgtgaa aaagtctccc agatggtcag ttgggggcac       60
tggtttgcac tgttcaatat tctgctttcg ctcgtcattg cagccgtta cctgtttatc      120 gccgactggc cgacaacgct tgctggtcgc atttattcct acgtaagcat tatcggccat      180
```

```
ttcagcttcc tggtgttcgc cacctacttg ctgatcctct tcccgctgac ctttatcgtc    240
ggctcccaga ggctgatgag gtttttgtcc gtcattctgg caacggcggg aatgacgcta    300
ttactgatcg atagcgaagt ctttactcgt ttccatctcc atcttaatcc catcgtctgg    360
caactggtta tcaacccaga cgaaaatgag atggcgcgcg actggcagct gatgttcatc    420
agcgtgccgg ttattttatt gcttgaactg gtgtttgcga cgtggagctg caaaagctg     480
cgcagcctga cgcgtcgtcg acgcttcgcg cgcccgctgg ccgcattctt atttatcgcc    540
tttatcgcct cgcatgtggt gtatatctgg gccgatgcca acttctatcg cccgatcacc    600
atgcagcgcg ctaacctgcc gctttcgtac ccgatgacgg cgcgacgttt tcttgagaag    660
catggtctgc ttgatgcgca ggagtatcaa cgccgtctta ttgagcaagg taatccagac    720
gccgtttccg ttcagtatcc gttaagcgaa ctgcgctatc gcgatatggg caccgggcag    780
aatgtgctgt tgattactgt cgatggcctg aactactcac gcttcgagaa gcagatgcct    840
gcgctggcag gttttgctga gcaaaatatt tcgttcacgc gccatatgag ctccggcaac    900
actacagaca acggcatctt tggcctgttc tatggcatct cgccgagcta tatggacggc    960
attctgtcga cccgtacgcc tgcggcatta attactgcgc ttaatcagca aggctatcag   1020
ctggggttat tctcatcaga tggctttacc agcccgctgt atcgccaggc attgttgtca   1080
gatttctcga tgccgagcgt acgcacccaa tccgacgagc agaccgccac gcagtggatc   1140
aactggctgg acgctacgc acaagaagat aaccgctggt tctcgtgggt ttctttcaat   1200
ggtactaaca ttgacgacag caatcagcag gcatttgcac ggaaatatag ccgggcggca   1260
ggcaatgtcg atgaccagat caaccgcgtg ctcaatgcac tgcgtgattc tggcaaactg   1320
gacaatacgg tggtgattat cactgccggt cggggtattc cactgagcga agaggaagaa   1380
acctttgact ggtcccacgg tcatctgcag gtgccattag tgattcactg ccaggcacg    1440
ccggcgcagc gtattaatgc tctgactgat cataccgatc tgatgacgac gctgatgcaa   1500
cgcctgctac atgtcagcac acctgccagc gaatattcgc aaggtcagga tttgttcaac   1560
cctcaacgcc gtcattactg ggttaccgca gcggataacg atacgctggc aattaccacc   1620
ccgaaaaaga cgctggtact gaacaataac ggtaaatacc gcacttacaa cttacgtggt   1680
gaaagagtga aagatgaaaa accacagtta agtttgttat tgcaagtgct gacagacgag   1740
aagcgtttta tcgctaactg a                                              1761
```

<210> SEQ ID NO 483
<211> LENGTH: 586
<212> TYPE: PRT
<213> ORGANISM: Escherichia coli

<400> SEQUENCE: 483

```
Met Val Thr His Arg Gln Arg Tyr Arg Glu Lys Val Ser Gln Met Val
1               5                   10                  15

Ser Trp Gly His Trp Phe Ala Leu Phe Asn Ile Leu Leu Ser Leu Val
            20                  25                  30

Ile Gly Ser Arg Tyr Leu Phe Ile Ala Asp Trp Pro Thr Thr Leu Ala
        35                  40                  45

Gly Arg Ile Tyr Ser Tyr Val Ser Ile Ile Gly His Phe Ser Phe Leu
    50                  55                  60

Val Phe Ala Thr Tyr Leu Leu Ile Leu Phe Pro Leu Thr Phe Ile Val
65                  70                  75                  80

Gly Ser Gln Arg Leu Met Arg Phe Leu Ser Val Ile Leu Ala Thr Ala
                85                  90                  95
```

Gly Met Thr Leu Leu Leu Ile Asp Ser Glu Val Phe Thr Arg Phe His
            100                 105                 110

Leu His Leu Asn Pro Ile Val Trp Gln Leu Val Ile Asn Pro Asp Glu
            115                 120                 125

Asn Glu Met Ala Arg Asp Trp Gln Leu Met Phe Ile Ser Val Pro Val
        130                 135                 140

Ile Leu Leu Leu Glu Leu Val Phe Ala Thr Trp Ser Trp Gln Lys Leu
145                 150                 155                 160

Arg Ser Leu Thr Arg Arg Arg Phe Ala Arg Pro Leu Ala Ala Phe
                165                 170                 175

Leu Phe Ile Ala Phe Ile Ala Ser His Val Val Tyr Ile Trp Ala Asp
                180                 185                 190

Ala Asn Phe Tyr Arg Pro Ile Thr Met Gln Arg Ala Asn Leu Pro Leu
            195                 200                 205

Ser Tyr Pro Met Thr Ala Arg Arg Phe Leu Glu Lys His Gly Leu Leu
        210                 215                 220

Asp Ala Gln Glu Tyr Gln Arg Leu Ile Glu Gln Gly Asn Pro Asp
225                 230                 235                 240

Ala Val Ser Val Gln Tyr Pro Leu Ser Glu Leu Arg Tyr Arg Asp Met
                245                 250                 255

Gly Thr Gly Gln Asn Val Leu Leu Ile Thr Val Asp Gly Leu Asn Tyr
            260                 265                 270

Ser Arg Phe Glu Lys Gln Met Pro Ala Leu Ala Gly Phe Ala Glu Gln
        275                 280                 285

Asn Ile Ser Phe Thr Arg His Met Ser Ser Gly Asn Thr Thr Asp Asn
290                 295                 300

Gly Ile Phe Gly Leu Phe Tyr Gly Ile Ser Pro Ser Tyr Met Asp Gly
305                 310                 315                 320

Ile Leu Ser Thr Arg Thr Pro Ala Ala Leu Ile Thr Ala Leu Asn Gln
                325                 330                 335

Gln Gly Tyr Gln Leu Gly Leu Phe Ser Ser Asp Gly Phe Thr Ser Pro
            340                 345                 350

Leu Tyr Arg Gln Ala Leu Leu Ser Asp Phe Ser Met Pro Ser Val Arg
        355                 360                 365

Thr Gln Ser Asp Glu Gln Thr Ala Thr Gln Trp Ile Asn Trp Leu Gly
        370                 375                 380

Arg Tyr Ala Gln Glu Asp Asn Arg Trp Phe Ser Trp Val Ser Phe Asn
385                 390                 395                 400

Gly Thr Asn Ile Asp Asp Ser Asn Gln Gln Ala Phe Ala Arg Lys Tyr
            405                 410                 415

Ser Arg Ala Ala Gly Asn Val Asp Gln Ile Asn Arg Val Leu Asn
        420                 425                 430

Ala Leu Arg Asp Ser Gly Lys Leu Asp Asn Thr Val Val Ile Ile Thr
        435                 440                 445

Ala Gly Arg Gly Ile Pro Leu Ser Glu Glu Glu Thr Phe Asp Trp
450                 455                 460

Ser His Gly His Leu Gln Val Pro Leu Val Ile His Trp Pro Gly Thr
465                 470                 475                 480

Pro Ala Gln Arg Ile Asn Ala Leu Thr Asp His Thr Asp Leu Met Thr
            485                 490                 495

Thr Leu Met Gln Arg Leu Leu His Val Ser Thr Pro Ala Ser Glu Tyr
        500                 505                 510

Ser Gln Gly Gln Asp Leu Phe Asn Pro Gln Arg Arg His Tyr Trp Val

```
                515                 520                 525
Thr Ala Ala Asp Asn Asp Thr Leu Ala Ile Thr Thr Pro Lys Lys Thr
            530                 535                 540

Leu Val Leu Asn Asn Asn Gly Lys Tyr Arg Thr Tyr Asn Leu Arg Gly
545                 550                 555                 560

Glu Arg Val Lys Asp Glu Lys Pro Gln Leu Ser Leu Leu Gln Val
                565                 570                 575

Leu Thr Asp Glu Lys Arg Phe Ile Ala Asn
            580                 585

<210> SEQ ID NO 484
<211> LENGTH: 60
<212> TYPE: DNA
<213> ORGANISM: artificial sequence
<220> FEATURE:
<223> OTHER INFORMATION: primer

<400> SEQUENCE: 484
acaatacggt ggtgattatc actgccggtc ggggtattcc gtgcgtagtc gttggcaagc      60

<210> SEQ ID NO 485
<211> LENGTH: 60
<212> TYPE: DNA
<213> ORGANISM: artificial sequence
<220> FEATURE:
<223> OTHER INFORMATION: primer

<400> SEQUENCE: 485
accgtgggac cagtcaaagg tttcttcctc ttcgctcagt tttagcttcc ttagctcctg      60

<210> SEQ ID NO 486
<211> LENGTH: 60
<212> TYPE: DNA
<213> ORGANISM: artificial sequence
<220> FEATURE:
<223> OTHER INFORMATION: primer

<400> SEQUENCE: 486
agtgctgaca gacgagaagc gttttatcgc taactgatta gtgcgtagtc gttggcaagc      60

<210> SEQ ID NO 487
<211> LENGTH: 60
<212> TYPE: DNA
<213> ORGANISM: artificial sequence
<220> FEATURE:
<223> OTHER INFORMATION: primer

<400> SEQUENCE: 487
accgattgca agtaagatat ttcgctaact gatttataat tttagcttcc ttagctcctg      60

<210> SEQ ID NO 488
<211> LENGTH: 60
<212> TYPE: DNA
<213> ORGANISM: artificial sequence
<220> FEATURE:
<223> OTHER INFORMATION: primer

<400> SEQUENCE: 488
ttaattcgat aaacagaccg tgacacatca cagcctgttt gtgcgtagtc gttggcaagc      60

<210> SEQ ID NO 489
<211> LENGTH: 60
<212> TYPE: DNA
<213> ORGANISM: artificial sequence
<220> FEATURE:
```

```
<223> OTHER INFORMATION: primer

<400> SEQUENCE: 489
ctcaggcggg tgtggtctgg acgttctgat aacagaaaat tttagcttcc ttagctcctg    60

<210> SEQ ID NO 490
<211> LENGTH: 63
<212> TYPE: DNA
<213> ORGANISM: artificial sequence
<220> FEATURE:
<223> OTHER INFORMATION: primer

<400> SEQUENCE: 490
caatacggtg gtgattatca ctgccggtcg gggtattcca tgagtgcgta gtcgttggca    60
agc                                                                  63

<210> SEQ ID NO 491
<211> LENGTH: 60
<212> TYPE: DNA
<213> ORGANISM: artificial sequence
<220> FEATURE:
<223> OTHER INFORMATION: primer

<400> SEQUENCE: 491
gattgcaagt aagatatttc gctaactgat ttataattaa tcaggccggc cataacttcg    60

<210> SEQ ID NO 492
<211> LENGTH: 63
<212> TYPE: DNA
<213> ORGANISM: artificial sequence
<220> FEATURE:
<223> OTHER INFORMATION: primer

<400> SEQUENCE: 492
cgaactgcgc tatcgcgata tgggcaccgg gcagaatgtg tgagtgcgta gtcgttggca    60
agc                                                                  63
```

US 7,915,011 B2

HOST CELL MODIFICATIONS THAT IMPROVE PEPTIDE PRODUCTION AND DOWNSTREAM PROCESSING

This patent application is a continuation-in-part of U.S. patent application Ser. No. 12/398,358, filed Mar. 5, 2009, and incorporated herein by reference.

FIELD OF THE INVENTION

The invention relates to the field of molecular biology, microbiology, and recombinant peptide production. More specifically, it has been discovered that disrupting expression of the genes gcvA and spr in combination with a genetic modification to gene yejM in *Escherichia* host cells significantly improves the settling velocity and/or cell lysis efficiency during downstream processing.

BACKGROUND OF THE INVENTION

Efficient production of bioactive proteins and peptides is a primary function of the biomedical and industrial biotechnology industry. Bioactive peptides and proteins are used as curative agents in a variety of diseases such as diabetes (insulin), viral infections and leukemia (interferon), diseases of the immune system (interleukins), and red blood cell deficiencies (erythropoietin), to name a few. Additionally, large quantities of proteins and peptides are needed for various industrial applications including, but not limited to pulp and paper industries, textiles, food industries, personal care and cosmetics industries, sugar refining, wastewater treatment, production of alcoholic beverages and as catalysts for the generation of new pharmaceuticals.

In biomedical-related fields small peptides are sometimes used as linkers for the attachment of diagnostic and pharmaceutical agents to surfaces (see U.S. Pat. App. Pub. No. 2003/0185870 to Grinstaff et al. and U.S. Pat. No. 6,620,419 to Linter). In the field of personal care, small peptides have been used to couple benefit agents to body surfaces such as hair, skin, nail, and teeth (U.S. Pat. Nos. 7,220,405; 7,309,482; 7,129,326; and 7,285,264; U.S. Pat. App. Pub. Nos. 2002/0098524; 2005/0112692; 2005/0226839; 2007/0196305; 2006/0199206; 2007/0065387; 2008/0107614; 2007/0110686; and 2006/0073111; and Int'l App. Pub. Nos. WO2008/054746; WO2004/048399, and WO2008/073368).

Peptides may be prepared by chemical synthesis or isolated from natural sources. However, these methods are often expensive, time consuming, and characterized by limited production capacity. The preferred method of producing large quantities of peptides or proteins is through the fermentation of recombinant microorganisms engineered to express genes encoding the peptide or protein of interest. However, recombinant microbial peptide production has a number of obstacles to be overcome in order to be cost-effective. For example, peptides produced within recombinant microbial host cell are often degraded by endogenous proteases, which decrease the yield and increase the cost of production. Additionally, microbial production of smaller peptides in high yield may be adversely affected by size and the amino acid composition of the peptide. This is especially evident when the peptide of interest is soluble under typical physiological conditions found within the production host.

One way to mitigate the difficulties associated with recombinant peptide production is the use of chimeric genetic constructs encoding heterologous proteins. Also called fusion proteins, the heterologous proteins typically comprise at least peptide/protein of interest linked to at least one peptide tag. Linking the protein of interest [POI] to the peptide tag, also called solubility tag or inclusion body tag, can make the POI insoluble. The peptide tag may be used to assist protein folding, post expression purification (e.g. His tags), protein passage through the cell membrane as well as to protect the peptide or protein from the action of proteolytic enzymes found within the cell.

Expressing a peptide in an insoluble form by fusing it to a solubility tag—even when the peptide is soluble at normal physiological conditions—facilitates recovery and protects the peptide from degradation. The fusion protein may include at least one cleavable peptide linker separating the solubility tag from the peptide of interest to facilitate subsequent recovery of the POI from the fusion protein. The fusion protein may include a plurality of inclusion body tags, cleavable peptide linkers, and regions comprising the peptide of interest.

Increasing the expression level of the gene encoding the POI can increase the POI yield, e.g., by chromosomal integration of multiple copies of the gene, use of a stronger promoter, and/or by using a high copy expression plasmid. However, the use of high copy plasmids often places an undesirable metabolic burden on the host cell.

Mutations to periplasmic proteases have been reported to increase recombinant antibody fragment accumulation in the *E. coli* periplasm (Chen et al., *Biotech Bioengin* (2004) 85 (5):463-474. Even though single gene knockout libraries are available for *E. coli* (Baba, T., et al., (2006) *Mol. Syst. Biol.* 2: article 2006.0008), down-regulating or disrupting specific genes or combinations of genes in *Escherichia* that significantly increase heterologous peptide production and/or improves downstream processing are not as well known.

Much of the cost associated with recombinant peptide production is associated with the various processing steps often used when recovering the peptide of interest from the cells. Processing steps may include a cell harvest by centrifugation (to "spin down") to recover the cells from the fermentation matrix and homogenization to break up the cells to release the peptide. Host cell modifications that increase the median settling velocity (a parameter to measure the sedimentation rate) may decrease the cost of harvesting cells and/or increase recovery yield by centrifugation. Modifications to the host cell that make them more prone to breakage/lysis during downstream processing, such as during the cell disruption unit operation, is also expected to reduce the cost and/or time associated with processing the recombinant host cells.

The problem to be solved is to provide *Escherichia* cells comprising mutations to endogenous genes that increase the amount of a heterologous peptide produced within the host cell and/or aid the downstream processing of the host cells for recovery of the peptide of interest. Methods to produce and/or use such cells for increasing peptide production and/or improving peptide recovery are also needed.

SUMMARY OF THE INVENTION

The stated problem has been solved through the discovery that disrupting expression of the genes gcvA and spr in combination with a genetic mutation between codons 241 and 568 (corresponding to SEQ ID NO: 482), of gene yejM results in an *Escherichia* host cell characterized by improved peptide production and/or improved downstream processing parameters, such as median settling velocity and/or lysis efficiency when compared to an *Escherichia* host cell lacking the combination of genetic modifications.

In one embodiment, a recombinant *Escherichia* host cell is provided, comprising:

i) a chimeric genetic construct encoding a peptide of interest; and
ii) a set of genetic modifications comprising:
   a) a knockout mutation in gene gcvA;
   b) a knockout mutation in gene spr; and
   c) at least one mutation in the endogenous gene yejM from codon 241 to codon 568 corresponding to SEQ ID NO: 482, that results in at least one amino acid insertion, substitution or deletion.

The recombinant *Escherichia* host cell may lack a down-regulated or disrupted copy of an endogenous protease gene selected from degP, prc, ompT, ptr3, or combinations of these. The recombinant *Escherichia* host cell may further comprise down-regulation or a disruption in an endogenous genetic region selected from the group consisting of the araBAD operon and the slyD gene.

Recombinant *Escherichia* host cells comprising knock out mutations to gcvA and spr in combination with a mutation in yejM between codons 241 and 568 of SEQ ID NO:482, are characterized by an improvement in peptide production. As such, a method of producing a peptide of interest in said recombinant host cell is provided comprising:
   a) providing a recombinant *Escherichia* host cell comprising
      i) at least one chimeric genetic construct encoding a peptide of interest;
      ii) a knockout mutation to a gene selected from the group consisting of gcvA, spr, and a combination thereof; and
      iii) at least one mutation to the endogenous gene yejM between codons 241 and 568 corresponding to SEQ ID NO: 482, that results in at least one amino acid insertion, substitution or deletion;
   b) growing the *Escherichia* host cell of (a) to produce the peptide of interest; and
   c) optionally recovering the peptide of interest produced in step (b).

It has also been discovered that several combinations of the genetic modifications described herein produce *Escherichia* host cells having enhanced parameters associated with several host cell performance parameters such as an increase in heterologous peptide production, an increase in median settling velocity, and an improvement in lysis efficiency when compared to an *Escherichia* host lacking the specified genetic modifications. In another embodiment, a method to optimize downstream processing of a recombinantly-produced peptide is provided comprising:
   a) providing a recombinant *Escherichia* cell comprising at least one chimeric genetic construct encoding a peptide of interest;
   b) introducing a set of genetic modifications to the recombinant *Escherichia* host cell of (a) comprising:
      i) a knockout mutation to gcvA;
      ii) a knockout mutation to spr; and
      iii) at least one mutation to yejM between codons 241 and 568 corresponding to SEQ ID NO: 482, that results in at least one amino acid insertion, substitution or deletion; whereby a modified *Escherichia* host cell is produced;
   c) growing the modified *Escherichia* host cell under conditions whereby the peptide of interest is produced and wherein the modified *Escherichia* host cell demonstrates increased median settling velocity or enhanced cell lysis efficiency as compared to with a non-modified *Escherichia* host cell not having the set of genetic modifications; and
   d) optionally recovering the peptide of interest.

BRIEF DESCRIPTION OF THE BIOLOGICAL SEQUENCES

Figure 1:
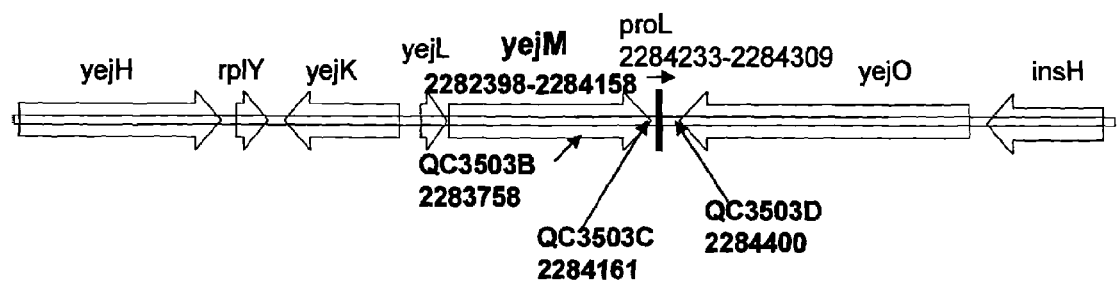
FIG. 1. Genetic organization of the yejM locus and the flanking region in *E. coli* K-12 chromosome. The open arrows represent the genes with their direction of transcription. The vertical bar represents the proL t-RNA gene. The numbers above the genes represent the coordinates of the genes in *E. coli* genome. The numbers below represent the locations of the insertions in the different mutants.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence of a tetracysteine tag that binds to a biarsenical labeling reagent.

SEQ ID NO: 2 is the nucleic acid sequence of peptide expression plasmid pLR199.

SEQ ID NO: 3 is the amino acid sequence of inclusion body tag IBT139.

SEQ ID NO: 4 is the amino acid sequence of a peptide of interest, HC776124.

SEQ ID NO: 5 is the nucleic acid sequence encoding the fusion peptide IBT139-HC776124.

SEQ ID NO: 6 is the amino acid sequence of the fusion peptide IBT139-HC776124.

SEQ ID NO: 7 is the nucleic acid sequence of plasmid pDCQ523.

SEQ ID NO: 8 is the amino acid sequence of inclusion body tag IBT139(5C).

SEQ ID NO: 9 is the nucleic acid sequence of fusion peptide IBT139(5C)-CCPGCC-HC415.

SEQ ID NO: 10 is the amino acid sequence of fusion peptide IBT139(5C)-CCPGCC-HC415.

SEQ ID NO: 11 is the nucleic acid sequence of peptide HC415.

SEQ ID NO: 12 is the amino acid sequence of peptide HC415.

SEQ ID NO: 13 is the nucleic acid sequence of primer Kan2cb-For.

SEQ ID NO: 14 is the nucleic acid sequence of primer Kan2cb-Rev.

SEQ ID NO: 15 is the nucleic acid sequence of gcvA.

SEQ ID NO: 16 is the amino acid sequence of GcvA.

SEQ ID NO: 17 is the nucleic acid sequence of spr.

SEQ ID NO: 18 is the amino acid sequence of Spr.

SEQ ID NO: 19 is the amino acid sequence of a peptide linker.

SEQ ID NO: 20 is the nucleic acid sequence of the araB promoter.

SEQ ID NO: 21 is the nucleic acid sequence of the coding sequence for the slyD gene in *Escherichia coli* strain K-12 substrain MG1655.

SEQ ID NO: 22 is the amino acid sequence of the SlyD protein in *Escherichia coli* strain K-12 substrain MG1655.

SEQ ID NO: 23 is the amino acid sequence of the Caspase-3 cleavage site.

SEQ ID NOs: 24-270 are the amino acid sequences of various body surface-binding peptides. SEQ ID NOs: 24-180 bind to hair, SEQ ID NOs: 176-228 bind to skin, SEQ ID NOs: 229-230 bind to nail, and SEQ ID NOs: 231-2270 bind to a tooth surface, wherein SEQ ID NOs: 231-2250 bind to tooth pellicle and SEQ ID NOs: 251-270 bind to tooth enamel.

SEQ ID NOs: 271-329 are the amino acid sequences of polymer-binding peptides.

SEQ ID NOs: 330-333 are the amino acid sequences of cellulose acetate-binding peptides.

SEQ ID NOS: 334-388 are the amino acid sequences of pigment-binding peptides.

SEQ ID NOs: 389-400 are the amino acid sequences of print media-binding peptides.

SEQ IS NOs: 401-415 are the amino acid sequence of clay-binding peptides.

SEQ ID NOs: 416-441 are calcium carbonate-binding peptides.

SEQ ID NOs: 442-470 are the amino acid sequences of various antimicrobial peptides (U.S. Pat. No. 7,427,656).

SEQ ID NO: 471 is the nucleic acid sequence of plasmid pLR538.

SEQ ID NO: 472 is the nucleic acid sequence encoding the fusion peptide IBT139(5C)-HC415.

SEQ ID NO: 473 is the amino acid sequence of fusion peptide IBT139(5C)-HC415.

SEQ ID NO: 474 is the nucleic acid sequence of plasmid pDCQ702.

SEQ ID NO: 475 is the nucleic acid sequence of plasmid pDCQ703.

SEQ ID NO: 476 is the nucleic acid sequence of plasmid pDCQ704.

SEQ ID NO: 477 is the nucleic acid sequence of the cassette Tn5-Kan-PT5.

SEQ ID NO: 478 is the nucleic acid sequence of the cassette Tn5-Kan-Pcat.

SEQ ID NO: 479 is the nucleic acid sequence of the cassette Tn5-Kan-Ptrc*.

SEQ ID NO: 480 is the nucleic acid sequence of primer Tn5ME.

SEQ ID NO: 481 is the nucleic acid sequence of primer Hind III-out.

SEQ ID NO: 482 is the nucleic acid sequence of the coding region of gene yejM.

SEQ ID NO: 483 is the amino acid sequence of the wild type YejM protein encoded by SEQ ID NO: 482.

SEQ ID NO: 484 is the nucleic acid sequence of primer yejM-catF

SEQ ID NO: 485 is the nucleic acid sequence of primer yejM-catR.

SEQ ID NO: 486 is the nucleic acid sequence of primer proL-catF.

SEQ ID NO: 487 is the nucleic acid sequence of primer proL-catR.

SEQ ID NO: 488 is the nucleic acid sequence of primer proLdown-catF.

SEQ ID NO: 489 is the nucleic acid sequence of primer proLdown-catR.

SEQ ID NO: 490 is the nucleic acid sequence of primer yejM1362-loxKan5'.

SEQ ID NO: 491 is the nucleic acid sequence of primer yejMdown-loxKan3'A.

SEQ ID NO: 492 is the nucleic acid sequence of primer yejM786-loxKan5'.

DETAILED DESCRIPTION

Disrupting expression of the genes gcvA and spr optionally in combination with a genetic mutation between codons 241 and 568 of gene yejM results in an *Escherichia* host cell characterized by improved peptide production when compared to an *Escherichia* host cell lacking the genetic modifications.

Disrupting expression of the endogenous genes gcvA and spr in combination with a genetic mutation between codons 241 and 568 of gene yejM results in an *Escherichia* host cell characterized by improved downstream processing parameters, such as median settling velocity and/or lysis efficiency when compared to an *Escherichia* host cell lacking the combination of genetic modifications. In a preferred embodiment, the modified *Escherichia* host cell comprises (in addition to the double knockout of gcvA and spr) the genetic mutation between codons 241 and 568 of the endogenous gene yejM for use in a method to improve downstream processing parameters.

The modified recombinant *Escherichia* host cells may lack any genetic modification, such as disrupted expression, to the endogenous protease genes degP, prc, ompT, ptr3, and combinations thereof.

The heterologous peptides produced within the modified microbial host cells may be produced and accumulate in the form of inclusion bodies. The soluble single chain peptides may be fusion peptides comprising at least one solubility tag (inclusion body tag). The heterologous peptides produced within the modified host cell may range from about 14 to about 600 amino acids in length. In one aspect, the heterologous peptides produced within the host cell are single chain peptides. In a further aspect, the single chain peptides lack any immunoglobulin folds.

The following definitions are used herein and should be referred to for interpretation of the claims and the specification. Unless otherwise noted, all U.S. Patents and U.S. Patent Applications referenced herein are incorporated by reference in their entirety.

As used herein, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. This means a composition, a mixture, a process, a method, an article, or an apparatus that comprises a list of elements is not limited to only those elements but may include others not expressly listed or inherent to it. As used herein, "or" refers to an inclusive and an exclusive "or". For example, a condition A or B is satisfied by any one of the following: A is true (or present) and B is false (or not present), A is false (or not present) and B is true (or present), and both A and B are true (or present).

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "invention" or "present invention" is a non-limiting term and is intended to encompass all possible variations as described in the specification and recited in the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. The peptides may comprise L-amino acids.

As used herein, the terms "peptide of interest", "POI", "gene product", "target gene product", and "target coding region gene product" refer to the desired heterologous peptide/protein product encoded by the recombinantly expressed foreign gene. The peptide of interest may include any peptide/protein product including, but not limited to proteins, fusion proteins, enzymes, peptides, polypeptides, and oligopeptides. The peptide of interest ranges in size from 14 to 600 amino acids in length. The peptide of interest is not GcvA, Spr, or YejM. The peptide of interest may have strong affinity for a target surface, such as a body surface. The peptide of interest may have affinity for a body surface selected from the group consisting of hair, skin, nails, tooth, and tooth pellicle. In one embodiment, the peptide of interest is a single chain peptide from 14 to 600 amino acids in length and lacks any immunoglobulin folds.

As used herein, the terms "bioactive" or "peptide of interest activity" refer to the activity or characteristic associated with the peptide and/or protein of interest. The bioactive peptides may be used as, for example, curative agents for diseases (e.g., insulin, interferon, interleukins, anti-angiogenic peptides (U.S. Pat. No. 6,815,426); polypeptides that bind to defined cellular targets such as receptors, channels, lipids, cytosolic proteins, and membrane proteins; peptides having antimicrobial activity; peptides having an affinity for a particular material (e.g., hair-binding polypeptides, skin-binding polypeptides, nail-binding polypeptides, tooth-binding peptides (include both tooth enamel and tooth pellicle-binding peptides), print media-binding peptides, cellulose-binding polypeptides, polymer-binding polypeptides, clay-binding polypeptides, calcium carbonate-binding peptides, cellulose acetate-binding peptides, carbon nanotube-binding polypeptides and peptides that have an affinity for particular animal or plant tissues) for targeted delivery of benefit agents.

As used herein, the term "median settling velocity" or "settling velocity" means the settling velocity as determined by analytical centrifugation. The median settling velocity may be determined using a LUMiSizer® (L.U.M. GmbH, Berlin, Germany). This instrument measures the intensity of transmitted light as a function of time and position over the entire sample length simultaneously. This characterization method is also described by Frömer and Lerche (Frömer, D. and Lerche, D., (2002). *Archive of Applied Mechanics* 72(2): 85-95). The light source sends out parallel NIR-light which is passed through the sample vials lying on the centrifuge rotor. The distribution of local transmission is recorded over the entire sample length by the CCD-line detector. The vials containing the samples are centrifuged at constant speed, thus accelerating the sedimentation process. Based on these space- and time-resolved light transmission profiles, the settling velocity distribution of the cell population can be calculated. The median of this distribution is used here to characterize the settling characteristics at the defined experimental conditions.

As used herein, the term "lysis efficiency" means the extent of cells lost viability after each passage of process by French press. French press is a familiar high-pressure homogenizer for the laboratory, which uses a motor-driven piston inside a steel cylinder to develop high pressures to the samples. It works similarly as the commercial scale high-pressure homogenizers by forcing cell suspensions through a very narrow channel under high pressure. (Hopkins, T. R., "Physical and chemical cell disruption for the recovery of intracellular proteins" in *Purification and Analysis of Recombinant Proteins* (1991) edited by R. Seetharam, et al., pp 57-84. Marcel Dekker, Inc., New York, N.Y.). The efficiency of cell breakage or the lysis efficiency may be evaluated by viable cell counts using serial dilution. As illustrated in the present examples, serial dilutions were made from the samples prior to French Press (F0) and post each passage of French Press (F1, F2 F3). Certain volume of each dilutions were plated on appropriate agar plates and plates were incubated for overnight growth at 37° C. The viable cell counts were enumerated and the percentage of viable cells (100%–lysis %) after each passage of French Press was calculated relative to the unprocessed F0 sample.

As used herein, the "benefit agent" refers to a molecule that imparts a desired functionality or benefit when applied or coupled to a target surface. The present peptide reagents may be used to couple a benefit agent to a target surface, such as a body surface. The peptide reagent may couple a benefit agent to a body surface by forming a complex between the peptide reagent, the benefit agent, and the body surface. The peptide reagent is applied to the body surface prior to the application of the benefit agent (i.e., a sequential application). The benefit agent may be a peptide or the peptide reagent (e.g. condition peptides or antimicrobial peptides) or may be one or more molecules bound to (covalently or non-covalently), or associated with, a peptide reagent having affinity for a target surface. The benefit agent may be a particulate benefit agent. The term "particulate benefit agent' is a general term relating to a particulate substance, which when applied to a body surface provides a cosmetic or prophylactic effect. Particulate benefit agents typically include pigments, particulate conditioners, inorganic sunscreens and the like along with other particulate substances commonly used in the personal care industry.

As used herein, the term "$MB_{50}$" refers to the concentration of the binding peptide that gives a signal that is 50% of the maximum signal obtained in an ELISA-based binding assay (see Example 9 of U.S. Published Pat. App. Pub. No. 2005/0226839; hereby incorporated by reference). The $MB_{50}$ provides an indication of the strength of the binding interaction or affinity of the components of the complex. The lower the value of $MB_{50}$, the stronger the interaction of the peptide with its corresponding substrate.

As used herein, the terms "binding affinity" or "affinity" refers to the strength of the interaction of a binding peptide (e.g. a peptide having affinity for a specified target surface)) with its respective substrate. The binding affinity may be reported in terms of the $MB_{50}$ value as determined in an ELISA-based binding assay or as a $K_D$ (equilibrium dissociation constant) value, which may be deduced using surface plasmon resonance (SPR). The lower the value of $MB_{50}$ or $K_D$, the stronger affinity of the peptide interacting with its corresponding substrate.

As used herein, the term "strong affinity" refers to a binding affinity, as measured as an $MB_{50}$ or $K_D$ value, of $10^{-5}$ M or less, preferably $10^{-6}$ M or less, preferably less than $10^{-7}$ M, more preferably less than $10^{-8}$ M, more preferably less than $10^{-9}$ M, and most preferably less than $10^{-10}$ M.

As used herein, the term "target surface-binding peptide" refers to a single chain peptide having strong affinity (defined as having a $K_D$ value less than $10^{-4}$ M or an $MB_{50}$ value of less than $10^{-4}$) for a target surface. The peptide of interest may be a single target surface-binding peptide ranging in size from 7 to 60 amino acids in length, or may be a single chain, peptide-based reagent comprising one or more target surface-binding peptides, wherein the length of the peptide-based reagent ranges from 14 to 600 amino acids in length. The target surface-binding peptide may be a body surface-binding peptide.

As used herein, the term "body surface-binding peptide" refers to a peptide having strong affinity for a body surface. Examples of body surfaces include, but are not limited to hair, skin, nail, and tooth. The body surface-binding peptides are typically used to couple a personal or health care benefit agent to the body surface. These agents include colorants, conditioners, and antimicrobials, to name a few. Means to identify suitable body-surface binding peptides are well known in the art and may include biopanning techniques such as phage display, bacterial display, yeast display, ribosome display, and mRNA-display. The body surface-binding peptide may also be empirically-generated.

As used herein, "HBP" means hair-binding peptide. As used herein, the term "hair-binding peptide" refers to a peptide that binds with high affinity to hair. Examples of hair-binding peptides have been reported (U.S. patent application Ser. No. 11/074,473 to Huang et al.; Int'l App. Pub. No. WO 0179479; U.S. Pat. App. Pub. No. 2002/0098524 to Murray et al.; U.S. Pat. App. Pub. No. 2003/0152976 to Janssen et al.; Int'l App. Pub. No. WO 2004048399; U.S. patent application Ser. No. 11/512,910, and U.S. patent application Ser. No. 11/696,380). Examples of hair-binding peptides are provided as SEQ ID NOs: 24-180. The hair-binding peptides may be from about 7 amino acids to about 60 amino acids, more preferably, from about 7 amino acids to about 25 amino acids, most preferably from about 7 to about 20 amino acids in length.

As used herein, "SBP" means skin-binding peptide. As used herein, the term "skin-binding peptide" refers to a peptide sequence that binds with high affinity to skin. Examples of skin-binding peptides have also been reported (U.S. patent application Ser. No. 11/069,858 to Buseman-Williams; Inn App. Pub. No. WO 2004/000257; and U.S. patent application Ser. No. 11/696,380). Skin as used herein as a body surface will generally comprise a layer of epithelial cells and may additionally comprise a layer of endothelial cells. Examples of skin-binding peptides are provided as SEQ ID NOs: 176-228. The skin-binding peptides may be from about 7 amino acids to about 60 amino acids, more preferably, from about 7 amino acids to about 25 amino acids, most preferably from about 7 to about 20 amino acids in length.

As used herein, "NBP" means nail-binding peptide. As used herein, the term "nail-binding peptide" refers to a peptide that binds with high affinity to nail. Examples of nail-binding peptides have been reported (U.S. patent application Ser. No. 11/696,380). Examples of nail-binding peptides are provided as SEQ ID NOs: 229-230. The nail-binding peptides may be from about 7 amino acids to about 60 amino acids, more preferably, from about 7 amino acids to about 25 amino acids, most preferably from about 7 to about 20 amino acids in length.

As used herein, "TBP" means tooth-binding peptide. A tooth-binding peptide is a peptide that binds with high affinity to a mammalian or human tooth surface. As used herein, the term "tooth-binding peptide" will refer to a peptide that binds to tooth enamel or tooth pellicle. The tooth-binding peptides may be from about 7 amino acids to about 60 amino acids in length, more preferably, from about 7 amino acids to about 25 amino acids in length, most preferably from about 7 to about 20 amino acids in length. The tooth-binding peptides may be combinatorially-generated peptides. Examples of tooth-binding peptides having been disclosed in co-pending and co-owned U.S. application Ser. No. 11/877,692 and are provided as SEQ ID NOs: 231-270.

As used herein, the term "tooth surface" refers to a surface comprised of tooth enamel (typically exposed after professional cleaning or polishing) or tooth pellicle (an acquired surface comprising salivary glycoproteins). Hydroxyapatite can be coated with salivary glycoproteins to mimic a natural tooth pellicle surface (tooth enamel is predominantly comprised of hydroxyapatite).

As used herein, the terms "pellicle" and "tooth pellicle" refer to the thin film (typically ranging from about 1 μm to about 200 μm thick) derived from salivary glycoproteins which forms over the surface of the tooth crown. Daily tooth brushing tends to only remove a portion of the pellicle surface while abrasive tooth cleaning and/or polishing (typically by a dental professional) will exposure more of the tooth enamel surface.

As used herein, the terms "enamel" and "tooth enamel" refer to the highly mineralized tissue which forms the outer layer of the tooth. The enamel layer is composed primarily of crystalline calcium phosphate (i.e. hydroxyapatite; $Ca_5(PO_4)_3OH$) along with water and some organic material. The tooth surface may be tooth enamel or tooth pellicle.

As used herein, the terms "peptide linker", "linker" and "peptide spacer" refer to a peptide used to link together two or more target surface-binding peptides. An example of a peptide linker is provided as SEQ ID NO: 19.

As used herein, the term "bridge", "peptide bridge", and "bridging element" refer to a linear peptide used to couple a target-surface binding domain ("target surface-binding hand") to a peptide domain coupled to the surface of particulate benefit agent (i.e. covalent or non-covalent coupling). The peptide bridge may range in size from 1 to 60 amino acids in length, preferably 6 to 40 amino acids in length.

As used herein, the terms "coupling" and "coupled" refer to any chemical association and may include both covalent and non-covalent interactions in one coupling event. Coupling may also refer to separate, individual covalent interaction or separate, individual non-covalent interaction.

As used herein, the terms "hand", "target surface hand", and "target surface-binding domain" refer to a single chain peptide comprising of at least two target surface-binding peptides linked together by at least one peptide linker. The target surface-binding peptides may be biopanned from a random peptide library using a method selected from the group consisting of phage display, bacterial display, yeast display, ribosome display, and mRNA-display. The target-surface binding hand may comprise two target surface-binding peptides linked together by a peptide linker.

As used herein, the terms "peptide-based reagent" and "peptide reagent" refer to a single chain peptide comprising at least one target surface-binding domain having strong affinity for a target surface.

As used herein, the terms "body surface-binding hand" and "body surface-binding domain" refer to a single chain peptide comprising two or more body surface-binding peptides (BSBPs) linked together by at least one peptide linker. The body surface-binding domain may comprise two body surface-binding peptides linked together by a peptide linker.

As used herein, the terms "benefit agent-binding hand" or "benefit agent-binding domain" refer to a single chain peptide domain comprising two or more benefit agent-binding peptides (BABPs) coupled together by at least one peptide linker. The benefit agent-binding domain may comprise two benefit agent-binding peptides linked together by a peptide linker.

As used herein, the terms "solubility tag" and "inclusion body tag" and the abbreviation "IBT" refer to a polypeptide that promotes or enhances the formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies, also called inclusion bodies, within the host cell. The fusion protein comprises a portion having an inclusion body tag and a peptide/protein of interest. The polypeptide/protein of interest may be separated from the inclusion body tags using cleavable peptide linker elements (See U.S. patent application Ser. Nos. 11/641,936, 11/641,273, and 11/782,836).

As used herein, the terms "cleavable linker element" and "cleavable peptide linker" are used interchangeably and refer to cleavable peptide segments typically incorporated between an inclusion body tag and the peptide of interest. After the inclusion bodies are separated and/or partially-purified or purified from the cell lysate, the cleavable linker element can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary.

The inclusion body tag(s) and the peptide of interest may exhibit a different solubility in a defined medium, typically aqueous, thereby facilitating separation of the inclusion body tag from the peptide of interest. Preferably, the inclusion body tag is insoluble in an aqueous solution while the protein/peptide of interest is appreciably soluble in an aqueous solution. The pH, temperature, and/or ionic strength of the aqueous solution can be adjusted to facilitate recovery of the peptide of interest. The differential solubility between the inclusion body tag and the peptide of interest may occur in an aqueous solution having a pH of 5 to 10 and a temperature range of 15° C. to 50° C. The cleavable peptide linker may be from 1 to about 50 amino acids in length, preferably from 1 to about 20 amino acids in length. An example of an enzymatically cleavable peptide linker is provided by SEQ ID NO: 23 (Caspase-3 cleavage sequence). The cleavable linker may be an acid cleavable aspartic acid-proline dipeptide (D-P) moiety. The cleavable peptide linkers may be incorporated into the fusion proteins using any number of techniques well known in the art.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, an expression cassette, a vector, a plasmid and the like.

As used herein, the term "endogenous gene" refers to a native gene in its natural location in the genome of an organism.

As used herein, a "foreign gene" refers to a gene not normally found in the host organism, but that is introduced into the host organism by gene transfer. Foreign genes can comprise native genes inserted into a non-native organism, or chimeric genes.

As used herein, the term "heterologous" with respect to sequence within a particular organism/genome indicates that the sequence originates from a foreign species, or, if from the same species, is substantially modified from its native form in composition and/or genomic locus by deliberate human intervention. Thus, for example, heterologous gene expression refers to the process of expressing a gene from one organism/genome by placing it into the genome of a different organism/genome.

As used herein, the term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

As used herein, the term "*Escherichia*" refers to a genus of Gram-negative, non-spore forming, facultatively anaerobic, rod-shaped bacteria from the family Enterobacteriaceae. The genus *Escherichia* include various species, such as *Escherichia coli*. The *Escherichia* host cell is an *Escherichia coli* cell. The *Escherichia coli* cell may be derived from an *Escherichia coli* K-12 strain.

As used herein, the term "peptide-based" refers to an interfacial material comprised of a compound pertaining to or having the nature or the composition of the peptide class. Interfacial refers to the quality of the peptide-based material described herein as connecting one material to another.

As used herein, the terms "fusion protein" and "fusion peptide" are interchangeable and refer to a polymer of amino acids (peptide, oligopeptide, polypeptide, or protein) comprising at least two portions, each portion comprising a distinct function. A first portion of the fusion peptide may comprise at least one inclusion body tag and a second portion of the fusion peptide may comprise at least one peptide of interest. The fusion protein may additionally include at least one cleavable peptide linker that facilitates chemical and/or enzymatic cleavage and separation of the inclusion body tag(s) and the peptide(s) of interest.

As used herein, the term "immunoglobulin fold" refers to a common all-β protein fold that consists of a 2-layer sandwich of ~7 antiparallel β-strands arranged in two β-sheets. The backbone switches repeatedly between the two β-sheets. Typically, the pattern is (N-terminal β-hairpin in sheet 1)-(β-hairpin in sheet 2)-(β-strand in sheet 1)-(C-terminal β-hairpin in sheet 2). The cross-overs between sheets form an "X", so that the N- and C-terminal hairpins are facing each other.

As used herein, the term "polymer-binding peptide" refers to peptide sequences that bind with high affinity to a specified polymer (U.S. patent application Ser. No. 11/516,362). Examples of polymer-binding peptides are provided as SEQ ID NOs: 271-329.

As used herein, the term "pigment" refers to an insoluble colorant and may include a wide variety of organic and inorganic pigments alone or in combination.

As used herein, the terms "iron oxide-based pigment" and "iron oxide pigment" refer to a pigment particle comprised primarily of an iron oxide. Iron oxide pigments may vary in color (red, yellow, brown, and black tones) due to minor impurities and/or the size of the pigment particle. The iron oxide pigment may be a cosmetically acceptable iron oxide pigment. Cosmetically acceptable iron oxide pigments are commercially available from various companies, such as Sensient Technologies Corp, Milwaukee, Wis. The iron oxide is selected from the group consisting of ferric oxide ($Fe_2O_3$), ferrous ferric oxide ($Fe_3O_4$), and mixtures of $Fe_2O_3$ and $Fe_3O_4$. The iron oxide may be ferric oxide $Fe_2O_3$. The iron oxide-based pigment may be at least partially coated with silica.

As used herein, the term "pigment-binding peptide" refers to a peptide that binds with high affinity to a pigment particle. Examples of pigment-binding peptides are provided as SEQ ID NOs 334-388.

As used herein, an "antimicrobial peptide" is a peptide having the ability to kill microbial cell populations (U.S. Pat. No. 7,427,656). Examples of antimicrobial peptides are provided as SEQ ID NOs: 442-470.

As used herein, the term "print medium-binding peptide" refers to a peptide that binds to a printer medium such as cotton, cellulose, paper, and cotton/polyester blends. Examples of print media-binding peptides are provided as SEQ ID NOs: 389-400.

As used herein, "clay-binding peptide" refers to a peptide that binds with strong affinity to clay (U.S. patent application Ser. No. 11/696,380). Examples of clay-binding peptides are provided as SEQ ID NOs: 401-415.

As used herein, "calcium carbonate-binding peptide" refers to a peptide that binds with strong affinity of calcium carbonate (U.S. patent application Ser. No. 11/828,539). Examples of calcium carbonate-binding peptides are provided as SEQ ID NOs: 416-441.

As used herein, the term "operably-linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). The definition of "operably linked" may also be extended to describe the products of chimeric genes. As such, "operably-linked" may also refer to the linking of two or more target surface-binding peptides by at least one peptide linker.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

-continued

| Amino Acid | Three-Letter Abbreviation | One-Letter Abbreviation |
| --- | --- | --- |
| Tyrosine | Tyr | Y |
| Valine | Val | V |
| Miscellaneous (or as defined herein) | Xaa | X |

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, $5^{th}$ Ed. Current Protocols and John Wiley and Sons, Inc., N.Y., 2002.

Decreased or Disrupted Expression of Endogenous *Escherichia* Genes

Described herein are methods of increasing the production of a protein or peptide of interest by disrupting both genes gcvA and spr in a recombinant *Escherichia* host cell which either natively or through genetic engineering encodes a protein of interest [POI]. In one embodiment, the fusion protein includes at least one POI linked to a solubility tag (inclusion body tag). Once produced by the host cell, the fusion protein is insoluble at normal physiological conditions, thereby avoiding cellular protease of the POI. Also described herein are recombinant *Escherichia* host cells having disruptions in both genes gcvA and spr and which thereby increase the production of the peptide or protein of interest.

Several genes from a random transposon insertion library were identified as possibly responsible for increasing peptide production by measuring an increase in fluorescence. This was done by using a fluorescent labeling reagent to identify the fusion peptide production. The increase in fluorescence had been initially attributed to an increase in the amount of fusion peptide produced.

Further analysis confirmed that the amount of POI produced increased relatively to the control under identical conditions for the disrupted gcvA or spr gene. A knockout mutant containing mutations to both gene gcvA and gene spr significantly increased heterologous peptide production. The increase in heterologous peptide production may be at least 1.25 fold, 1.5 fold, 2.0 fold, 2.5 fold, 3.0 fold, 3.5 fold, 4.0 fold, 4.5 fold or 5.0 fold when compared to a control *Escherichia* cell essentially identical to the mutant host cell except for the knockout to gcvA and spr grown under identical conditions.

PCR analysis was performed to confirm the clean in-frame deletion of gcvA and spr. Decreased expression (including disrupted expression of the functional gene product) of gcvA and spr increased the amount of the heterologous fusion peptide, including the POI. As used herein, the terms "disrupted functional expression", "disrupted expression", and "disrupted gene" refer to a genetic modification to a specified gene that stops functional expression of the gene's product, such as an active enzyme, functional RNA, and/or functional regulatory protein.

Generally, disruption in the production a gene product can be accomplished by, e.g., an insertion, deletion, or substitution to a portion of the gene, which results in no or reduced formation of the active gene product. The disruption may preferably be a partial or complete deletion of the gene. A genetic modification that complete abolishes production of the gene product or produces a gene product no longer having its associated function or activity may be referred to as a "knockout" or a "knockout mutation" and may be denoted by the symbol "Δ". For example, "Δspr" would refer to a knockout of the spr gene that complete disrupted production of a functional Spr protein.

When the sequence of the gene to be disrupted is known, down regulating gene expression may be referred to as "targeted" gene disruption and involves creating genetic cassettes that include DNA to be inserted into the to-be-disrupted gene. This DNA is often a genetic marker and is flanked by sequence(s) having a high degree of homology to a portion of the targeted gene. Introduction of the cassette into the host cell results in insertion of the foreign DNA into the targeted gene via native DNA replication mechanisms of the cell (Hamilton et al., *J. Bacteriol.*, 171:4617-4622 (1989); Balbas et al., *Gene,* 136:211-213 (1993); Gueldener et al., *Nucleic Acids Res.,* 24:2519-2524 (1996); and Smith et al., *Methods Mol. Cell. Biol.,* 5:270-277 (1996)) and interferes with transcription of the targeted gene, which produces no mRNA transcripts from which to translate a gene product.

Down regulation of expression does not always require completely eliminating all expression of the gene and its corresponding gene product. Targeted genes may be down-regulated using several other techniques known in the art. For example, target genes can be modified to be under the control of non-native promoters. When desired that a pathway and/or functional gene product operate at a particular point in a cell cycle or during a fermentation run, regulated or inducible promoters can replace the native promoter of the target gene. Similarly, the native or endogenous promoter can be modified to decrease gene expression. For example, endogenous promoters can be altered in vivo by mutation, deletion, and/or substitution (see, Kmiec, U.S. Pat. No. 5,565,350; Zarling et al., PCT/US93/03868).

Down regulating expression can involve antisense technology when the sequence of the target gene is known. Here, a nucleic acid segment from the desired gene is cloned and operably linked to a promoter such that the anti-sense strand of RNA will be transcribed. This construct is then introduced into the host cell and the antisense strand of RNA is produced, which inhibits gene expression by preventing the accumulation of mRNA that encodes the POI. Antisense technology is within the skill of the art. That is, a skilled artisan understands that achieving a down-regulated expression through antisense genes involves the use of chimeric genes having various regulatory elements.

Besides targeted gene disruption and antisense technology, other down regulation methods exist that do not require knowing the sequence of the to-be-disrupted gene. For example, cells may be exposed to UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., (hereinafter "Brock") or Deshpande, Mukund V., *Appl. Biochem. Biotechnol.,* 36:227 (1992) (hereinafter "Deshpande").

Transposon mutagenesis represents another non-specific method of gene disruption and is exemplified herein. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid molecule in the presence of the transposase, the transposable element will randomly insert into the nucleic acid molecule. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Nucleic acid hybridization may also be used to identify substantially similar nucleic acid sequences. The present nucleic acid molecules may be used to identify genes encoding substantially similar polypeptides/proteins expected to have similar function. Nucleic acid hybridization may be conducted under stringent conditions.

Substantially similar sequences are defined by their ability to hybridize, under the following stringent conditions (0.1× SSC, 0.1% SDS, 65° C. and washed with 2×SSC, 0.1% SDS followed by 0.1×SSC, 0.1% SDS, 65° C.) with a sequence selected from the group consisting of SEQ ID NOs. 15 and 17.

Each of the proposed modifications is well within the routine skill in the art (see Sambrook and Russell, supra). Moreover, the skilled artisan recognizes that substantially similar sequences are also encompassed by the present invention. Furthermore, the genetic modifications illustrated herein in *Escherichia coli* should apply to other members of the genus *Escherichia*.

As illustrated herein, the *Escherichia* host cell may also have a knockout to the endogenous chromosomal araBAD operon (a pBAD expression vector and arabinose induction was used to drive expression of the chimeric gene encoding the fusion peptide) and a knockout to the slyD gene (to remove possible binding between the LUMIO™ biarsenical labeling reagent and cysteine rich sequences in slyD). The recombinant *Escherichia* production host may comprise decreased expression and/or a disruption (such as a knockout) in the endogenous araBAD operon, the slyD gene, or a combination thereof.

Genetic Modification to yejM

The yejM gene comprises a coding region of approximately 1761 nucleotides encoding a 586 amino acid protein (YejM) that has been reported to be an essential protein with unknown function. Membrane topology prediction indicated that YejM is an inner membrane protein that contains five putative transmembrane helices on the N-terminal portion of the protein and a C-terminal periplasmic domain (Rapp, M. et al., *Protein Sci.* (2004) 13:937-945; Daley et al., *Science* (2005) 308:1321-1323). The periplasmic domain of YejM has high sequence homology to sulfatases/phosphatases. The yejM null mutation is lethal (De Lay, N., and Cronan, J., *Genetics* (2008) 178:1327-1337). The mutant strain designated as LH530 with a G570A mutation, which retained its N-terminal domain (190 amino acids) but lacked its C-terminal domain, was temperate sensitive.

As described in the present examples, transposon insertions were isolated and mapped to nucleotides ranging from 723 to 1706, which corresponds to codons 241 through 568.

As such, recombinant *Escherichia* host cells are provided herein comprising at least one mutation in the endogenous yejM gene from codon 241 to codon 568; wherein the mutation results in at least one insertion, deletion or substitution within the corresponding amino acid gene product and is characterized by the desired phenotype (i.e. an increase in heterologous peptide production, an increase in median settling velocity, and/or an increase in cell lysis efficiency).

As described herein, a "truncation mutation" is a mutation in the coding region of an expressible nucleic acid molecule whereby a stop codon is introduced prematurely within the normal coding sequence, resulting in the production of a gene product (such as a protein or peptide) that is shorter in length from the C-terminus relative to the normal wild type gene product. Mutations introducing premature stop codons closer to the 5' portion of the coding sequence produce shorter gene products.

In one embodiment, the mutation is a truncation mutation or a transposon insertion from codon 241 through codon 568 of the endogenous yejM gene. In a preferred embodiment, the truncation mutation or transposon insertion is in the corresponding codons of SEQ ID NO: 482.

In one embodiment, the truncation mutation occurs at or after codon 262 of the endogenous yejM gene. In a preferred embodiment, the truncation mutation occurs at codon 262 (corresponding approximately to "ΔyejM324") or codon 454 (corresponding approximately to "ΔyejM132").

In another embodiment, the modified *Escherichia* host cell comprising a truncation mutation yejM is not temperature sensitive.

A BLASTP search (version 2.2.21 using default parameters as set by the National Center for Biotechnology Information, Bethesda, Md.) of the GENBANK® nr database returned many hits with very high amino acid identify (many with 97% identity or higher to SEQ ID NO: 483) to sequences from various species/strains from the genus *Escherichia* as well as the genus *Shigella*. In one embodiment, the host cell is a member of the genus *Escherichia*. In another embodiment, the host cell is *Escherichia coli*. In a further embodiment, the *Escherichia coli* is a K-12 strain or a B-strain.

Peptide of Interest

The function of the peptide of interest is not limited by the present method and may include, but is not limited to bioactive molecules that act as curative agents for diseases, such as insulin, interferon, interleukins, peptide hormones, immunoglobulins, antibodies, anti-angiogenic peptides, and peptides that bind to and affect defined cellular targets such as receptors, channels, lipids, cytosolic proteins, and membrane proteins (see U.S. Pat. No. 6,696,089); peptides having an affinity for a particular material, such as biological tissues, biological molecules, hair-binding peptides (see U.S. patent application Ser. No. 11/074,473; Int'l Pat. App. No. WO 0179479; U.S. Pat. App. Pub. No. 2002/0098524; U.S. Pat. App. Pub. No. 2003/0152976; Int'l Pat. App. No. WO 04048399; U.S. Pat. App. Pub. No 2007/0067924; and U.S. Pat. App. Pub. No. 2007/0249805), skin-binding peptides (see U.S. Pat. No. 7,309,482; Inn Pat. App. No. WO 2004/000257; and U.S. Pat. App. Pub. No. 2007/0249805), nail-binding peptides (see U.S. Pat. App. Pub. No. 2007/0249805), cellulose-binding peptides, polymer-binding peptides (see U.S. Pat. App. Pub. Nos. 2007/0141629, 2007/0264720, 2008/0207872, 2007/0141628, and 2007/0261775), clay-binding peptides, and carbon nanotube binding peptides) for targeted delivery of at least one benefit agent (see U.S. patent application Ser. No. 10/935,642; U.S. patent application Ser. No. 11/074,473; and U.S. Pat. App. Pub. No. 2007/0249805).

The peptide of interest may be a single chain peptide ranging in size from about 14 to about 600 amino acids in length and lacks an immunoglobulin fold. The peptide of interest may range in size from 14 to 400 amino acids in length, 14 to 300 amino acids in length, or 14 to about 200 amino acids in length. The peptide of interest may be produced in an insoluble form within the *Escherichia* host cell, such as in the form of inclusion bodies. The peptide of interest may be produced and accumulated in the cytoplasm as inclusion bodies. The peptide of interest may be a fusion peptide. The fusion peptide may be comprised of at least one solubility tag, such as an inclusion body tag. In one embodiment, the peptide of interest is optionally recovered from the recombinant host cell. In another embodiment, the peptide of interest is recovered from the host cell.

Single Chain Peptides Having Affinity for a Target Surface

Proteinaceous materials having strong affinity for a body surface can target delivery of one or more personal care benefit agents. Some of these materials comprise or derive from immunoglobulins or immunoglobulin fragments (antibodies, antibody fragments, $F_{ab}$, single-chain variable fragments (scFv), and *Camilidae* $V_{HH}$) having affinity for the target surface. Other such proteinaceous materials comprise non-immunoglobulin derived scaffold proteins. Further, these materials for delivery of a personal care benefit agent can include a single chain, linear peptide.

The peptide of interest used in the fusion proteins described herein is or is part of a proteinaceous material that has at least one domain having strong affinity for a target surface but does not comprise an immunoglobulin fold or underlying scaffold support. Thus, the POI preferably comprise at least one single chain peptide. Moreover, the peptide of interest described herein is heterologous to the *Escherichia* host cell and may be produced in the cytoplasm and not targeted for secretion and/or accumulation in the periplasm.

Single-chain peptides that target surfaces can be identified and isolated from peptide libraries using any number of biopanning techniques well known to those skilled in the art including, but not limited to bacterial display, yeast display, combinatorial solid phase peptide synthesis, phage display, ribosome display, and mRNA display. Techniques to generate random peptide libraries are described in Dani, M., *J. of Receptor & Signal Transduction Res.*, 21(4):447-468 (2001). Phage display libraries are available commercially from companies such as New England BioLabs (Beverly, Mass.).

The peptide of interest may be a peptide-based reagent comprising a plurality of biopanned target surface-binding peptides coupled together (optionally through one or more spacers) to form at least one target surface binding domain. The peptide of interest may comprise multiple target surface-binding domains, wherein each domain may have affinity for the same or a different target surface. The individual biopanned target surface-binding peptides are typically about 7 to about 60 amino acids in length and often have a binding affinity (as measured or reported as an $MB_{50}$ or $K_D$ value) of $10^{-5}$ M or less for the surface of the target material. The individual biopanned target surface-binding peptides may be from about 7 amino acids to about 60 amino acids in length, more preferably, from about 7 amino acids to about 25 amino acids in length, most preferably from about 7 to about 20 amino acids in length. The peptide of interest may also be an individual target surface-binding peptide.

Examples of single chain peptide-based reagents having affinity for at least one target surface include, but are not limited to body surfaces such as hair, skin, nail, and teeth (U.S. Pat. Nos. 7,220,405; 7,309,482; and 7,285,264; U.S. Pat. App. Pub. Nos. 2005/0226839; 2007/0196305; 2006/

0199206; 2007/0065387; 2008/0107614; 2007/0110686; and 2006/0073111; and Int'l Pat. App. Pub. Nos. WO2008/054746; WO2004/048399, and WO2008/073368) as well as other surfaces such as pigments and miscellaneous print media (U.S. Pat. App. Pub. No. 2005/0054752), and various polymers such as polymethylmethacrylate (U.S. Pat. App. Pub. No. 2007/0265431), polypropylene (U.S. Pat. App. Pub. No. 2007/0264720), nylon (U.S. Pat. App. Pub. Nos. 2007/0141629 and 2003/0185870), polytetrafluoroethylene (U.S. Pat. App. No. 11/607,734), polyethylene (U.S. Pat. App. Pub. No. 2007/0141628), and polystyrene (U.S. Pat. App. Pub. No. 2007/0261775).

The target surface-binding peptide may have strong affinity for a particulate benefit agent surface (such as a pigment, a sunscreen agent, a whitening agent, etc.), a polymeric coating applied to a particulate benefit agent (such as a coated pigment), a clay, calcium carbonate or a body surface. Examples of various target-binding peptides are provided in the sequence listing.

Production of Fusion Peptides Comprising an Inclusion Body Tag

The peptide of interest may be a small peptide that is appreciably soluble in the host cell and/or subject to endogenous proteolytic degradation. As such, the peptide of interest may be produced in an insoluble form (such as inclusion bodies) by fusing the peptide of interest to an inclusion body tag (see U.S. patent application Ser. Nos. 11/782,836, 11/641,273, 11/641,936, 12/172,395, 11/641,981, and U.S. Pat. No. 7,427,656; each incorporated herein by reference).

The desired gene product may be a small bioactive peptide of interest that is appreciably soluble in the host cell and/or host cell liquid lysate under normal physiological conditions. Fusion of the peptide of interest to at least one inclusion body forming tags creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using centrifugation or filtration.

Typically, the fusion peptide is insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix can be adjusted to obtain the desired solubility characteristics of the fusion peptide/inclusion body.

The peptide of interest may be expressed as a fusion peptide having the following general structure:

IBT-CL-POI

Or

POI-CL-IBT wherein;
IBT means at least one inclusion body tag;
CL means at least one cleavable peptide linker; and
POI means at least one peptide of interest.

As shown in the Examples, knockout mutations to several endogenous genes in *E. coli* increased the production of the heterologous fusion peptides. The model fusion peptides were comprised of an inclusion body tag coupled to a peptide of interest (HC776124 or HC415) via an acid labile aspartic acid-proline dipeptide (see U.S. patent application Ser. No. 11/782,836).

Cleavable Peptide Linkers

The use of cleavable peptide linkers is well known in the art. Fusion peptides comprising at least one inclusion body tag will typically include at least one cleavable sequence separating the inclusion body tag from the peptide of interest. The cleavable sequence facilitates separation of the inclusion body tag(s) from the peptide(s) of interest. The cleavable sequence may be provided by a portion of the inclusion body tag and/or the peptide of interest (e.g., inclusion of an acid cleavable aspartic acid-proline moiety). The cleavable sequence preferably includes in the fusion peptide at least one cleavable peptide linker between the inclusion body tag and the peptide of interest.

Means to cleave the peptide linkers are well known in the art and may include chemical hydrolysis, enzymatic cleavage agents, and combinations thereof. One or more chemically cleavable peptide linkers are included in the fusion construct to facilitate recovery of the peptide of interest from the inclusion body fusion protein. Examples of chemical cleavage reagents include cyanogen bromide, which cleaves methionine residues; N-chloro succinimide, iodobenzoic acid or BNPS-skatole [2-(2-nitrophenylsulfenyl)-3-methylindole], which cleaves tryptophan residues; dilute acids, which cleave at aspartyl-prolyl bonds, One or more aspartic acid-proline acid cleavable recognition sites (i.e., a cleavable peptide linker comprising one or more D-P dipeptide moieties) may preferably be included in the fusion protein construct to facilitate separation of the inclusion body tag(s) form the peptide of interest. The fusion peptide may include multiple regions encoding peptides of interest separated by one or more cleavable peptide linkers.

Moreover, one or more enzymatic cleavage sequences may be included in the fusion protein construct to facilitate recovery of the peptide of interest. Proteolytic enzymes and their respective cleavage site specificities are well known in the art. Preferably, the proteolytic enzyme is selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra).

Typically, cleavage occurs after the insoluble inclusion bodies and/or insoluble fusion peptides are isolated from the cell lysate. Methods of lysing cells and isolation peptide from the cell lysate are well known in the art. Once isolated, the insoluble inclusion bodies and/or fusion peptides can be treated with a or enzymatic cleavage agent to cleave the inclusion body tag from the peptide of interest. After cleavage step, preferably, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. The peptide of interest may be soluble or insoluble while the inclusion body tag and/or fusion protein is insoluble or soluble in the defined process matrix, typically aqueous. Optionally, the peptide of interest may be further purified using any number of well known purification techniques in the art such as ion exchange, gel purification techniques, and column chromatography (see U.S. Pat. No. 5,648,244).

Peptide-Based Reagents for Delivery of a Benefit Agent to a Body Surface

The methods described herein may produce peptide-based reagents comprising a first portion having affinity for a body surface and a second portion capable of being coupled to a benefit agent. The peptide-based reagent may a first binding domain (binding "hand") having multiple body surface-binding peptides ("fingers") and a second binding domain ("hand") having affinity for the benefit agent. The second binding domain may comprise multiple benefit agent-binding peptides. The benefit agent may be a peptide of interest itself or may be one or more molecules bound to, covalently or non-covalently, or associated with, the peptide of interest wherein the binding affinity of the peptide of interest is used to selectively target the benefit agent to the targeted material. The benefit agent may be a particulate benefit agent, such as a pigment or coated pigment.

The peptide of interest may comprise at least one region having an affinity for a targeted material and a plurality of regions having an affinity for a variety of benefit agents wherein the benefit agents may be the same or different. Examples of benefits agents include, but are not limited to, conditioners for personal care products, pigments, dye, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides; see SEQ ID NOs: 442-470).

Host Cells

Transcription, translation, and the protein biosynthetic apparatus are universal genetic processes. Examples of microbial production hosts may include, but are not limited to bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus,*

*Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*.

In one embodiment, the host strain is a member of the genus *Escherichia*. The host strain may be *Escherichia coli*. In another embodiment, the host cell is derived from an *Escherichia coli* K-12 strain or an *Escherichia coli* B strain. In a further embodiment, the *Escherichia coli* host strain is preferably derived from a K-12 strain, such as *E. coli* K-12 substrain MG1655 (ATCC® 47076™).

Fermentation Media

Fermentation media must contain suitable carbon substrates. Suitable substrates may include, but are not limited to, monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. L-arabinose is used to induce the present arabinose inducible expression system. As such, L-arabinose is typically not included in the fermentation media until expression of the desired chimeric gene (encoding the peptide or protein of interest) is desired. L-arabinose can be added at any time during the fermentation, although it is often preferable to induce expression only after a desired cell density/mass is achieved in the fermentor. It is contemplated that the source of carbon utilized in the present invention may encompass a wide variety of carbon containing substrates and will only be limited by the choice of organism. Preferred carbon substrates include glucose, fructose, and sucrose.

In addition to a carbon source, fermentation media may or must contain other components suitable and/or necessary for the growth of the cultures and promotion of the expression of the present fusion peptides. These are known to those skilled in the art and include minerals, salts, cofactors, buffers, etc.

Culture Conditions

Suitable growth conditions can vary and depend on the chosen production host and are generally known in the art. Typically, cells are grown at a temperature in the range of about 25° C. to about 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred. Fermentation may be performed under either aerobic or anaerobic conditions whereas aerobic conditions are generally preferred.

Industrial Batch and Continuous Fermentations

Classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol*., (1992) 36:227-234.

Although typically performed in batch mode, it is contemplated that the methods described herein would be adaptable to continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

The methods described herein may be practiced using either batch, fed-batch or continuous processes and that any known mode of fermentation would be suitable.

EXAMPLES

The Examples further describe by illustration only the cells and methods described above. From the above discussion and these Examples, one skilled in the art can ascertain the essential characteristics of the inventions recited in the claims. One of skill in the art will recognize that typically any amount, concentration, or other value or parameter that is given either as a range, preferred range, or a list of upper preferable values and lower preferable values, is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "µm" means micrometer(s), "µM" means micromolar, "mM" means millimolar, "M" means molar, "mmol" means millimole(s), "µmol" means micromole(s), "pmol" means picomole(s), "g" means gram(s), "µg" means microgram(s), "mg" means milligram(s), "g" means the gravitation constant, "rpm" means revolutions per minute, and "cat#" means catalog number, "PN" means part number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

Peptide Expression Systems

The peptide expression system used in the present examples is based on *Escherichia coli* MG1655 (ATCC® 47076™)-derived strain QC1100 in combination with a pBAD-based expression vector. The modified *E. coli* MG1655 strain comprising a disruption in the endogenous araBAD operon is referred to herein as *E. coli* strain KK2000 (the nucleic acid sequence of an araB promoter is provided as SEQ ID NO: 20). A knockout of slyD (SEQ ID NOs: 21 and 22) was engineered into KK2000 to reduce background of LUMIO™-based in-cell labeling. KK2000 containing the slyD knockout is referred to herein as *E. coli* strain QC1100.

The peptides were expressed as fusions which were designed to include at least one region encoding an inclusion body tag (IBT) linked to a peptide of interest (POI). Appropriate restriction sites were included in the expression system to facilitate simple swapping of the DNA encoding the inclusion body tag and/or peptide of interest. The fusion peptide was designed to have a cleavable peptide linker (for example, an acid cleavable aspartic acid-protein moiety (DP)) between the inclusion body tag (IBT) and the peptide of interest (POI). Furthermore, the fusion peptide was also designed to include at least one tetracysteine tag (LUMIO™ tag; SEQ ID NO: 1) located on the C-terminus of the inclusion body tag wherein the tetracysteine tag was separated from the portion encoding the peptide of interest by the cleavable peptide linker. The tetracysteine tag binds the FlAsH-EDT$_2$ reagent to provide in-cell LUMIO™ labeling.

The LUMIO™ protein detection system (Invitrogen Life Technologies, Carlsbad, Calif.) is based on the incorporation of a small tetracysteine tag (TC) that covalently binds to a biarsenical labeling reagent (e.g. FlAsH-EDT$_2$ [LUMIO™ green]; ReAsh-EDT$_2$ [LUMIO™ red]); and CHoXAsh-EDT$_2$ (U.S. Pat. No. 5,932,474; U.S. Pat. No. 6,054,271; U.S. Pat. No. 6,831,160; U.S. Pat. No. 6,008,378; U.S. Pat. No. 6,451,564; U.S. Pat. No. 6,686,458; U.S. Pat. No. 7,138,503; EP1032837, EP1684073, U.S. Pat. App. Pub. No. 20050176065 A1; and Griffin et al., *Science* 281:269-271 (1998)). Covalent binding of the labeling reagent to the tetracysteine tag generates a highly fluorescent complex.

The peptide expression plasmid pLR199 (SEQ ID NO: 2) contains a ColE1 type origin of replication, the bla gene to confer ampicillin resistance and the aadA-1 gene to confer spectinomycin (Spec) resistance (see co-pending U.S. patent application Ser. No. 12/1263,608 to Cheng et al., incorporated herein by reference). The tag/peptide fusion construct was driven by the pBAD promoter. The plasmid also encodes the gene for the araC regulator. The fusion peptide construct in pLR199 contains a small inclusion body tag IBT139 (SEQ ID NO: 3) and the tetracysteine tag CCPGCC (SEQ ID NO: 1) followed by a peptide of interest (such as peptide HC776124; SEQ ID NO: 4), creating fusion peptide IBT139-CCPGCC-HC776124 (SEQ ID NOs: 5 and 6). The QC1100 strain containing the pLR199 vector was referred to as *E. coli* strain QC1101.

Expression plasmid pLR538 (SEQ ID NO: 471) has a similar vector backbone to that of pLR199 except that is expresses a different fusion peptide. Plasmid pLR538 expresses a fusion peptide comprising inclusion body tag IBT139(5C) (SEQ ID NO: 8) followed by peptide of interest HC415 (SEQ ID NO: 12), resulting in the construct pLR538 expressing the fusion peptide IBT139(5C)-HC415 (SEQ ID NO: 472 [the nucleic acid sequence] and SEQ ID NO: 473 [the corresponding amino acid sequence]).

Expression plasmid pDCQ523 (SEQ ID NO: 7) has a similar vector backbone to that of pLR199 except that it expresses a different fusion peptide. Plasmid pDCQ523 expresses the fusion peptide consisted of the small inclusion body tag IBT139(5C) (SEQ ID NO: 8), the tetracysteine tag CCPGCC (SEQ ID NO: 1), followed by peptide of interest HC415. The nucleic acid sequence encoding the resulting fusion peptide IBT139(5C)-CCPGCC-HC415 is provided as SEQ ID NO: 9 and the corresponding amino acid sequence is provided as SEQ ID NO: 10. The nucleic acid sequence for HC415 is provided as SEQ ID NO: 11 and the corresponding amino acid sequence is provided as SEQ ID NO: 12.

FACS System Operating Conditions:

A Fluorescence Activated Cell Sorter (FACSVANTAGE™ SE-DiVa; Becton-Dickinson (BD Biosciences, Franklin Lakes, N.J.)) was configured with a single 488 nm argon ion laser (200 mW). The laser is used to induce light scattering by either the excitation of cellular fluorescent tags or the granularity within the cell. The SSC (Side Scatter Collector) light detection from the cell is collected through a microscope objective, transmitted via fiber light guide to an array of photo-multiplier tubes (PMTs). The FSC (Forward Scatter Collector) was constructed of a photo-diode. The SSC octagon configuration was composed of 5 PMTs in an octagon configuration. The LUMIO™ collection at 530 nm used a fluorescein isothiocyanate (FITC) filter (530 nm center, +/−15 nm bands) with a SSC filter of 488 nm bandpass (488 nm center, +/−10 nm bands). The system fluid used on the FACSVANTAGE™ SE-DiVa was FACSFLOW™ Sheath (Becton Dickinson) at an operating pressure of 28 psi (~193 kPa) using a 70 μm diameter orifice tip.

The standard daily alignment of the instrument was performed using ALIGNFLOW™ (Molecular Probes, Inc., Eugene, Oreg.) 2.5 μm diameter fluorescent beads at an excitation/emission of 488 nm. The ALIGNFLOW™ beads were used as the daily alignment standard and the following instrument adjustments were made on the FACS to obtain the maximum PMT signal and minimum CV (coefficient of variation) for all channels on the instrument. The ALIGNFLOW™ beads were used to enable the daily adjustment of the FACS nozzle (X, Y, Z, α, and θ); in addition to the focus lens, channel height and channel height focus in all detector channels. The alignment of the FACS system can vary, but with the use of the ALIGNFLOW™ beads good alignment reproducibility was obtained. The ALIGNFLOW™ beads were either incorporated as a separate sample or directly into the sample to monitor the alignment and any potential instrument drift. The daily FACS alignment procedure, created in the DiVa Software (Becton Dickinson, v1.4), was performed and verified to within normal operating conditions.

The LUMIO™-stained cell samples were previously prepared in PBS (phosphate buffered saline) which is similar to the sheath fluid; therefore, no additional manipulation was needed for FACS analysis. Approximately 200 μL of a sample containing LUMIO™ stained cells was placed into a Falcon 12×75 mm, sterile polystyrene culture tube (Becton Dickinson) and into the instrument. The sample differential pressure was adjusted to obtain a stable 1000 events/second; at which, between 20,000 and 50,000 sample events were recorded. The variation, in sample recorded events, was due to the variation in cell concentration and limited sample volume. If the number of observed events was low, then the recorded events were then decreased. The samples scanned on the FACS for LUMIO™ analysis included, but were not limited to, an ALIGNFLOW™ bead sample, unstained LUMIO™ (negative control) and a series of LUMIO™ stained samples (experimental). The data obtained for the FACS samples included several different plot windows; which included dot plots for FSC-A vs SSC-A, FSC-A vs. FITC-A, SSC-A vs FITC-A and histograms for SSC-A, FSC-A, and FITC-A (width×height) for the particular channel ("A" is the computed area; "FS" is forward scatter; and "SS" is side scatter). During the recording of each sample, a gate was set on the FITC-A histogram between the $10^3$ and $10^4$ (log scale) to monitor and observe the sample LUMIO™ labeling efficiency. The recorded events within the gate on the FITC-A log scale provided a good indication of the sample LUMIO™ labeling efficiency. The recorded LUMIO™ sample data was saved and then within the DiVA software they were exported as FCS3 data files for further analysis.

Compositions of Growth Media and Buffers

TABLE 1

Media and Buffers

| Media/Buffer | Ingredient | Amount |
|---|---|---|
| Miller LB | Casein protein | 10 g/L |
| | NaCl | 10 g/L |
| | Yeast extract | 5 g/L |
| Dubelco's 1X PBS | KCl | 0.2 g/L |
| | $KH_2PO_4$ | 0.2 g/L |
| | NaCl | 8 g/L |
| | $Na_2HPO_4*7H_2O$ | 2.16 g/L |
| DEK Media | $KH_2PO_4$ | 9 g/L |
| | $(NH_4)_2HPO_4$ | 4 g/L |
| | Citric acid*$H_2O$ | 1.86 g/L |
| | Yeast extract | 5 g/L |
| | Biospumex 153K | 0.1 mL/L |
| | (Post sterilization) | |
| | $MgSO_4*7H_2O$ | 1.2 g/L |
| | Thiamine HCl | 4.5 mg/L |
| | Trace elements | 10 mL/L |
| | (batch - see below) | |
| | Uracil | 50 mg/L |
| Trace elements | EDTA | 840 mg/L |
| | $CoCl_2*6H_2O$ | 250 mg/L |
| | $MnCl_2*4H_2O$ | 1500 mg/L |
| | $CuCl_2*2H_2O$ | 150 mg/L |
| | $H_3BO_3$ | 300 mg/L |
| | $Na_2MoO_4*2H_2O$ | 250 mg/L |
| | $Zn(CH_3COO)_2*2H_2O$ | 1300 mg/L |
| | Fe(III) Citrate | 10000 mg/L |

Example 1

Construction and Sorting of a Transposon Insertion Library

This example describes construction of a transposon insertion library in a peptide production strain QC1101, which produced fusion peptide that contained the tetracysteine tag (CCPGCC; SEQ ID NO: 1). The tetracysteine tag allowed specific labeling of the fusion peptide by fluorescein derivative of biarsenical ligands FlAsH-EDT$_2$ (LUMIO™ Green), and sorting of the library by fluorescence on FACS. The LUMIO™ reagents were obtained from Invitrogen (Carlsbad, Calif.).

The transposon insertion library was constructed in a peptide production strain QC1101, which expressed the fusion peptide consisted of the small inclusion body tag IBT139 (SEQ ID NO: 3), the tetracysteine tag (SEQ ID NO: 1) followed by the peptide of interest HC776124 (SEQ ID NO: 4). The Tn5-KAN transposome from Epicentre Technologies (Madison, Wis.) was used for the transposon mutagenesis with QC1101 strain following manufacturer's instruction. Approximately 38,000 transposon mutants were obtained and pooled. This transposon insertion library was designated as QC1150 library.

The QC1150 library cells were labeled using TC-FlAsH™ In-Cell tetracysteine tag detection kit (Invitrogen). The library cells were thawed from frozen stocks and grew for about 3 hours in 20 mL of DEK medium containing 0.4% glycerol with ampicillin (100 μg/mL) and kanamycin (25 μg/mL) till an OD$_{600}$ of about 1.5. The cells were then induced with 0.2% L-arabinose for about 3 hours. The induced cells were diluted and normalized to an OD$_{600}$ of about 1. Approximately 3×10$^7$ cells were then labeled with 20 μM FlAsH-EDT$_2$ reagent for 1.5 hours at room temperature (~22° C.) in the dark. The labeled cells were washed twice with BAL wash buffer and resuspended in PBS for sorting on FACS based on fluorescence. The gate for the first sort was set for the top 10% of fluorescent cells. About 100,000 events were collected and plated on LB plates with ampicillin (100 μg/mL) and kanamycin (25 μg/mL). The plates were incubated at 37° C. overnight. The colonies grew on the plates were pooled and aliquotes were used to grow cells for the next round of labeling following the same protocol as described above. The parameters used for each round of sorting is provided in Table 2. A total of four rounds of sorting was performed and aliquotes from each round were also frozen. About 200 colonies obtained from the fourth round of sorting was picked into microtiter plates for sequencing.

TABLE 2

Parameter used for sorting Library QC1150

| Round No. | Number of Events | Percent Sort of Previous Round (%) |
|---|---|---|
| QC1150[a] Library | NA | NA |
| 1 | 100,000 | 10% |
| 2 | 50,000 | 5% |
| 3 | 50,000 | 1% |
| 4 | 10,000 | 0.5% |

[a] = Library QC1150 titer >38,000.

Example 2

Sequencing of the Sorted Clones

The transposon insertion site in each of the mutant was mapped by genomic sequencing using the ILLUSTRA™ GENOMIPHI™ v2 DNA Amplification kit from GE Healthcare (Piscataway, N.J.). The primers to sequence the chromosomal junction of both ends of the transposon were:

```
Kan2cb-For
(5'-CTGGTCCACCTACAACAAAGCTCTCATC-3';
SEQ ID NO: 13)
and kan2cb-Rev
(5'-CTTGTGCAATGTAACATCAGAGATTTTGAGACACAC-3';
SEQ ID NO: 14).
```

The mutants selected for further analysis are listed in Table 3.

Among the sequenced clones, the highest number of hits was in the ftsN gene. Nine different ftsN mutants were obtained with the transposon inserted at different locations of the ftsN gene in different orientations. The ftsN gene was reported to be involved in cell division (Yang, J. C., et al. (2004), *Mol. Micro.* 52:651; Goehring, N. W., et al., (2007), *J. Bacteriol.* 189:646) and the higher fluorescence of the ftsN mutants might be an artifact of sorting as a result from defective cell division. The ftsN mutant was not pursued further.

The next highest number of hits was in the gcvA gene (SEQ ID NO: 15). Seven different gcvA mutants were isolated with the transposon inserted at different locations of the gcvA gene in the same orientation as the gcvA gene. The gcvA gene encodes a regulatory protein (GcvA; SEQ ID NO: 16) for glycine cleavage pathway (Wilson, R. L., and Stauffer, G. V., (1994), *J. Bacteriol.* 176:2862-2828). Two related mutants of the glycine cleavage system were also isolated containing transposon insertions in the gcvP gene. The gcvP gene encodes glycine decarboxylase, the largest catalytic protein (P-protein) in the glycine cleavage enzyme complex (Stauffer, L. T., et al., (1994), *Gene* 142:17-22). The glycine cleavage (GCV) enzyme system catalyzes the oxidative cleavage of glycine into $CO_2$ and $NH_3$ and transfers the one-carbon ($C_1$) methylene unit to tetrahydrofolate. This $C_1$-containing molecule, 5,10-methylenetetrahydrofolate, can then be used as the $C_1$ donor in the biosynthesis of purines, methionine, thymine, and other cellular components. The GCV system was shown to represent the major pathway of catabolism of glycine and serine. The genes encoding the three catalytic proteins of the GCV system (gcvTHP) are organized in an operon, which maps at 62.5 min on the *E. coli* chromosome. The gcvA gene encoding the regulatory protein which activates the GCV system is at a separate location at 60.3 min on the *E. coli* chromosome. Two mutants containing transposon insertions in the dam gene encoding DNA adenine methylase were also selected for further analysis, since the GCV system is related to cellular methylation reactions by providing the $C_1$ donors for methylation.

Several peptidase mutants were isolated once and were further characterized. A transposon mutant contained the insertion in the pbpG gene encoding D-alanyl-D-alanine endopeptidase. A transposon mutant contained the insertion in the spr gene (SEQ ID NO: 17) encoding a predicted peptidoglycan-hydrolyzing peptidase (Spr; SEQ ID NO: 18). A transposon mutant contained the insertion in the pepE gene encoding (alpha)-aspartyl dipeptidase. A transposon mutant contained the insertion in the prlC gene encoding oligopeptidase A.

TABLE 3

Summary of the selected transposon insertion mutants in E. coli

| Mutant | No. of hits | Gene Location | Coding Strand | Gene Function | Reference | Keio Strain[1] (ID No.) |
|---|---|---|---|---|---|---|
| ftsN | 9 | 4120403-4121362 | − | Cell division | Yang, J. C., et al., (2004), Mol. Micro. 52: 651 | NA |
| gcvA | 7 | 2939672-2940589 | − | DNA-binding transcriptional dual regulator | Wilson, R L, et al., (1994), J. Bacteriol. 176: 2862 | JW2779 |
| gcvP | 2 | 3044190-3047063 | − | glycine decarboxylase, subunit (protein P) of glycine cleavage complex | Stauffer, L. T., et al., (1994), Gene 142: 17 | JW2871 |
| dam | 2 | 3513099-3513935 | − | DNA adenine methylase | Lobner-Olesen, A., et al., (2005), Curr. Opin. Microbiol. 8: 154 | JW3350 |
| pbpG | 1 | 2221960-2222892 | − | D-alanyl-D-alanine endopeptidase | Romeis, T., et al., (1994), J. Biol. Chem. 269: 21603 | JW5355 |
| spr | 1 | 2268001-2268567 | + | predicted peptidase, outer membrane lipoprotein | Hara, H., et al., (1996), Micro Drug Resist 2: 63 | JW2163 |
| pepE | 1 | 4227476-4228165 | − | (alpha)-aspartyl dipeptidase | Conlin, C. A., et al., (1994), J. Bacteriol. 176: 1552 | JW3981 |
| prlC | 1 | 3641163-3643205 | − | oligopeptidase A, periplasmic protease | Hara, H., et al., (1991), J. Bacteriol. 173: 4799 | JW3465 |

[1] = Keio strain collection. Baba, T., et al., (2006) Mo. I Syst. Biol. 2: 2006.0008 (article No.).

Example 3

Confirmation of FACS Analysis with Clean Deletion Mutants

To verify that the genes interrupted by the transposon insertions were responsible for the phenotypes, clean mutants were reconstructed that contained the in-frame deletion of the particular single genes interrupted by the transposon insertions. A collection of the E. coli K12 in-frame single gene knockout mutants was used ("Keio collection"; Baba, T., et al., supra). The particular Keio knockout strains that corresponding to the transposon insertion mutants (see Table 3) were streaked out from the collection on LB containing kanamycin (25 µg/mL) plates. P1 lysates were prepared by growing P1clr100 Cm phage with the individual Keio strains (Miller, J. H., (1972), Experiments in Molecular Genetics. Cold Spring Harbor Laboratory, Cold Spring Harbor, N.Y.). The phage lysates were then used to transduce the control strain QC1100. Mutants that contained the gene knockouts of interest were selected on kanamycin plates and confirmed by PCR. The kanamycin marker flanked by the FRT sites was removed by transient expression of the FLP plasmid pCP20 (Datsenko and Wanner, (2000) PNAS, 97:6640-6645). This resulted in strains QC1503, QC1504, QC1505, QC1506, QC1507, QC1508 and QC1509 containing the in-frame deletion of gcvA (SEQ ID NO: 15), pbpG, spr (SEQ ID NO: 17), pepE, gcvP, pr/C or dam gene, respectively.

The peptide production plasmid pLR199 was transformed into the clean deletion strains. These strains were grown, induced and labeled for FACS analysis. Each strain was grown in 3 mL DEK containing 0.4% glycerol with ampicillin (100 µg/mL) and kanamycin (25 µg/mL) till an $OD_{600}$ of about 1.5. The cells were then induced with 0.2% L-arabinose for about 3 hours. The induced cells were labeled with 20 µM FlAsH-$EDT_2$ reagent for 1.5 hours at room temperature (~22° C.) in the dark. The labeled cells were washed twice with BAL wash buffer and resuspended in PBS. FACS analysis of these strains was shown in Table 4. The values were normalized and shown as the percentage to the respective values of the control strain QC1101. Among the seven strains, three showed higher fluorescence than the control. The spr mutant showed more than 300% higher fluorescence, the gcvA mutant showed about 150% higher fluorescence, and the gcvP mutant showed less than 110% higher fluorescence than the control.

TABLE 4

FACS Analysis of Various E. coli Strains with In-Frame Deletions

| Strain | FSC % relative to control QC1101 | SSC % relative to control QC1101 | FITC % relative to control QC1101 |
|---|---|---|---|
| QC1101 (control) | 100 | 100 | 100 |
| QC1503 (ΔgcvA) | 176.6 | 118.2 | 148.8 |
| QC1504 (ΔpbpG) | 98.0 | 94.6 | 68.2 |
| QC1505 (Δspr) | 356.4 | 161.0 | 332.3 |
| QC1506 (ΔpepE) | 99.5 | 91.3 | 83.3 |
| QC1507 (ΔgcvP) | 122.5 | 106.5 | 105.6 |
| QC1508 (ΔprlC) | 96.6 | 98.2 | 76.1 |
| QC1509 (Δdam) | 104.7 | 118.4 | 78.3 |

A double mutant that contained deletion of both spr and gcvA genes was constructed by P1 transduction as described above using P1 lysate from the spr strain JW2163 to transduce QC1503 containing the gcvA deletion. QC1510 strain containing deletion of both spr and gcvA genes was confirmed by PCR. Peptide production plasmid pLR199 was then transformed into QC1510 (ΔgcvA Δspr) resulting QC1513. QC1503 (ΔgcvA) and QC1505 (Δspr) containing the pLR199 plasmid were designated as strains QC1511 and QC1512. Triplicate cultures of strains QC1511, QC1512, QC1513 and the control strain, QC1101, were grown and induced as described above. The cultures were normalized to an $OD_{600}$ of 1 by dilution. Aliquots of the normalized cultures were used for in-cell labeling for FACS analysis (Example 3), for in-gel labeling for peptide quantitation (see Example 4), and for plate counts (see Example 5). The FACS analysis results are shown in Table 5. The forward scattering (FSC), side scattering (SSC) and fluorescence intensity (FITC) data are shown in three separate columns comparing uninduced vs. induced measurements. The standard deviation was calculated using 3 independent cultures. Both QC1511 and QC1512 showed higher average means of FSC, SSC and FITC than the control QC1101. The double mutant QC1513 showed even higher FSC, SSC and FITC means than either of the single mutant.

TABLE 5

FACS Analysis of In-cell Labeled Strains[2]

| Strain | Uninduced FSC-A | Induced FSC-A | Uninduced SSC-A | Induced SSC-A | Uninduced FITC-A | Induced FITC-A |
|---|---|---|---|---|---|---|
| QC1101 (control) | 2836 | 3399 ± 97.6 | 1711 | 1965 ± 82.9 | 21 | 1157 ± 59.4 |
| QC1511 (ΔgcvA) | 3823 | 6791.7 ± 434.3 | 1664 | 2555.7 ± 159.8 | 24 | 3727.7 ± 163.7 |
| QC1512 (Δspr) | 8471 | 14692 ± 162.5 | 3051 | 3586.7 ± 78.1 | 134 | 3283 ± 171.1 |
| QC1513 (ΔgcvA Δspr) | 9147 | 17827 ± 726.0 | 4602 | 8016.7 ± 293.2 | 144 | 5535 ± 198.5 |

[2] = All values reported in relative units (RU) from FACS analysis.

Example 4

Construction and Sorting of the Tn-Promoter Insertion Libraries

This example describes construction of transposon-promoter insertion libraries in a peptide production strain QC1525. Peptide production strain QC1525 was prepared by transforming strain QC1101 with peptide expression plasmid pDCQ523. Expression plasmid pDCQ523 has a similar vector backbone to that of pLR199 except that it expresses a different fusion peptide. Plasmid pDCQ523 expresses the fusion peptide consisted of the small inclusion body tag IBT139(5C) (SEQ ID NO: 8), the tetracysteine tag CCPGCC (SEQ ID NO: 1), followed by peptide of interest HC415 (SEQ ID NO: 12). The resulting strain produced fusion peptide IBT139(5C)-CCPGCC-HC415 (SEQ ID NO:10). The tetracysteine tag allowed specific labeling of the fusion peptide by fluorescein derivative of biarsenical ligands FlAsH-$EDT_2$ (LUMIO™ Green), and sorting of the library by fluorescence on FACS. The LUMIO™ reagents were obtained from Invitrogen (Carlsbad, Calif.).

The elements of HC415 are provided in Table 6. The hair binding domain of HC415 comprises hair-binding peptide "HP2" (AQSQLPDKHSGLHERAPQRY; SEQ ID NO: 105) linked to hair-binding peptide "MEA4" (HINKTNPHQGNHHSEKTQRQ; SEQ ID NO: 99) through a peptide linker (GPEEAAKKEEAAKKPA; SEQ ID NO: 19). The opposite end of HC415 has a pigment-binding domain with two copies of the iron oxide-based pigment-binding peptide Rfe5 (DSHHNHHKQDSRPQHRKTPN; SEQ ID NO: 363 separated by a polyglycine linker.

TABLE 6

Fusion Peptide Components

| Component | Amino Acid Sequence |
|---|---|
| IBT139(5C) | SEQ ID NO: 8 |
| HC415 | SEQ ID NO: 12 |
| IBT139(5C)-CCPGCC-HC415 | SEQ ID NO: 10 |

TABLE 7

Fusion peptide HC415

| Peptide ID | Formula[3] | Amino Acid Sequence |
|---|---|---|
| HC415 | DPS-HP2-<br>*GPEEAAKKEEAAKKPA*-<br>MEA4-<br>GSGGGGSGSGGGGS-<br>Rfe5-*GGG*-Rfe5-GK | DPS-AQSQLPDKHSGLHERAPQ<br>RY-GPEEAAKKEEAAKKPA-HI<br>NKTNPHQGNHHSEKTQRQ-GSG<br>GGGSGSGGGGS-DSHHNHHKQD<br>SRPQHRKTPN-GGG-DSHHNHH |

TABLE 7-continued

Fusion peptide HC415

| Peptide ID | Formula[3] | Amino Acid Sequence |
|---|---|---|
| | | KQDSRPQHRKTPN-GK (SEQ ID NO: 12) |

[3]= hair-binding and pigment-binding peptides previously identified by biopanning are in bold. The peptide linkers are italicized.

The plasmids pDCQ702 (SEQ ID NO: 474), pDCQ703 (SEQ ID NO: 475) and pDCQ704 (SEQ ID NO: 476) contained transposons Tn5 carrying the kanamycin resistance gene followed by the outwards T5 promoter, Pcat promoter or the trc* promoter with a T114C change. The Tn5-Kan-PT5 cassette (SEQ ID NO: 477), Tn5-Kan-Pcat cassette (SEQ ID NO: 478) or the Tn5-Kan-Ptrc* cassette (SEQ ID NO: 479) was amplified by PCR from the NdeI-linearized pDCQ702, pDCQ703 or pDCQ704 template DNA using the 5' phosphorylated primer Tn5ME (5'-CTGTCTCTTATACACATCT-CAA-3'; SEQ ID NO: 480). The PCR products were purified and digested with DpnI to remove the parental template. The digested reactions were cleaned up using Qiagen MinElute columns and eluted in 35 µL elution buffer with 0.5 mM EDTA. Transposome complex was formed in vitro using 1.5 µL (about 400 ng) of these prepared Tn cassettes with 4 µL of transposase (1 unit/µL, Epicentre, Madison, Wis.) and 2.5 µL of 80% glycerol. The transposome complex reaction was incubated at room temperature for 2.5 hours and stored at 4° C. for 3 days. The transposome complexes were then electroporated into competent cells of a peptide production strain QC1525 (prepared by transforming strain into QC1101 peptide production plasmid pDCQ523). Approximately 4~9×10[5] kanamycin resistant transposon insertion mutants were obtained, whereas the background control reaction with no transposase added gave only about 200~3000 colonies. The 4~9×10[5] transposon insertion mutants from each library were pooled and the mutant pools were designated as QC3000 library for the random Tn5-Pcat insertions, QC3200 library for the random Tn5-PT5 insertions and QC3300 library for the random Tn5-Ptrc* insertions, respectively.

The QC3000, QC3200 and QC3300 library cells were labeled using TC-FlAsH™ In-Cell tetracysteine tag detection kit (Invitrogen) and sorted by FACS as described above. The labeling and sorting procedure was similar to what was described in Example 1 except that a top 0.1% fluorecence was used as the final gate for the fourth round of sorting. About 300 colonies obtained from the last sorting were picked into microtiter plates for Genomiphi sequencing as described in Example 2 using primer HindIII-out (5'-gcttgc-caacgactacgcac-3' (SEQ ID NO: 481).

Example 5

Identification and Reconstruction of yejM Insertions

Among the sequenced mutants, about 1% of QC3000 insertions, 14% of QC3200 insertions and 47% QC3300 insertions mapped to the yejM gene. The yejM gene (the coding region provided as SEQ ID NO: 482) has 1761 nucleotides and encodes a 586 amino acid protein (SEQ ID NO: 483). YejM protein was reported to be an essential protein with unknown function. Membrane topology prediction indicated that yejM is an inner membrane protein that contains five putative transmembrane helices at N terminal part and a C-terminal periplasmic domain (Rapp, M., et al, *Protein Sci.* (2004) 13:937-945; Daley et al, *Science* (2005) 308:1321-1323). The periplasmic domain of YejM has sequence homology to sulfatases/phosphatases in the Swiss-Prot database. The yejM null mutation is lethal (De Lay, N R, and Cronan, J E, *Genetics* (2008) 178:1327-1337). A mutant LH530 with G570A mutation, which retained its N terminal domain (190 amino acids) but lacking its C terminal domain, was temperature sensitive. The transposon insertions we isolated mapped at nucleotides ranging from 723 to 1706, which corresponding to 241 to 568 amino acid residues retained for the YejM protein. None of the insertion mutant we isolated appeared to be temperature sensitive. FACS analysis of several isolates containing the original yejM insertions was performed as described in Example 3 and showed that they had 150-200% of FSC, 110-120% of SSC and 600-1000% of FITC comparing to the control.

Figure 2:
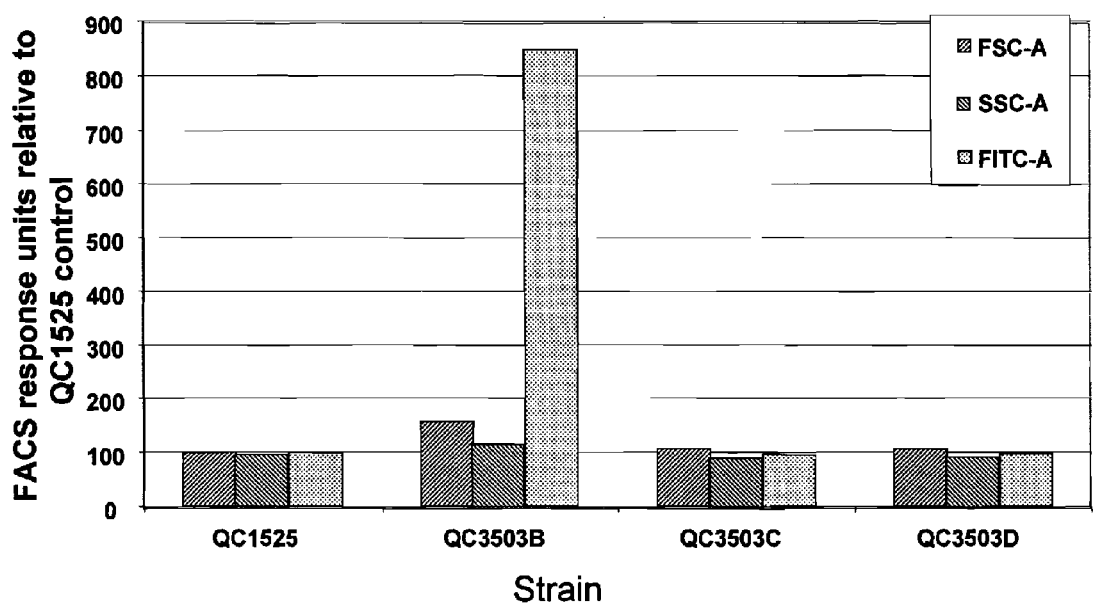
FIG. 2. FACS analysis of the mutants comparing to the QC1525 control. The striped columns represent the forward scattering data (FSC-A); the gridded columns represent the side scattering data (SSC-A); the dotted columns represent the fluorescence data (FITC-A).

To distinguish if the phenotype was due to truncation of yejM or was due to overexpression of the downstream proL gene encoding a proline-tRNA gene, Tn5-Kan-Pcat gene cassette was inserted in the middle of the yejM gene (QC3503B), after the stop codon of the yejM gene (QC3503C) or downstream of the proL gene (QC3503D) by Lambda Red recombination (FIG. 1, QC1100 containing pRed/ET (Gene Bridges GmbH, Germany; U.S. Pat. Nos. 6,355,412 and 6,509,156) was used as the parent. The primers yejM-catF: 5'-acaatacggtggtgattatcactgccg-gtcggggtattccgtgcgtagtcgttggcaagc-3' (SEQ ID NO: 484) and yejM-catR: 5'-accgtgggaccagtcaaaggtttcttc-ctcttcgctcagttttagcttccttagctcctg-3' (SEQ ID NO: 485) were used to create the QC3503B. The primers proL-catF: 5'-agt-gctgacagacgagaagcgttt-tatcgctaactgattagtgcgtagtcgttggcaagc-3' (SEQ ID NO: 486) and proL-catR: 5'-accgattgcaagtaa-gatatttcgctaactgatttataattttagcttccttagctcctg-3' (SEQ ID NO: 487) were used to create the QC3503C. The primers proLdown-catF: 5'-ttaattcgataaacagaccgtgacacatcacagcctgttt gtgcgtagtcgttggcaagc-3' (SEQ ID NO: 488) and proLdown-catR:-5'-ctcaggcgggtgtggtctggacgttctgataacagaaaat tttagcttc-cttagctcctg-3' (SEQ ID NO: 489) were used to create the QC3503D. The Tn cassette from pDCQ703 was used as the template. The procedure for Lambda Red recombination was followed according to the protocol from Gene Bridges. After the insertions were confirmed, the kanamycin resistant gene was removed by Cre-mediated recombination of the loxP sites flanking the kanamycin resistance gene using pCre plasmid 706-Cre from Gene Bridges. Peptide expression plasmid pDCQ523 expressing IBT139 (5C)-CCPGCC-HC415 was transformed into the above hosts. FACS analysis of these cells and the QC1525 control cells were shown in FIG. 2. The FACS data observed with the original isolates were confirmed by the reconstructed insertion in the yejM gene in the fresh host. It is clear that the increased fluorescence was only observed with the insertion that disrupted the yejM gene. Expression of the downstream proL gene with the same promoter from the Tn5 end did not show any apparent phenotype.

Example 6

Stacking of the yejM Mutation into the gcvA spr Double Deletion Mutant

To confirm that the increased fluorescence was due to YejM truncation and not a promoter insertion, C terminal in-frame deletions of YejM were created at two positions in the yejM coding region gene. QC3503F contained in frame deletion of C terminal 132 amino acid residues, which was targeted to the same insertion site as in QC3503B. QC3503E contained in frame deletion of C terminal 324 amino acid residues. Both deletions were created by Lambda Red recombination in QC1100 strain using the Tn cassette from pDCQ703 as the template. Primers yejM1362-loxKan5': 5'-caatacggtggtgat-tatcactgccggtcggggtattccatgagtgcgtagtcgttggcaagc-3' (SEQ ID NO: 490) and yejMdown-loxKan3'A: 5'-gattgcaagtaa-gatatttcgctaactgatttataattaatcaggccggccataacttcg-3' (SEQ ID NO: 491) were used for the 132 residue deletion, and primers yejM786-loxKan5': 5'-cgaactgcgctatcgcgatatgggcac-cgggcagaatgtgtgagtgcgtagtcgttggcaagc-3' (SEQ ID NO: 492) and yejMdown-loxKan3'A (SEQ ID NO: 491) were used for the 324 residue deletion. The kanamycin resistance gene was removed by Cre-mediated recombination of the lox sites flanking the kanamycin resistance gene using pCre plasmid 706-Cre from Gene Bridges. The remaining lox site was after the stop codon of the truncated yejM gene. The in frame deletions were confirmed by sequencing of the chromosomal junction. The same two deletions were also created in the host containing double deletions of gcvA and spr genes. The resulted QC3503G and QC3503H strains contained yejM truncations combined with gcvA and spr deletions. Peptide expression plasmid pDCQ523 expressing IBT139 (5C)-CCPGCC-HC415 was transformed into the above hosts. FACS analysis of these cells with the QC1525 control cells and the QC1527 cells (ΔgcvA Δspr) were shown in Table 8. The in frame deletions of YejM (QC3503E and QC3503F) exhibited similar phenotype as the yejM insertion by Tn5-Pcat. This confirmed that the observed 7-8 fold higher fluorescence was due to C terminal truncation of yejM gene and not due to expression of inserted promoter. The in frame deletions of YejM in the ΔgcvA Δspr background showed an increased effect. QC1527 (ΔgcvA Δspr) showed 3-fold higher fluorescence than the control. The QC3503H and QC3503G showed additional 5-7 fold further increase from the QC1527 background. These strains also showed about 4-fold higher of FSC and 2-fold higher of SSC comparing to the control.

TABLE 8

FACS analysis of the reconstructed yejM mutations

| Strains | FSC-A | Relative FSC-A | SSC-A | Relative SSC-A | FITC-A | Relative FITC-A |
|---|---|---|---|---|---|---|
| QC1525 | 2499 | 100 | 1968 | 100 | 151 | 100 |
| QC3503B (yejM::Tn5) | 3494 | 139.8 | 2428 | 123.4 | 1101 | 729.1 |
| QC3503E (ΔyejM324) | 4197 | 167.9 | 2650 | 134.7 | 1283 | 849.7 |
| QC3503F (ΔyejM132) | 4124 | 165.0 | 2481 | 126.1 | 1279 | 847.0 |
| QC1527 (ΔgcvA Δspr) | 6504 | 260.3 | 2717 | 138.1 | 456 | 302.0 |
| QC3503G (ΔgcvA Δspr ΔyejM324) | 10920 | 437.0 | 4439 | 225.6 | 3251 | 2153.0 |
| QC3503H (ΔgcvA Δspr ΔyejM132) | 9407 | 376.4 | 3677 | 186.8 | 2403 | 1591.4 |

Example 7

Peptide Quantitation Using the Same Number Events Collected from FACS

To determine if high fluorescence intensity (FITC) from FACS analysis for the mutants correlated with high peptide content per cell, peptide in-gel quantitation (normalized by same number of cells for each sample) was performed. Cells of QC1525, QC3503E (ΔyejM324), QC1527 (ΔgcvA Δspr) and QC3503G (ΔgcvA Δspr ΔyejM324) were grown and induced as described above. Two million events from the entire field of each sample (no set gate) were collected by FACS. After the FACS initial alignment (as described in the general methods), a sample of ALIGNFLOW™ 488 beads (Invitrogen; 2.5 μm, Catalog# A-7302) was used to adjust the PMT's (FSC, SSC and FITC) by placing the peaks for each channel at the same position within the channel histogram. This enabled consistent run-to-run PMT/sample adjustments. Typically, the bead peaks within the histograms were set as follows: FSC=40K, SSC=40K and FITC=20K.

The FACS settings for the collecting the 2 million events were as follows:

Instrument Configuration:

System Pressure=34 psi (~234.42 kPa)

Tip Orifice=70 μm

Frequency=62.2 KHz

Amplitude=10.6

Phase=125

DropDelay=27.48

Argon Ion Laser Power=200 mW

Sort rates were maintained between 2500 to 3000 events per second. The cells were collected into 15-mL conical tubes and were centrifuged at 9800×g for 20 min at 4° C. The supernatants were removed until about 1-mL liquid was left in the tubes. The pelleted cells were then resuspended in the 1-mL liquid and transferred to 1.7-mL microfuge tubes. The residue cells in the conical tubes were washed with 0.5 mL of PBS and combined to the microfuge tubes. The microfuge tubes were then centrifuged at 15,000×g for 5 min. The supernatants were carefully removed without disturbing the cell pellets. The cell pellets were stored at −80° C. for in-gel analysis.

The pellets were thawed and resuspended in 10-μL of B-PER® lysis (Pierce) buffer and vortex for 1 min to lyse the cells. The cells were labeled using the LUMIO™ Green detection kit (Invitrogen) following manufacture's instructions. LUMIO™ sample buffer (10 μL) was added to the 10 μL lysed cells and 0.2 μL of LUMIO™ reagent was added to each sample. The samples were heated at 70° C. for 10 min and briefly centrifuged after cooling to room temperature. LUMIO™ gel enhancer (2 μL) was then added to each sample, which were incubated at room temperature (~22° C.) for 5 min. The entire sample in the tube was loaded onto NUPAGE® 4-12% Bis-Tris gel. After gel electrophoresis, the gel was visualized under UV light. After taking a picture, the gel was rinsed, stained with SIMPLYBLUE™ (Invitrogen) and destained with deionized water. The fluorescence intensity of the fusion peptide band was quantified using the ImageJ software.

Image analysis of the gel loaded with 2 million events from each sample showed QC3503E (ΔyejM324) and QC1527 (ΔgcvA Δspr) each had 2.2 and 2.4 fold as much of fusion peptide IBT139 (5C)-CCPGCC-HC415 comparing to the control (Table 9). QC3503G (ΔgcvA Δspr ΔyejM324) showed as much as 5-fold of fusion peptide. Combination of the ΔyejM324 with the ΔgcvA Δspr showed synergistic effect that further increased peptide content per cell.

TABLE 9

Relative Fluorescence Band Intensity for Various Strains

| Strain | Relative Fluorescence band Intensity | Standard deviation |
|---|---|---|
| QC1525 - control | 100.0 | 9.2 |
| QC3503E (ΔyejM324) | 221.2 | 31.5 |
| QC1527 (ΔgcvA Δspr) | 244.0 | 26.1 |
| QC3503G (ΔgcvA Δspr ΔyejM324) | 516.2 | 95.7 |

Example 8

Measurement of Settling Velocity of *E. coli* Cells

Since the mutant *E. coli* cells appeared larger and produced more peptide content per cell, we decided to evaluate if these cells would present any advantages in downstream processing such as cell recovery and/or homogenization. This example describes the measurement of settling velocity of the mutant and control *E. coli* cells, which could affect cell sedimentation during harvest/recovery.

*E. coli* QC1521 was the control strain containing pLR538 plasmid (SEQ ID NO: 471) expressing the IBT139(5C)-HC415 fusion peptide without the CCPGCC tag. The QC1522 strain was the ΔgcvA Δspr double mutant containing pLR538 plasmid. Strain QC3515 was the ΔyejM324 truncation strain containing pLR538 plasmid. Strain QC3516 was the combination of the ΔyejM324 with the ΔgcvA Δspr strain containing pLR538 plasmid. The cells were grown in 10 mL DEK medium containing 0.4% glycerol with ampicillin (100 μg/mL) in 125 mL flasks for about 2.5 hours till an $OD_{600}$ of about 1.5. Each culture was then split and half was induced with 0.2% L-arabinose and half was not induced. They continued to grow at 37° C. for about 16 hours and reached the final $OD_{600}$ about 16 to 28. About 0.5 mL of cells from each culture were loaded in a cuvette and analyzed in an optical centrifuge (LUMiSizer®, L.U.M. GmbH, Berlin, Germany) under the following conditions: 2000 rpm, 25° C., 200 profiles, transmission profile taken every 15 sec (Δt=15 seconds), and the total experimentation time was 3000 seconds. The median of settling velocity of each culture was calculated and shown in Table 10.

TABLE 10

Median settling velocity of *E. coli* cells.

| Sample | Median Settling Velocity (μm/s) |
|---|---|
| QC1521 (control) Uninduced | 16.3 |
| QC1521 (control) Induced | 39.2 |
| QC1522 (ΔgcvA Δspr) Uninduced | 28.5 |
| QC1522 (ΔgcvA Δspr) Induced | 38.6 |
| QC3515 (ΔyejM324) Uninduced | 15.4 |
| QC3515 (ΔyejM324) Induced | 45.2 |
| QC3516 (ΔgcvA Δspr ΔyejM324) Uninduced | 27.7 |
| QC3516 (ΔgcvA Δspr ΔyejM324) Induced | 114.7 |

The median settling velocity of the induced cells is faster than the uninduced cells for any given strain, which reflected the production of inclusion bodies inside the cells. The uninduced cells of QC1522 (ΔgcvA Δspr) and QC3516 (ΔgcvA Δspr ΔyejM324) settled slightly faster than the uninduced cells of the QC1521 control. The induced cells of QC3516 settled much faster than the induced cells of the QC1521 control. The faster settling velocity might improve cell recovery yield and/or decrease the g force required for the centrifugations and/or allow for higher throughput at a given g force.

Example 9

Evaluation of Lysis Efficiency of *E. coli* Cells

To evaluate if the larger cells would be more prone to breakage/lysis in downstream processing, we tested efficiency of lysis of concentrated cells by French Press.

Cells of QC3516 and QC1521 control were grown in 200 mL DEK medium containing 0.4% glycerol with ampicillin (100 μg/mL) in 1-L flasks till $OD_{600}$ of about 2.0. Each culture was induced with 0.2% L-arabinose and continued to grow at 37° C. for about 12 hours. The final $OD_{600}$ of cells were about 10-12. To mimic the high cell density resulted from fermentations, the shake flask grown cells were concentrated and normalized to $OD_{600}$ about 110. The concentrated cells were passed through a French Press (Model FA078, Spectronic, Golden Valley, Minn.) at 10,000 psi (~68.95 MPa) or 12,000 psi (~82.74 MPa) three times. The French Press processed samples (F1, F2, F3) and non-processed samples (F0) were diluted and serial dilutions were plated on LB plates with ampicillin (100 μg/mL). Table 11 showed the percentage of viable cells recovered from plating at each of the processed steps. It appeared that less percentage of cells were recovered for the QC3516 larger cells comparing to the QC1521 control cells after each pass of French Press. The larger cells of QC3516 showed increased efficiency of cell lysis by French Press. No significant difference of lysis efficiency was observed with the two different pressures (68.95 MPa vs 82.74 MPa) of French Press.

TABLE 11

Percentage of viable cells after each pass of French Press

| Percentage of viable cells | QC1521 | QC3516 | QC1521 | QC3516 |
| | 10,000 psi (~68.95 MPa) | | 12,000 psi (~82.74 MPa) | |
|---|---|---|---|---|
| F0 | 100.0 ± 17.2 | 100.0 ± 5.7 | 100.0 ± 17.2 | 100.0 ± 5.7 |
| F1 | 68.2 ± 4.5 | 22.1 ± 3.3 | 70.8 ± 0.0 | 15.0 ± 3.4 |
| F2 | 22.3 ± 2.3 | 2.8 ± 1.2 | 20.4 ± 3.1 | 4.1 ± 0.8 |
| F3 | 4.4 ± 1.6 | 0.8 ± 0.0 | 2.9 ± 0.4 | 0.6 ± 0.2 |

The same French Press processed samples (F1, F2, F3) and non-processed samples (F0) were also analyzed in the optical centrifuge (LUMiSizer®, L.U.M. GmbH, Berlin, Germany) under the following conditions: 2000 rpm, 25° C., 200 profiles, transmission profile taken every 15 seconds. The median of settling velocity of each sample was calculated and shown in Table 12.

TABLE 12

Median settling velocity of *E. coli* samples after each pass of French Press

| Median Settling velocity (μm/s) | QC1521 | QC3516 | QC1521 | QC3516 |
| | 10,000 psi (~68.95 MPa) | | 12,000 psi (~82.74 MPa) | |
|---|---|---|---|---|
| F0 | 57.8 | 78.5 | 54.1 | 69.0 |
| F1 | 12.2 | 25.1 | 14.3 | 23.2 |
| F2 | 34.1 | 40.5 | 28.5 | 53.7 |
| F3 | 52.3 | 66.6 | 29.0 | 54.3 |

The settling velocity of QC3516 cells was higher than that of the QC1521 control cells. The processed QC3516 samples after each pass of French Press also showed higher settling velocity than the respective samples of the control. Much slower settling velocity was observed in all F1 samples, which was likely due to an increase in viscosity after the first pass of French Press. The different settling velocity values of QC1521 and QC3516 cells in this example comparing to the Example 8 might be largely caused by different growth conditions.

What is claimed is:

1. A recombinant *Escherichia* host cell, comprising:
   i) a chimeric genetic construct encoding a peptide of interest; and
   ii) a set of genetic modifications comprising:
      a) a knockout mutation in gene gcvA;
      b) a knockout mutation in gene spr; and
      c) at least one mutation in the endogenous gene yejM from codon 241 to codon 568 corresponding to SEQ ID NO:482 that results in at least one amino acid insertion, substitution or deletion.

2. The recombinant *Escherichia* host cell of claim 1 wherein said at least one mutation is a truncation mutation or a transposon insertion to SEQ ID NO: 482.

3. The recombinant *Escherichia* host cell of claim 2 wherein the truncation mutation occurs at or after codon 262.

4. The recombinant *Escherichia* host cell of claim 3 wherein the truncation mutation occurs at codon 262 or codon 454.

5. The recombinant *Escherichia* host cell of claim 1 wherein said cell has increased recombinant peptide production, an improvement in median settling velocity, an increase in cell lysis efficiency or a combination thereof when compared to an *Escherichia* host cell lacking said set of genetic modifications.

6. The recombinant *Escherichia* host cell of claim 1, wherein the peptide of interest is from 14 to 600 amino acids in length.

7. The recombinant *Escherichia* host cell of claim 6 wherein the peptide of interest is a single chain peptide.

8. The recombinant *Escherichia* host cell of claim 1, wherein the *Escherichia* host cell further comprises a disruption in an endogenous genetic region selected from the group consisting of the araBAD operon and the slyD gene.

9. The recombinant *Escherichia* host cell of claim 7, wherein the peptide of interest has affinity for a body surface selected from the group consisting of hair, skin, nail, tooth, and tooth pellicle.

10. The recombinant *Escherichia* host cell of claim 9, wherein the peptide of interest is expressed as a fusion peptide that is insoluble within the *Escherichia* host cell, the fusion peptide having the general structure:

IBT-CL-POI or

POI-CL-IBT wherein;
IBT=at least one inclusion body tag;
CL=at least one cleavable peptide linker; and
POI=at least one peptide of interest.

11. A method of producing a peptide of interest in a recombinant *Escherichia* host cell, comprising:

a) providing a recombinant *Escherichia* host cell of claim 1,
b) growing the *Escherichia* host cell of (a) to produce the peptide of interest; and
c) optionally recovering the peptide of interest produced in step (b).

12. The method of claim 11 wherein said at least one mutation is a truncation mutation or a transposon insertion to SEQ ID NO: 482.

13. The method of claim 12 wherein the truncation mutation occurs at or after codon 262.

14. The method of claim 13 wherein the truncation mutation occurs at codon 262 or codon 454.

15. The method of claim 11, wherein the peptide of interest is from 14 to 600 amino acids in length.

16. The method of claim 15, wherein the peptide of interest is a single chain peptide.

17. The method of claim 11, wherein the *Escherichia* host cell further comprises a disruption in the endogenous araBAD operon, endogenous slyD gene or both.

18. The method of claim 16, wherein the peptide of interest has affinity for a body surface selected from the group consisting of hair, skin, nail, tooth, and tooth pellicle.

19. A method to optimize downstream processing of a recombinantly-produced peptide comprising:
   a) providing a recombinant *Escherichia* cell comprising at least one expressible chimeric genetic construct encoding a peptide of interest;
   b) introducing a set of genetic modifications to the recombinant *Escherichia* host cell of (a) comprising:
      i) a knockout mutation to gcvA;
      ii) a knockout mutation to spr; and
      iii) at least one mutation to yejM between codons 241 and 568 corresponding to SEQ ID NO:482, that results in at least one amino acid insertion, substitution or deletion; whereby a modified *Escherichia* host cell is produced;
   c) growing the modified *Escherichia* host cell under conditions whereby the peptide of interest is produced and wherein the modified *Escherichia* host cell demonstrates increased median settling velocity or enhanced cell lysis efficiency as compared to with a non-modified *Escherichia* host cell not having the set of genetic modifications; and
   d) optionally recovering the peptide of interest.

20. The method of claim 19 wherein said at least one mutation is a truncation mutation or a transposon insertion to SEQ ID NO: 482.

21. The method of claim 20 wherein the truncation mutation occurs at or after codon 262.

22. The method of claim 21 wherein the truncation mutation occurs at codon 262 or codon 454.

\* \* \* \* \*